US012727853B2

(12) United States Patent
Schaer et al.

(10) Patent No.: US 12,727,853 B2
(45) Date of Patent: Sep. 8, 2026

(54) INTRACARDIAC ECHOCARDIOGRAPHY CATHETERS, SYSTEMS, AND METHODS OF USE AND MANUFACTURE

(71) Applicant: Beluga Medical Inc., San Jose, CA (US)

(72) Inventors: Alan Schaer, San Jose, CA (US); Todor Jeliaskov, Boca Raton, FL (US); Jerry Hopple, Seebeck, WA (US)

(73) Assignee: Beluga Medical Inc., San Jose, CA (US)

(*) Notice: Subject to any disclaimer, the term of this patent is extended or adjusted under 35 U.S.C. 154(b) by 0 days.

(21) Appl. No.: 19/297,883

(22) Filed: Aug. 12, 2025

(65) Prior Publication Data

US 2026/0041397 A1 Feb. 12, 2026

Related U.S. Application Data

(60) Provisional application No. 63/740,123, filed on Dec. 30, 2024, provisional application No. 63/682,284, filed on Aug. 12, 2024.

(51) Int. Cl.

| | |
|---|---|
| ***A61B 8/12*** | (2006.01) |
| ***A61B 8/00*** | (2006.01) |
| ***A61B 8/08*** | (2006.01) |

(52) U.S. Cl.

CPC .............. *A61B 8/12* (2013.01); *A61B 8/0883* (2013.01); *A61B 8/4411* (2013.01); *A61B 8/445* (2013.01); *A61B 8/467* (2013.01); *A61B 8/5207* (2013.01); *A61B 8/56* (2013.01)

(58) Field of Classification Search

CPC ....... A61B 8/12; A61B 8/0883; A61B 8/4411; A61B 8/445; A61B 8/467; A61B 8/5207; A61B 8/56

See application file for complete search history.

(56) References Cited

U.S. PATENT DOCUMENTS

| | | | |
|---|---|---|---|
| 5,671,746 | A | 9/1997 | Dreschel et al. |
| 5,976,088 | A | 11/1999 | Urbano et al. |
| 6,004,270 | A | 12/1999 | Urbano et al. |
| 6,056,691 | A | 5/2000 | Urbano et al. |

(Continued)

FOREIGN PATENT DOCUMENTS

| | | |
|---|---|---|
| CN | 117618028 | 3/2024 |
| WO | 2024054935 | 3/2024 |

OTHER PUBLICATIONS

International Search Report and Written Opinion for International Patent Application No. PCT/US2025/041671, Applicant: Beluga Medical, Inc., mailed Dec. 10, 2025, 12 pages.

*Primary Examiner* — Baisakhi Roy

(74) *Attorney, Agent, or Firm* — ASHURST PERKINS COIE US LLP

(57) ABSTRACT

The present technology includes intracardiac echocardiography (ICE) systems and methods for enabling physicians to visualize heart anatomy and structure from within a patient's heart. For example, some embodiments described herein include ICE catheters with constructions for improved performance and ease of use. As another example, some embodiments described herein include ICE ultrasound assemblies expected to improve the imaging abilities of ICE systems, reduce clutter at or near an operating room table, and/or reduce the demand on healthcare resources.

20 Claims, 37 Drawing Sheets

(56) References Cited

U.S. PATENT DOCUMENTS

| | | | | |
|---|---|---|---|---|
| 6,312,381 | B1 | 11/2001 | Knell et al. | |
| 6,368,275 | B1 | 4/2002 | Sliwa et al. | |
| 6,468,213 | B1 | 10/2002 | Knell et al. | |
| 6,497,664 | B1 | 12/2002 | Randall et al. | |
| 6,503,204 | B1 | 1/2003 | Sumanaweera et al. | |
| 6,508,763 | B1 | 1/2003 | Urbano et al. | |
| 6,514,249 | B1 * | 2/2003 | Maguire | A61N 7/02 606/41 |
| 6,524,244 | B1 | 2/2003 | Knell et al. | |
| 6,592,521 | B1 | 7/2003 | Urbano et al. | |
| 6,592,524 | B2 | 7/2003 | Urbano et al. | |
| 6,595,921 | B1 | 7/2003 | Urbano et al. | |
| 6,605,043 | B1 | 8/2003 | Dreschel et al. | |
| 7,569,015 | B2 | 8/2009 | Donaldson et al. | |
| 7,641,480 | B1 | 1/2010 | Hossack et al. | |
| 7,678,048 | B1 | 3/2010 | Urbano et al. | |
| 7,789,833 | B2 | 9/2010 | Urbano et al. | |
| 7,984,651 | B2 | 7/2011 | Randall et al. | |
| 8,079,263 | B2 | 12/2011 | Randall et al. | |
| 8,213,693 | B1 * | 7/2012 | Li | A61B 34/20 600/407 |
| 8,220,334 | B2 | 7/2012 | Klessel et al. | |
| 8,312,771 | B2 | 11/2012 | Randall et al. | |
| 8,428,690 | B2 | 4/2013 | Li et al. | |
| 8,490,489 | B2 | 7/2013 | Randall et al. | |
| 8,499,634 | B2 | 8/2013 | Urbano et al. | |
| 8,600,299 | B2 | 12/2013 | Randall et al. | |
| 8,656,783 | B2 | 2/2014 | Randall et al. | |
| 8,790,263 | B2 | 7/2014 | Randall et al. | |
| 8,803,837 | B2 * | 8/2014 | Glynn | A61B 8/565 345/173 |
| 9,084,574 | B2 | 7/2015 | Randall et al. | |
| 9,116,226 | B2 | 8/2015 | Urbano et al. | |
| 9,295,444 | B2 | 3/2016 | Schwartz et al. | |
| 9,706,976 | B2 | 7/2017 | Randall et al. | |
| 10,052,431 | B2 | 8/2018 | Dreschel et al. | |
| 10,453,561 | B2 | 10/2019 | Balignasay et al. | |
| 10,514,738 | B2 | 12/2019 | Spencer et al. | |
| 10,736,602 | B2 | 8/2020 | Gubbini et al. | |
| 11,844,647 | B2 | 12/2023 | Loftman et al. | |
| 11,911,215 | B2 | 2/2024 | Salgaonkar et al. | |
| 12,115,019 | B2 | 10/2024 | Masters et al. | |
| 12,138,116 | B2 | 11/2024 | Gulsen et al. | |
| 2007/0161904 | A1 | 7/2007 | Urbano | |
| 2008/0112265 | A1 | 5/2008 | Urbano et al. | |
| 2008/0114241 | A1 | 5/2008 | Randall et al. | |
| 2008/0114246 | A1 | 5/2008 | Randall et al. | |
| 2008/0114247 | A1 | 5/2008 | Urbano et al. | |
| 2008/0114250 | A1 | 5/2008 | Urbano et al. | |
| 2008/0114251 | A1 | 5/2008 | Weymer et al. | |
| 2008/0139944 | A1 | 6/2008 | Weymer et al. | |
| 2008/0146940 | A1 | 6/2008 | Jenkins et al. | |
| 2008/0167650 | A1 * | 7/2008 | Joshi | C01B 7/14 606/41 |
| 2008/0188750 | A1 | 8/2008 | Randall et al. | |
| 2008/0188752 | A1 | 8/2008 | Randall et al. | |
| 2010/0168583 | A1 * | 7/2010 | Dausch | B06B 1/0622 600/466 |
| 2010/0286527 | A1 | 11/2010 | Cannon et al. | |
| 2012/0318038 | A1 | 12/2012 | Spigelmyer et al. | |
| 2016/0317131 | A1 | 11/2016 | Schwartz Klessel et al. | |
| 2018/0064415 | A1 * | 3/2018 | Zhai | A61N 7/02 |
| 2020/0054224 | A1 | 2/2020 | Corl et al. | |
| 2020/0060646 | A1 * | 2/2020 | Lindenroth | A61M 25/0147 |
| 2020/0061339 | A1 * | 2/2020 | Lindenroth | A61B 8/0883 |
| 2021/0367611 | A1 * | 11/2021 | Ouzounov | H03M 3/30 |
| 2021/0405721 | A1 | 12/2021 | Spencer et al. | |
| 2022/0175447 | A1 * | 6/2022 | Fedewa | A61B 18/1206 |
| 2022/0304661 | A1 * | 9/2022 | Chiang | A61B 8/467 |
| 2025/0228523 | A1 * | 7/2025 | Majerus | A61B 8/445 |
| 2025/0302443 | A1 * | 10/2025 | Urbano | G06T 1/0007 |

* cited by examiner

INTRACARDIAC ECHOCARDIOGRAPHY CATHETERS, SYSTEMS, AND METHODS OF USE AND MANUFACTURE

CROSS-REFERENCE TO RELATED APPLICATION(S)

The present application claims priority to U.S. Provisional patent application Nos. 63,682,284, filed Aug. 12, 2024, and 63/740,123, filed Dec. 30, 2024, each of which is incorporated by reference herein in their entireties.

INCORPORATION BY REFERENCE

All publications and patent applications mentioned in this specification are herein incorporated by reference in their entirety to the same extent as if each individual publication or patent application was specifically and individually indicated to be incorporated by reference.

TECHNICAL FIELD

The present technology generally relates to interventional imaging systems and methods, and in particular to intracardiac echocardiography catheters and associated ultrasound assemblies, systems, and methods.

BACKGROUND

Cardiac echocardiography (ultrasound) has existed for many years to image various cardiac and surrounding tissue structures and vessels. Typical types of cardiac ultrasound imaging include (a) trans-thoracic echocardiography ("TTE"), which uses a probe placed on the skin outside the chest, (b) trans-esophageal echocardiography ("TEE"), which uses a probe placed within the esophagus to allow imaging from the posterior aspect of the heart, and (c) intra-cardiac echocardiography ("ICE"), which uses a catheter placed within or adjacent to the heart itself, as advanced from a vessel leading to the heart.

Cardiac echocardiography, and ICE in particular, can be used to visualize many tissue structures to verify normal dimensions and function or diagnose abnormal dimensions and function, as well as to image devices within the heart (e.g., catheters, implants, etc.) and their relation to the tissue structures. Such tissue structures of the heart include but are not limited to: each heart chamber (right atrium (RA), left atrium (LA), right ventricle (RV), and left ventricle (LV), inclusive of local tissue structures within the chamber), the chamber walls, the inferior vena cava (IVC), the superior vena cava (SVC), the pulmonary artery (PA), the pulmonary veins (PVs), the left atrial appendage (LAA), the aortic valve (AoV) and pulmonary valve, the mitral and tricuspid valves (MV, TV), the papillary muscles and chordae, the coronary vessels, the coronary sinus (CS), and the pericardial space. Ultrasound catheters may also be used in doppler and color doppler mode to image the direction and velocity of blood movement within the heart. This can be useful to identify valve regurgitation, LAA contractility, and PV flow, among other uses.

ICE is a rapidly growing imaging procedure used to support a variety of interventional cardiac therapies. ICE may be used to produce real-time two-dimensional (2D) and three-dimensional (3D) images of cardiac tissue structures and other surrounding great vessels of the heart. Real time 3D imaging is also commonly referred to as "4D" in the industry. Except where distinctions are relevant, the term "ICE" will be used for both 2D and 4D catheters.

For many years ICE (beginning with 2D, but now rapidly including 4D) has been used primarily by electrophysiologists (EPs) to safely guide transseptal catheter access from the right atrium to the left atrium. Such "left-sided" access has enabled electrophysiology (EP) mapping and ablation catheters to reach targets within the left atrium (LA) and pulmonary veins (PVs) for treatment of atrial fibrillation (AF), as well as reaching regions near the aorta (Ao) and left ventricle (LV) for treatment of premature ventricular contractions (PVCs) and ventricular tachycardia (VT). With the advent of many new trans-catheter therapies, interventional cardiologists (ICs) have joined EPs in using ICE to guide placement of catheters within the heart to perform what are commonly referred to as "structural heart" procedures. These include, but are not limited to, valve repair and replacement, left atrial appendage occlusion or exclusion, patent foramen ovalis (PFO) closure, and other therapies for heart failure.

For example, TEE was originally and is still currently used prior to catheter interventions of the LAA to image the LAA to exclude the presence of thrombus and observe contractility. ICE catheters have also become a useful tool for this purpose, as operation may be performed directly by the interventionalist without the need for a dedicated sonographer. TEE also typically requires the use of general anesthesia (GA) for patient tolerance. Procedural use of TEE or ICE provides guidance for placing therapeutic devices within the LAA for left atrial appendage occlusion (LAAO). ICE imaging of the LAA to exclude thrombus is preferably conducted from the right side of the heart, prior to accessing the left side, so as to limit further interventions in case thrombus is identified (catheter intervention of the LAA is contraindicated when thrombus is present due to the risk of dislodging the thrombus and increasing the likelihood of the patient experiencing a stroke). While imaging of the LAA from the left side (with the ICE catheter placed transeptally) is frequently performed, there is a general preference to be able to conduct such imaging from the right side of the heart to minimize the number of catheters crossing the septum and possibly interfering with the view of the LAA and/or LAAO device. In general, image quality of left-sided structures produced from a catheter in the RA is often impacted by intervening structures, devices, and distance to the target area. Improved imaging of the LAA and other left-sided structures from the right-side has been achieved from locations within the PA and CS as these vessels course directly next to the left atrium.

While much of the disclosure herein relates to the heart and great vessels in communication with the heart, operation of the devices could also be within any interior body lumen, particularly ones that are filled or can be filled with a fluid, gel, or other medium (or the medium physically placed directly between the transducer and the tissues) that can couple ultrasound energy to the body tissues of interest.

Current Limitations

While ICE catheter placement into the PA and CS has been reported, performing this procedure with current ICE catheters is generally considered by most interventionists as an advanced maneuver to be performed only by highly skilled users. PA access requires directing the catheter from a position in the RV, to the RV outflow tract (RVOT), and further up across the valve of the pulmonic artery. The RVOT free wall thickness is relatively thin, and most users fear the risk of perforating the RVOT free wall with aggressive catheter manipulation. Most ICE catheters are built to be torqueable and stable within the cardiac chamber (minimizing catheter imaging transducer movement helps minimize imaging artifacts). This typically results in a catheter that has a relatively stiff body, and due to transducer construction, a relatively stiff and unyielding tip. Similarly, placement of an ICE catheter into the CS is also difficult. The orientation of the CS ostium relative to the IVC (the most common access route) is at a sharp angle, the ostium may have patient-patient variations in the structure of the thebesian valve, thereby complicating access, the venous wall of the CS is relatively thin, and the size of the CS may limit how far a catheter may be advanced, with increasing catheter diameter posing more difficulty.

While ICE catheters may be constructed for placement in a particular anatomy, they do need to be used in a variety of locations throughout the procedure. For example, placement may be initially in the RV/RVOT/PA to assess LAA thrombus, but then need to be repositioned stably in the RA to guide transseptal access. From there, they may be ideally advanced to the PA or CS to guide a procedure, but in some cases need to be placed transeptally for optimal procedural imaging.

Another limitation of ICE catheters is optimizing orientation of the transducer relative to the imaging target of interest. This includes two main aspects: 1) proximity of the transducer to the imaging target, and 2) alignment of the optimal imaging axis to the imaging target. Proximity can either be too close or too far away depending on the circumstance. Too close, and the field of view is too small; too far, and the resolution is too poor. The transducer located at a tip of the ICE catheter is oriented to one side of the catheter and is dependent on a deflection over a sweeping arc to move it closer or farther away from the target. While the desire may be to translate the transducer closer or further away, the sweeping arc causes the orientation angle of the transducer to change at the same time, resulting in loss of the optimal field of view. Alignment of the transducer is also problematic in some cases. For example, when placing the transducer in the left atrium to image the mitral valve for a mitral valve clip procedure, the natural orientation of the preferred azimuthal imaging plane (having the most elements along the length of the catheter), may be as much as 90 degrees off the desired plane of interest. This requires further manipulation of the catheter to better optimize, which may be difficult to achieve.

Another limitation of ICE catheters is image penetration. As noted, imaging from the RA may have limitations due to intervening tissue structures and devices. Image quality at deeper depths (penetration), is limited by the total power supplied to the transducer. This power may be limited by the catheter supply voltage to the piezoelectric material and the dielectric limits of the catheter insulation. However, other limitations include the thermal heat transfer to the tissue from heat losses within the transducer tip. Some heat buildup may come from the imaging transducer losses, and in the case of 4D transducers, the heating of the circuit adjacent the transducer (e.g., the ASIC chip technology). ICE catheters must meet standardized tests to demonstrate the catheter tip to tissue interface does not exceed regulatory limits (e.g., 43° C.). As a result, many catheters must throttle the power to the transducer to ensure this requirement is met. Demonstration of this may be either through empirical tests to demonstrate a temperature limit is never exceeded at the target powers, and/or via other devices that employ thermal monitoring as a safeguard against unintended thermal rises.

DETAILED DESCRIPTION

Figure 1B:
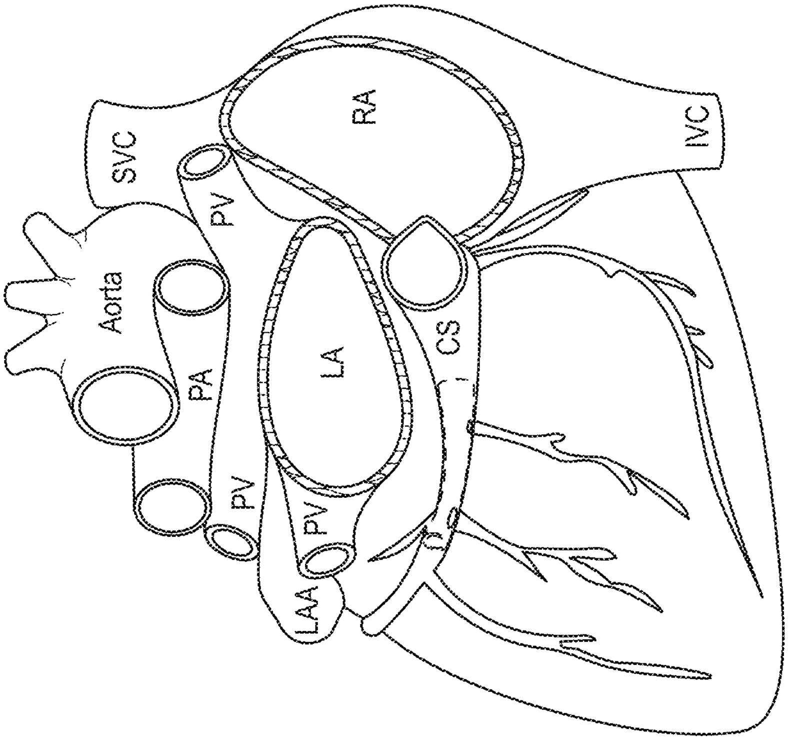
FIGS. 1A and 1B are anterior and posterior views, respectively, of a cardiac anatomy of a patient's heart.

The present technology is generally directed to intracardiac echocardiography (ICE) systems and methods for enabling physicians to visualize heart anatomy and structure from within a patient's heart. For example, some embodiments described herein are directed to ICE catheters having a handle, a shaft extending from the handle, and distal end region with a transducer for converting electrical energy into ultrasound energy and vice versa. As will be described throughout this Detailed Description, the ICE catheters described herein may be designed to provide one or more of the following advantages: (a) improved atraumatic access within delicate tissue structures while maintaining the ability to image from traditional locations with sufficient support and image quality; (b) ability to re-orient the transducer proximity to tissue independent of the sweeping deflection arc of the catheter, and to alter the azimuthal alignment of the transducer relative to the target tissue independent of the primary catheter deflection, and/or (c) ability to cool the transducer tip to allow for increased power delivery to the transducer that can enhance the penetration capability of the transducer. However, as one skilled in the art will appreciate from the Detailed Description, the present technology may include additional advantages in addition to or in lieu of those described above, including achieving improvements in ICE imaging.

For example, the present technology also provides improved ICE ultrasound assemblies. Historically, ultrasound imaging originated with the use of external probes that could be cleaned and reused (via wiping down the probe after external skin use, or more robust cleaning/sterilization after use in the esophagus or bronchial spaces). The probes required connection to a single imaging system or console to view and manipulate the images. Given that these probes had large transducer arrays and were reusable, the probes were configured with the transducer integrated with a large cable and large connector that plugged directly into the ultrasound imaging system. In contrast, ICE catheters must be sterile for intravenous use, and thus are labeled for single use such that a new catheter is purchased for each patient. Despite this, ICE catheters are typically made to work with existing ultrasound consoles with the large connection mechanisms. For example, ICE catheters generally have a connector that remains in the sterile field, but are further connected to a non-sterile cable (either positioned outside the sterile field or within a protective sterile sleeve if the connection is made in the sterile field) that is similar in construction to the cables of larger probes of non-ICE applications, and which is long enough (e.g., typically greater than 3 meters in length) to reach the location of the console, which may vary from lab to lab. Conventional ICE catheters thus generally have a connector similar to those larger probes that plug into the common ultrasound consoles. This typical setup is further engrained because ultrasound system manufacturers/providers have a strong financial incentive to place a single expensive imaging system in a site such as a hospital or related medical center such that the site is dependent on that system for imaging and future purchases of probes. The operation of such complex and multi-faceted imaging system has also traditionally required dedicated trained operators.

Embodiments of the present technology improve upon these conventional systems and approaches by providing ICE-specific ultrasound systems that improve the imaging abilities of ICE systems, reduce clutter at or near an operating room table, and/or reduce the demand on healthcare resources. For example, some embodiments described herein describe ultrasound assemblies including a first housing having an analog-front-end of the ultrasound assembly, connected via a cable to a second, separate housing, having an image processing unit of the ultrasound system. The first housing can also be connected to an ICE catheter via a connection assembly. Advantageously, the connection assembly can have a length of less than about 3 meters (e.g., such as less than about 2 meters) to minimize the distance that analog signals must be transmitted before being digitized. As explained in greater detail below, reducing the distance analog signals must be transmitted before being digitized in ICE is expected to reduce signal loss and attenuation and improve the quality of the resulting image construction. The first housing may also have a relatively small form factor compared to conventional ultrasound assemblies that enables it to be positioned at or near the ICE catheter while not getting in the way of the surgeon. The ICE ultrasound modules described herein can have additional advantages as described in greater detail throughout this Detailed Description.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-29.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

As used herein, the use of relative terminology, such as "about", "approximately", "substantially" and the like refer to the stated value plus or minus ten percent. For example, the use of the term "about 100" refers to a range of from 90 to 110, inclusive. In instances in which the context requires otherwise and/or relative terminology is used in reference to something that does not include a numerical value, the terms are given their ordinary meaning to one skilled in the art.

Figure 1A:
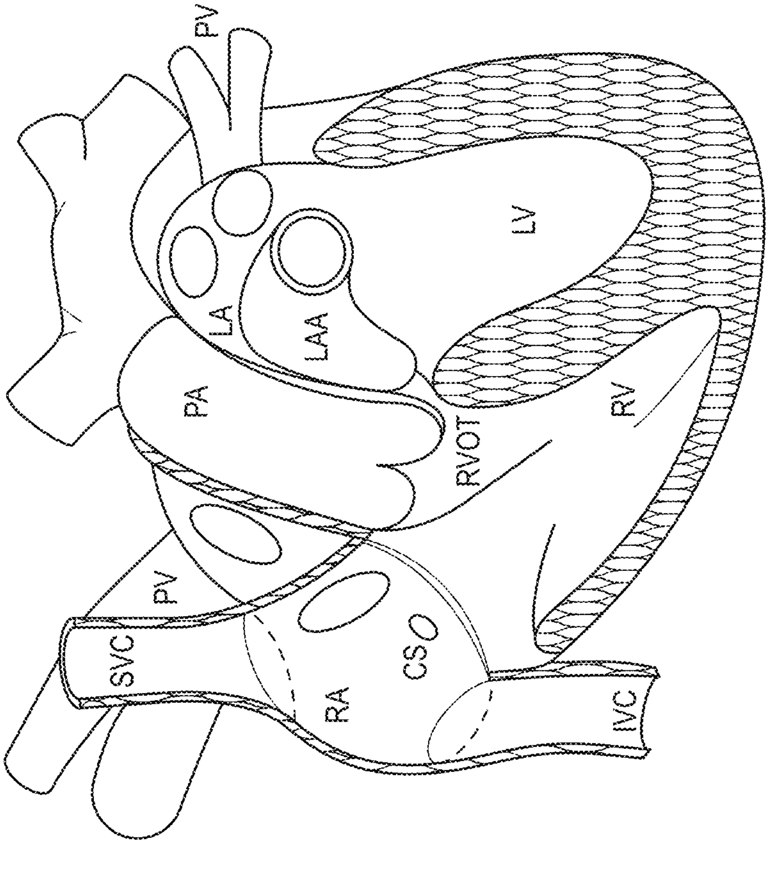

FIGS. 1A and 1B provide an overview of cardiac anatomy and the location of specific cardiac structures, with FIG. 1A viewed from an anterior aspect, and FIG. 1B viewed from a posterior aspect. Any of the anatomical structures herein may be described in reference to those shown in FIGS. 1A and 1B.

Figure 2:
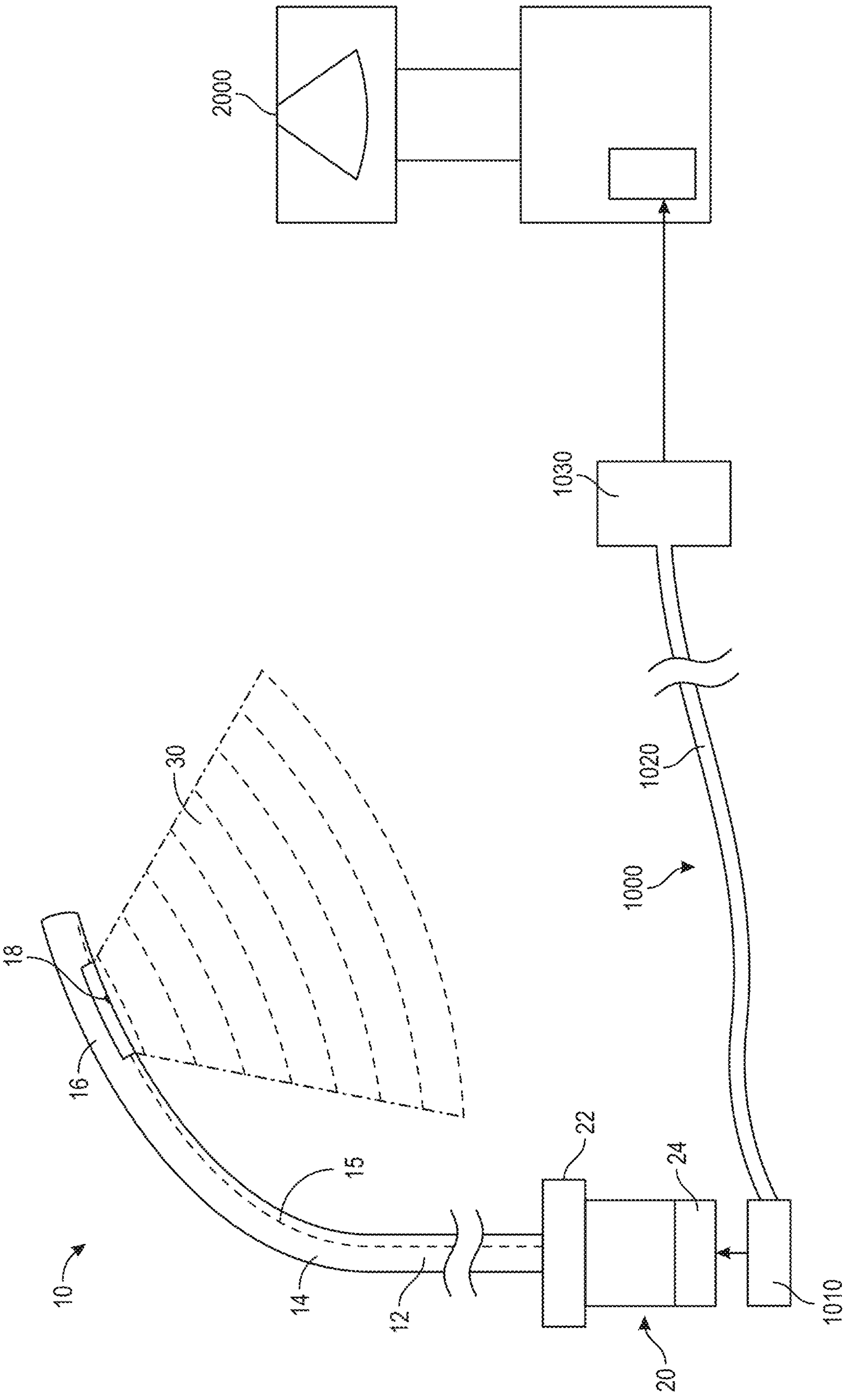
FIG. 2 is a schematic illustration of an ICE catheter apparatus configured in accordance with embodiments of the present technology.

FIG. 2 provides an overview of an ICE system 1 having an ICE catheter apparatus 10 and an ultrasound imaging assembly or system 2000. The ICE catheter 10 can include an elongated proximal shaft 12, a more flexible distal deflection region 14, a transducer tip region 16, and an imaging transducer 18. The catheter 10 also has a proximal handle 20 that includes at least one mechanical control mechanism 22 and an electrical connector receptacle 24. A user can deflect the distal region 14 by manipulating one or more pull lines 15 that are attached or coupled (e.g., directly or indirectly) to the mechanical control mechanism 22 in the handle 20 and routed through the inside of the catheter shafts 12 and 14 to an anchor point distal to the distal flexible region 14. The pull lines 15 are configured to transmit a tensile force from the proximal end of the device to the distal anchor point. The pull lines 15 can be composed of materials known in the art, such as stainless steel, nitinol, or high strength polymer strands such as aramid fibers. The pull lines 15 may be any single strand or multi-stranded (preferably braided) combination of these materials. The pull lines 15 may have a cross section which is substantially round, or purposely non-round, such as a flattened wire or ribbon. Any of the catheter and system structures shown and/or described herein in the examples and embodiments that follow may be made with reference to general catheter and system structures shown in FIG. 2 (for example only, catheter 10, deflection region 14, tip region 16, etc.).

The ultrasound imaging system 2000 is made with an interface cable 1000 that has a catheter-side connector 1010, a cable body 1020, and system-side connector 1030. The imaging transducer 18 converts electrical energy supplied by the system 2000 into acoustic (ultrasound) waves (also referred to as a beam, acoustic energy, or acoustic power) 30 in a given field of view which are sent and received by the transducer 18. The system 2000 in conjunction with the transducer 18 can steer the ultrasound waves and change the depth, field of view, power, etc.

Figure 3B:
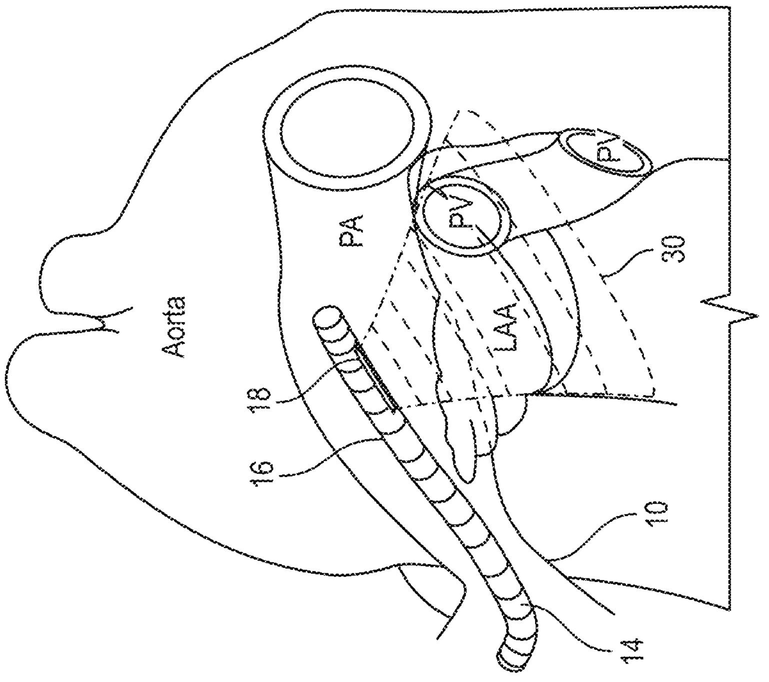
FIGS. 3A and 3B illustrate various views of using the ICE catheter of FIG. 2 to perform an imaging procedure within a patient's heart in accordance with embodiments of the present technology.
Figure 3A:
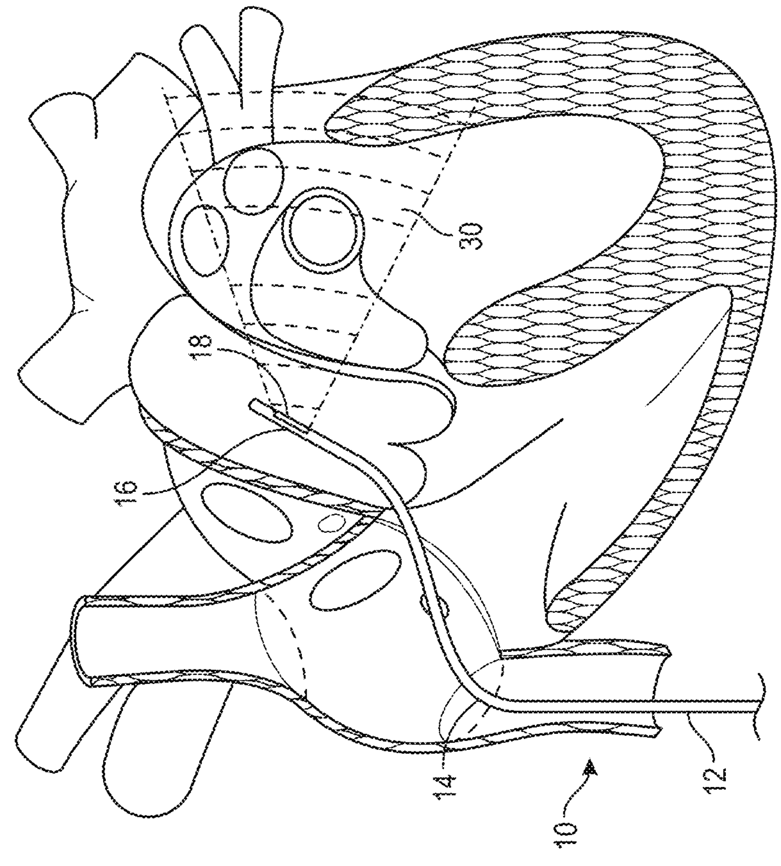
Figure 4:
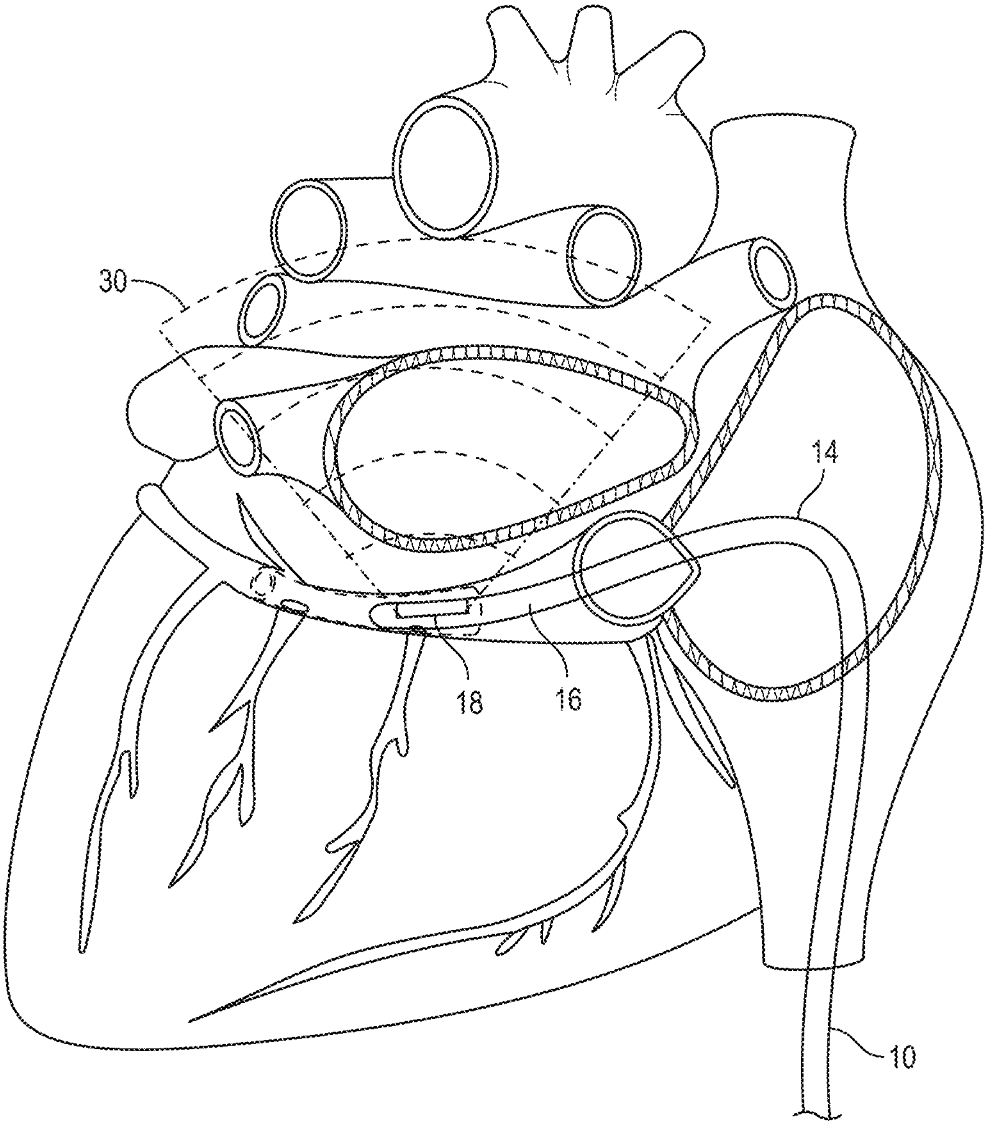
FIG. 4 illustrates using the ICE catheter of FIG. 2 to perform a different imaging procedure within a patient's heart in accordance with embodiments of the present technology.

FIG. 3A illustrates how the ICE catheter 10 can be positioned in the pulmonary artery (PA) to view a left atrial appendage (LAA). FIG. 3B similarly illustrates the placement of the distal end of the ICE catheter 10 in the PA, but as shown from more of a left anterior view for additional clarity. FIG. 4 illustrates how the ICE catheter 10 can be placed into the CS from the IVC/RA to image into the LA, LAA, and PVs from the posterior aspect of the heart. These locations are also targets for the catheter embodiments described herein. Indeed, any of the catheters and methods of use described herein may be made with reference to general catheter method of use and placement shown in FIGS. 3A and 3B (for example only, access routes and/or transducer placement).

Figure 5:
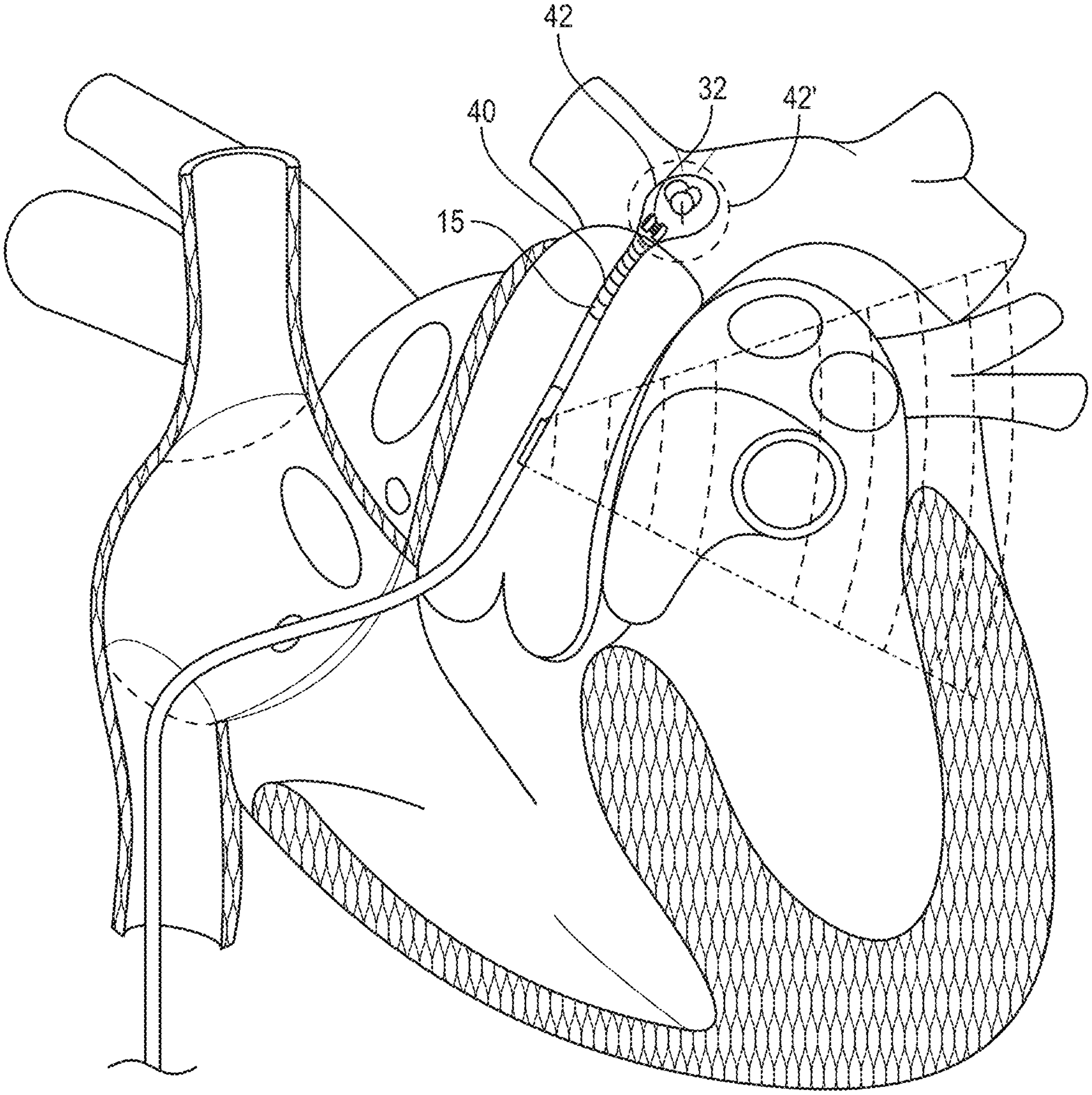
FIGS. 5-9 illustrate various operations of ICE catheters configured in accordance with embodiments of the present technology.

FIG. 5 shows an embodiment of the ICE catheter 10 that incorporates a distal extension 40 beyond the transducer tip, and may further include a more atraumatic feature/member 42. The distal extension 40 is adapted to be more flexible than the tip region 16 in FIG. 2, and preferably softer (more flexible) than the distal deflection region 14. The distal extension 40 may be a soft structure that has no specific control mechanism, but may be optionally pre-shaped for optimal atraumatic advancement (e.g., shaped into an angle of 30-270 degrees, preferably 180 degrees). In another embodiment, the distal extension 40 may be deflectable independent of the deflection region 14, to a degree comparable to the aforementioned pre-shaped degrees. Deflection of the distal extension 40 may be achieved using a tip pull line (not shown but substantially the same as the pull line 15 described for FIG. 2), independent of the pull line 15 for region 14. The pull line would be secured proximally to a mechanism 22 (FIG. 2) and routed to an anchor point distal of the transducer tip region 16, within the extension 40 or feature 42. In an alternative embodiment, both the distal extension 40 and the deflection region 14 could be deflected together with a single pull line 15 anchored distal to the transducer tip region 16. Construction of the distal extension 40 is preferably of a solid, soft polymer material, round or oval in cross section. The pull line can be positioned in a separate lumen, eccentric to the central axis of the catheter 10, aligned to the side opposite the transducer face and an anchor feature 32 embedded distally, preferably within feature 42, to secure the pull line 15. The anchor feature 32 could be a metal, preferably radiopaque, such as platinum-iridium and other materials known in the art, formed into the shape of a ring, "T", cylinder, spool-shaped with a central transverse hole, or other common shape. The material of the extension 40 and the feature 42 may be that of a radiopaque polymer compound, such as a 25D-40D pebax loaded with Barium Sulfate or tungsten powder. The material may alternatively be an extension of the same polymer material surrounding the transducer 18, such as a clear pebax 25D or 35D. The material may be further reinforced with a braid (including any combination of stainless steel, nitinol, or aramid fibers), or a coil (e.g. stainless steel or platinum-iridium), or a single tapered core wire (e.g., stainless steel or nitinol). The extension 40 may be 1-6 cm long, such as about 3 cm.

In another embodiment also illustrated in FIG. 5, the feature or member 42 is an expandable member that when expanded to position 42' is configured to advance with blood flow, as this may help "float" the catheter up the PA or elsewhere in the heart. In one embodiment the feature 42/42' may be a nitinol support structure integrated with a membrane between nitinol splines. The construction and expanded state may look like a basket or flower petals. In another embodiment, it may be an expandable balloon, made of either compliant or non-compliant material (e.g., polyurethane, silicone, nylon, polyethylene, PET, or any compounds thereof).

Figure 6:
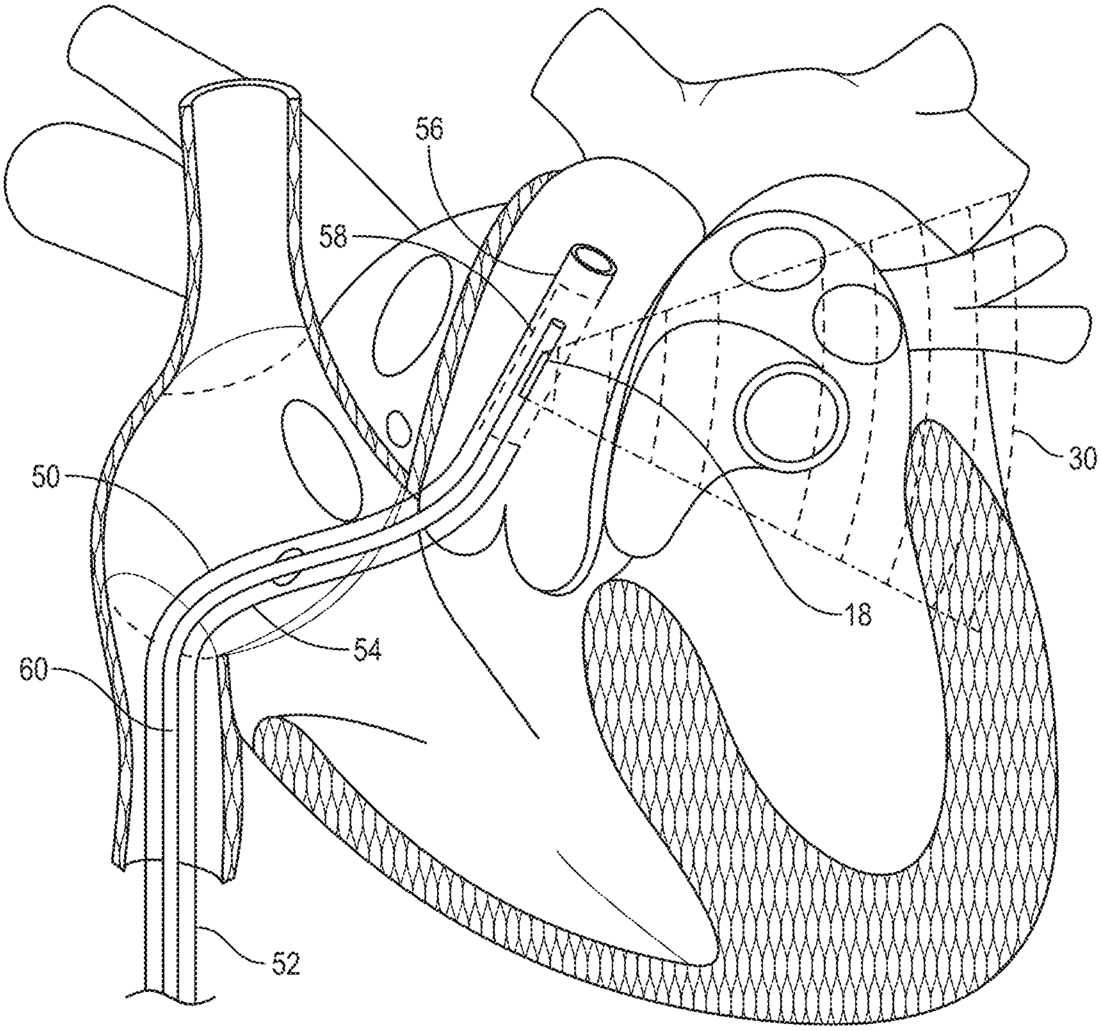

FIG. 6 illustrates an alternative example, including an approach to delivering an ICE catheter. In this embodiment, an imaging sheath 50 is first advanced into the heart. Advancement of the sheath 50 into the anatomy may be achieved by conventional means, using a conventional dilator and guidewire (not shown) known in the art. In this case, the dilator extension past the tip of the sheath would be configured to be relatively soft and conformable to the anatomy, providing a smooth stiffness and edge transition from the guidewire to sheath. The sheath 50 comprises a proximal shaft 52, a distal deflection region 54, a distal tip region 56, and an imaging window 58. Construction of the sheath 50 may be similar to those known in the art, such as those produced by Terumo, St. Jude/Abbott, and Biosense Webster. The sheath 50 has a central lumen through which an ICE catheter 60 may pass and may be steerable with a handle and pull line similar to or equivalent to that used in ice catheter 10 of FIG. 2. While the ICE catheter 60 could be configured similar to IC catheter 10 described above, it does not necessarily need any deflection capability, as that is provided by the sheath 50.

An important distinction of the sheath 50 is that the distal region 56 of the sheath extends distal to the imaging transducer 18 (said another way, the imaging transducer does not exit the distal end of the sheath). In order to ensure adequate imaging, an imaging window 58 is provided to align with the imaging transducer 18 of the ICE catheter 60. As explained below, the window 58 is constructed to ensure minimal losses of acoustic energy 30 passing out of the transducer 18, and thus to ensure adequate image quality of the tissues and/or devices of interest, the window 58 may be formed from a variety of polymer materials, though preferably not of a composite. The window 58 may incorporate Pebax 25D or 35D material which has better acoustic matching to blood, or be thinner wall material such as PET, preferably at a thickness less than $\lambda/4$. The window 58 is also preferably over at least half the circumference of the diameter of the sheath 50, and as long or longer than the transducer 18. An advantage of the sheath 50 extending beyond the transducer 18 is to allow saline flush fluid from the sheath 50 to pass over the distal tip region 56. This will help reduce the temperature of the probe and allow greater imaging power to be delivered to the transducer 18 (and/or any circuitry behind the transducer 18) for improved image penetration. In an alternative embodiment, the sheath 50 could be configured to have a closed lumen at the tip, and lumens constructed within the sheath 50 to allow any fluid delivered to the tip to be directed proximally via a separate pathway, preferably to a location outside the body. Embodiments for how the fluid may be introduced and, as applicable, removed from the sheath 50 from the proximal end are equivalent to those described below for FIGS. 10 and 11. In another specific embodiment, the fluid return could still be within the body, but with the exit at a more proximal location that would not be at risk of placement in the left side of the heart. This would reduce the risk severity of inadvertent left-sided air embolism.

In another embodiment and specific method of use, the ICE catheter 60 is advanced into the sheath 50 prior to being introduced to the patient. In this case, prior to insertion in the body, the transducer 18 can be confirmed to be properly aligned with the window 58 and all air purged from the lumen. Preferably, the window 58 is constructed to be 360 degrees to remove any concern of rotational alignment. However, a custom lock feature (e.g., a keyway or other reversable engagement feature) between the distal catheter handle and proximal hub of the sheath 50 could be used to ensure rotational alignment is maintained, particularly if one part of the window 58 has poor acoustic transmission.

Figure 7:
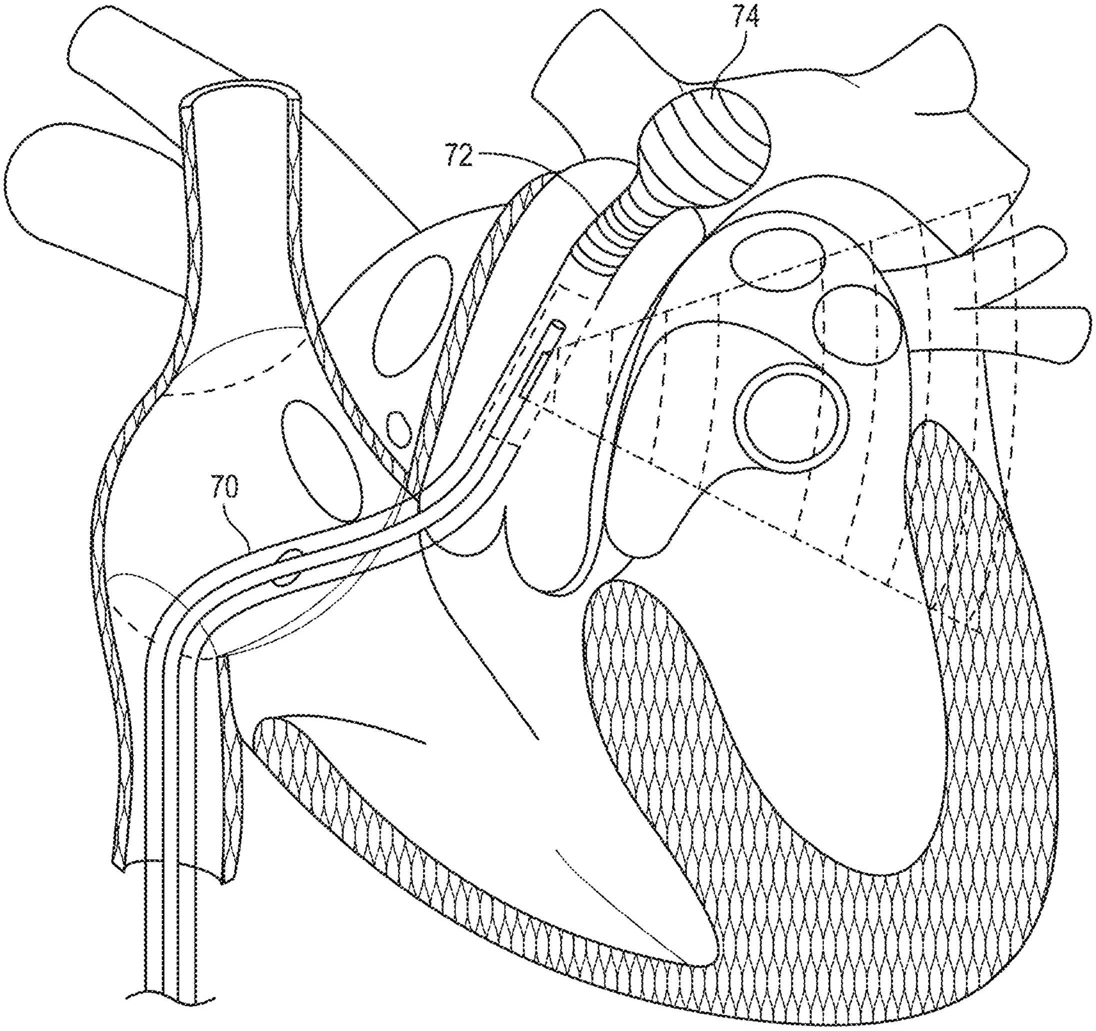

FIG. 7 illustrates another embodiment of a sheath 70, which has similar features to the sheath 50 of FIG. 6, including a central lumen, deflection, and an imaging window. In this embodiment, the sheath 70 incorporates a distal extension 72 and atraumatic feature/member 74. Construction may closely mimic that described above for the extension 40 and the feature 42 in FIG. 5. A similar ability to deflect the distal extension may be incorporated.

Figure 8:
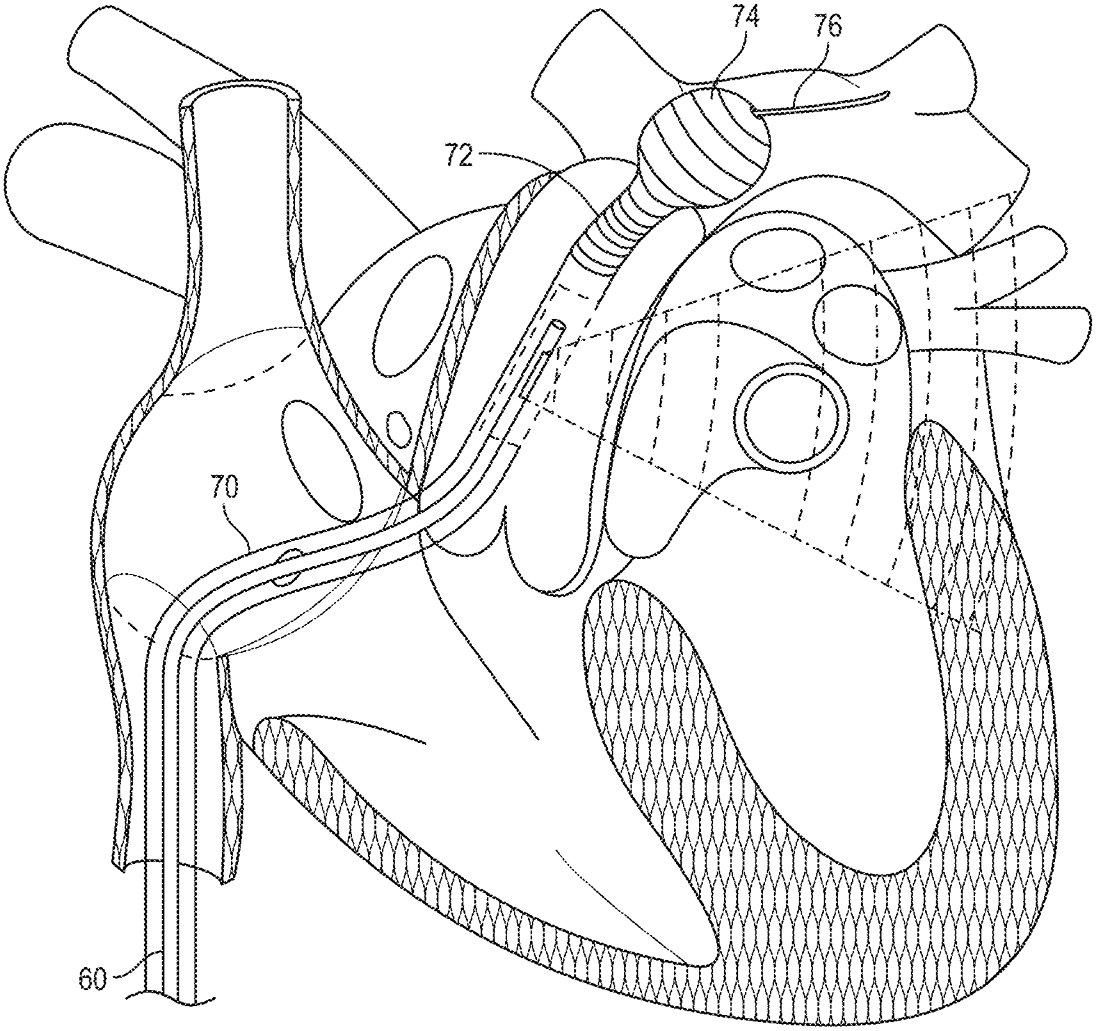

FIG. 8 illustrates the sheath 70 of FIG. 7 but with a central lumen that enables passage of a guidewire 76 through the distal tip of sheath 70. The guidewire 76 may be advanced inside the sheath 70, alongside the imaging catheter 60, or, if the imaging catheter 60 had its own guidewire lumen, the wire 76 may be allowed to pass through the distal end of the sheath.

Figure 9:
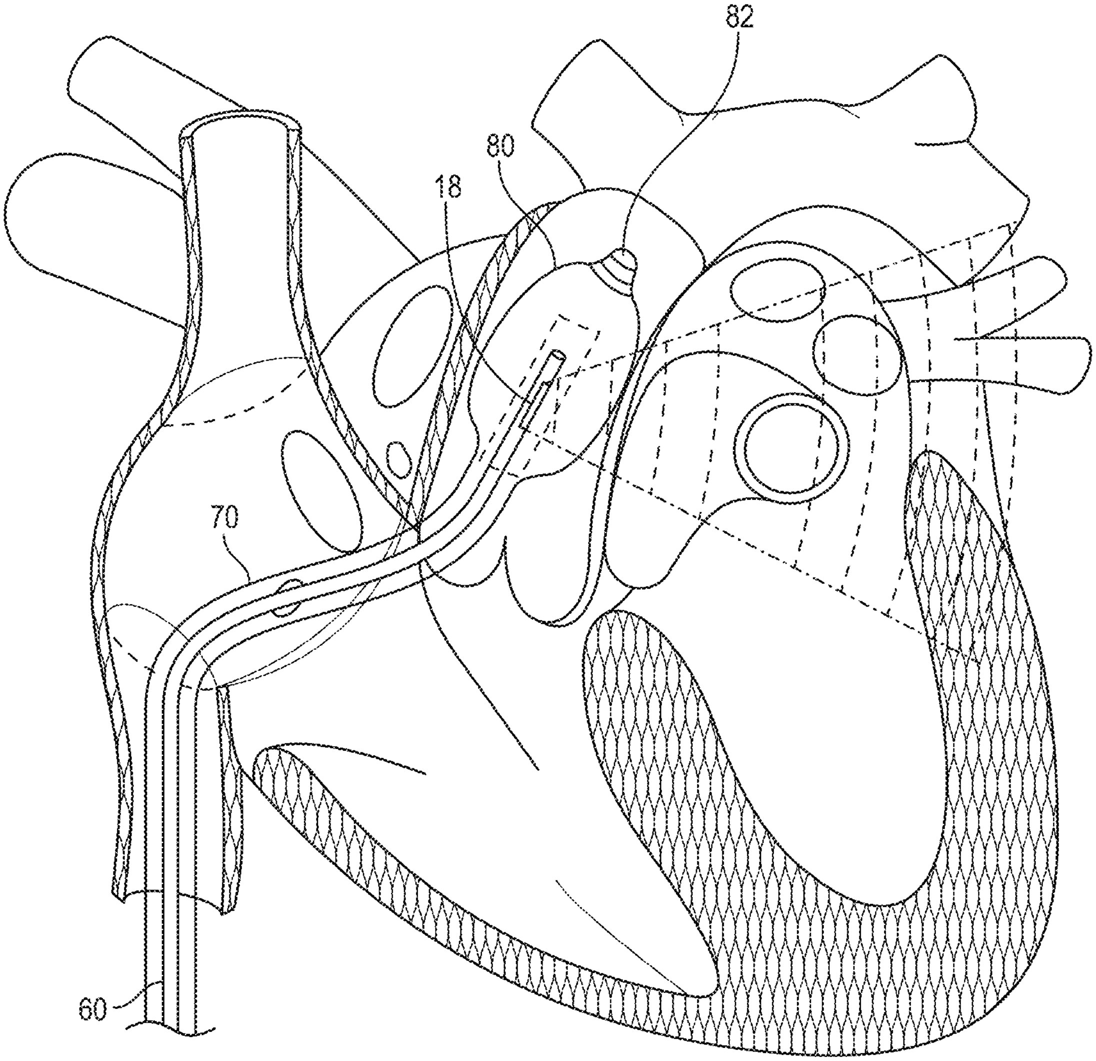

FIG. 9 illustrates another embodiment of the sheath 70 of FIG. 7, but in this case incorporating an expandable chamber 80 near the distal end of the sheath 70 that aligns with the imaging transducer 18 of the catheter 60. In this embodiment, the expandable chamber 80 allows a greater amount of fluid to surround the transducer 18 to improve cooling and visibility. It may also help the sheath "float" up into the PA or other location in the heart. In one form, the expandable chamber 80 is a balloon, though other means of providing such a volume may be contemplated, such as splines surrounded by (and optionally coupled to) a membrane previously described. This latter embodiment may be useful to control the fold or make the inflation less dependent on the fluid circulation pressure. The balloon may be made of a compliant material such as polyurethane or silicone, or a more non-compliant material such as polyethylene, nylon, PET or some other novel polymer blend. The expandable chamber 80 may have a feature/member 82, such as a thicker material or nipple that accommodates the distal end of the imaging catheter 60. Delivery of fluid into the sheath 70 to expand the expandable chamber 80 may be achieved via a proximal port (not shown) such as that described below for embodiments illustrated in FIGS. 10 and 11.

Figure 10:
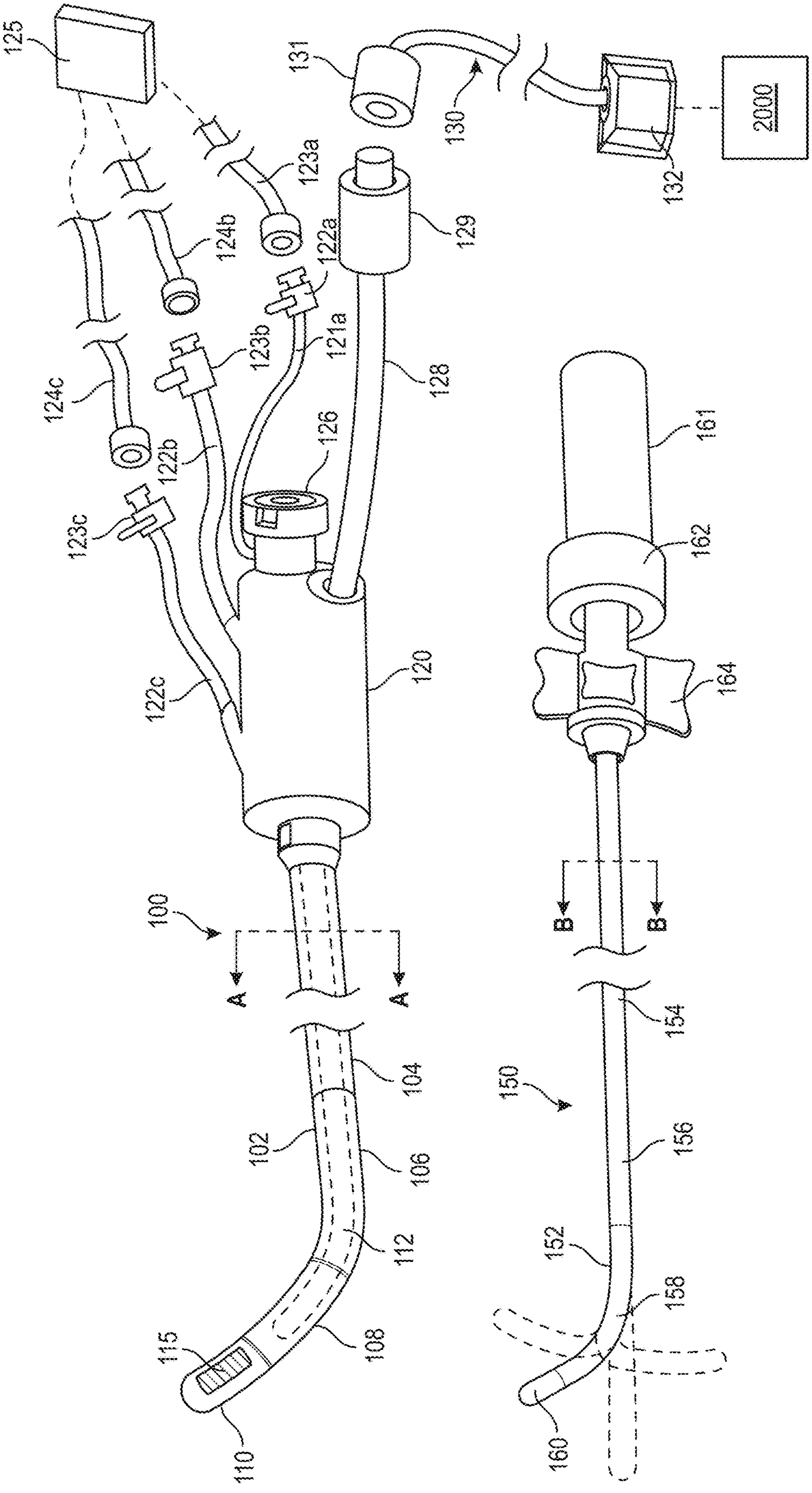
FIGS. 10 and 11 Illustrate ICE catheters having separate steering catheters and configured in accordance with select embodiments of the present technology.

Depending on the target anatomy, operators may need a catheter which is flexible or floppy, or stiffer and more steerable. In FIG. 10, an ICE catheter 100 is shown with a separate steering catheter 150 which is inserted inside a lumen 112 passing through the interior of catheter 100 and sized to accept the catheter 150. The bottom drawing in FIG. 10 shows the steering catheter 150 outside of the catheter lumen 112. Section A-A also illustrates the lumen 112 in FIGS. 12A-12C.

The ICE catheter 100 is comprised of a shaft 102 and an operator handle 120. The shaft 102 has a working length of approximately 90 cm long, but could be as long as 130 cm to reach more distal anatomy. The shaft 102 is comprised of at least a proximal shaft or section 104, a middle shaft or section 106, and a distal shaft or section 108. The proximal shaft section 104 is generally more rigid and torqueable than the middle and distal shaft sections 106, 108 and may have a working length of up to 75 cm. The distal shaft 108 is more flexible and compliant such that it may be advanced easily through large vessels of the heart such as the coronary sinus and pulmonary artery, or deeper into the left ventricle. The distal shaft 108 may have a typical length of 25 cm, but ranges from 10-40 cm. The middle shaft 106 is configured to transition the stiffness between the proximal and distal shafts, and have an appropriate length and construction for this. The tip region 110 houses the imaging transducer 115, is relatively rigid, and may be 1-3 cm long. The lumen 112 passes the full length or substantially the full length of the catheter shaft sections.

Figures 14A, 14B, 14C:
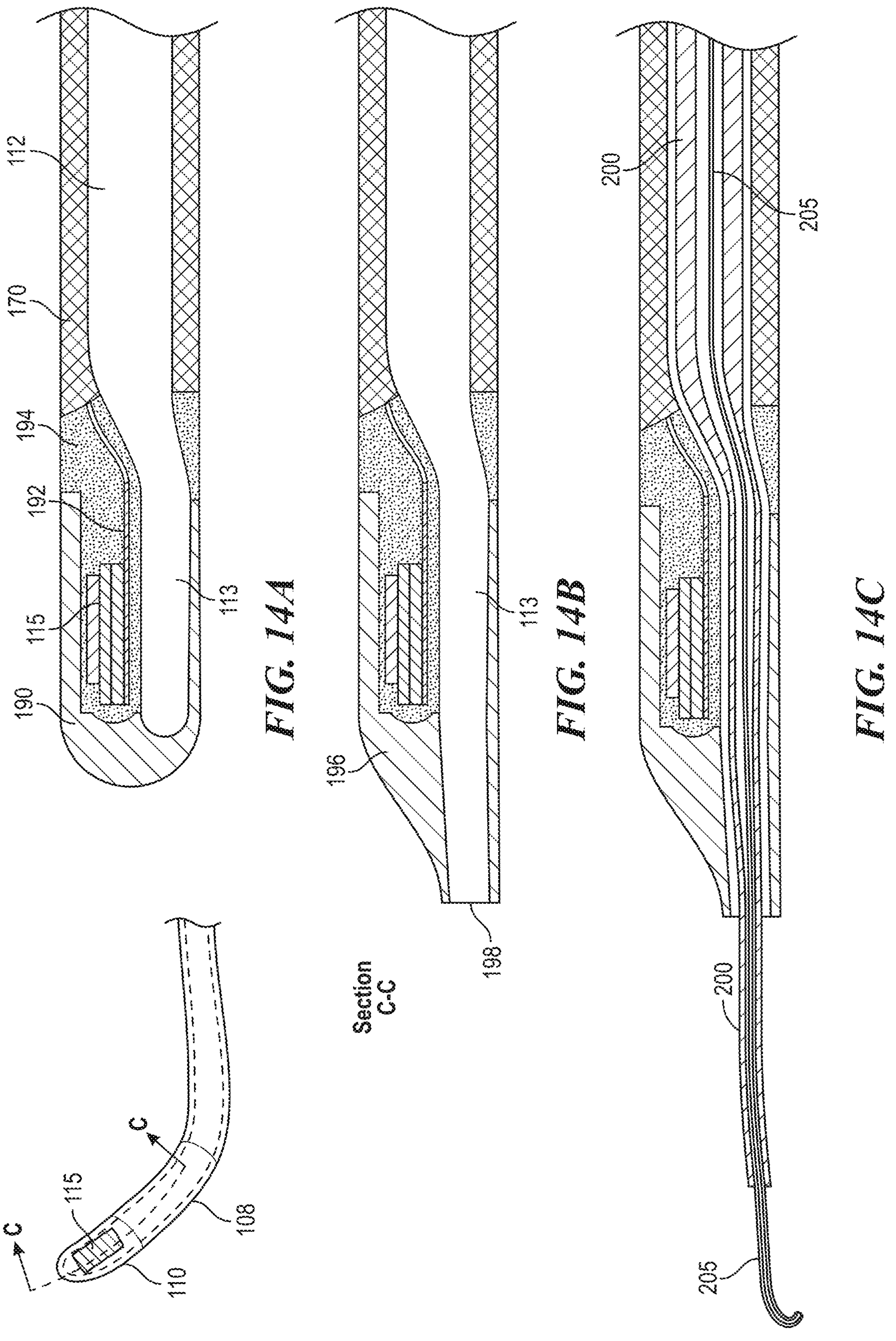

Lumen 112 of FIG. 10 may terminate distally at the proximal end of the tip region 110, or as illustrated in FIG. 14A, continue underneath the transducer 115 where it is designated lumen 113, but be closed at the very distal tip. Note that FIG. 14A also illustrates a tip material 190 surrounding the transducer 115. The tip material 190 may be a soft material with good acoustic matching to blood, such as Pebax 25D or 35D. It may be formed or molded directly around the transducer 115, or bonded with a thin layer of polymer adhesive 194 that has good acoustic matching to the transducer 115 and the tip material 190. In another embodiment, the lumen 113 may continue to exit the distal end of catheter 100 at distal opening 198, as shown in FIG. 14B. To accommodate the limited space, the lumen 113 may be smaller than the lumen 112, and thus the distal segment 160, and possibly the shaft 158, of the catheter 150, would have a reduced diameter to fit in the smaller lumen 113. The shape of the tip material 190 may be altered to that shown in the tip 196 of FIG. 14B such that it is tapered toward the lumen exit 198 for an improved transition.

As further illustrated in FIG. 14C, the configuration of FIG. 14B could be made to accept a guidewire 205, either alone, or used with the aid of a dilator 200. If the lumen 112 was sized to match the lumen 113, the outer diameter of the dilator 200 may be the same over its total length. However, in the case of the lumen 113 being smaller than the lumen 112, then the dilator 200 preferably has a taper to a smaller OD for a close fit in the lumen 113. Guidewire 205 may be passed through the center lumen of the dilator 200. In another embodiment (not shown), the dilator 205 could be configured to be solid (no central lumen), with a soft rounded tip such that it makes a smooth, atraumatic transition past the catheter tip 196.

Figure 12A:
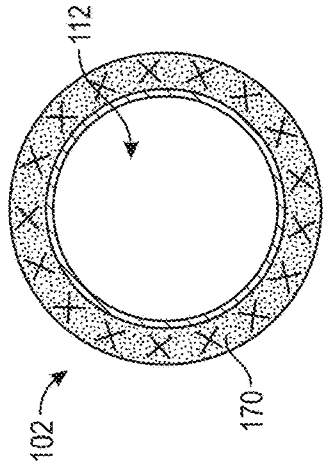
FIGS. 12A-14E are various cross-sectional views of the catheters shown in FIGS. 10 and 11.
Figure 12B:
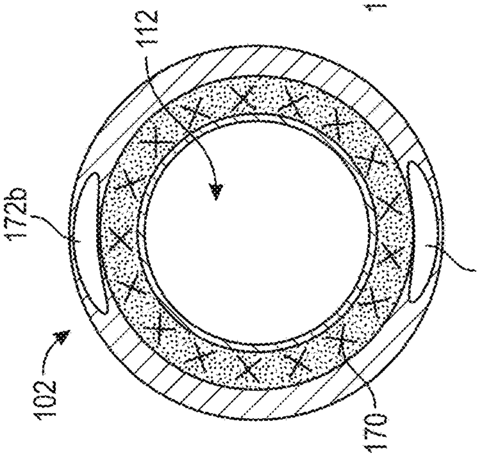
Figure 12C:
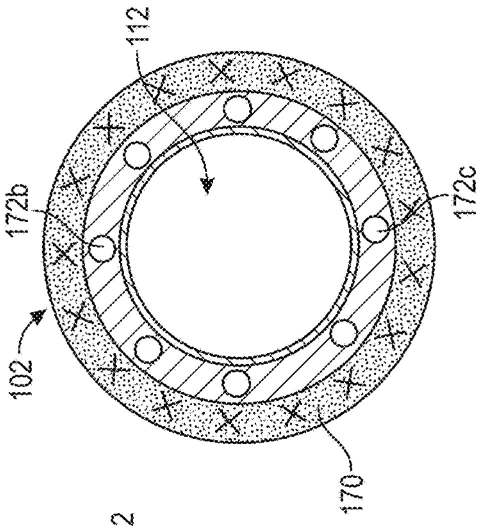

As illustrated in FIGS. 12A-12C, which are cross-sectional views of the shaft 102 taken along the lines indicated in FIG. 10, electrical conductors 170 which transfer power and signals back and forth between the imaging system and the transducer are routed in the annular space surrounding the lumen 112. The conductors 170 may be comprised a plurality of any combination of coax wires, solid or stranded core single conductors, twisted pairs, shield wires, or coax-like wires which may be conductors bundled with adjacent ground lines, or multi-filar wires arranged in ribbon-like configurations. The conductors 170 may also be provided on an elongated flex circuit. The conductors 170 may have additional lines for tensile and/or torsional strength, such as aramid fiber, stainless steel or nitinol in flattened or round profiles. Any combination of the above may be routed in any combination of straight, braided, or coiled (or may be provided in coiled or braided in differently layers) within the annular space around the central lumen 112.

Returning to FIG. 10, the handle 120 is attached to the proximal end of catheter shaft 102. The handle 120 is fitted with a port 126 that allows access to the lumen 112. Preferably the port 126 also includes a hemostasis valve (common on introducer sheaths, and known in the art), sized to seal on the shaft 152 of the steering catheter 150. The port 126 could alternatively house a Tuohy Borst style valve which can be opened and closed by rotating a knob around a seal. The electrical conductors 170, are routed out the proximal end of the handle 120 through an extension 128 to an electrical connector 129. A connector cable 130 has a distal catheter-side connector 131 configured to physically mate with and make an electrical connection to the catheter electrical connector 129. System-side connector 132 is configured to physically mate with and make an electrical connection to an imaging system 2000.

The lumen 112 may also be in fluid communication with an optional flush line 121*a*. The flush line 121*a* may be used to connect to a fluid source 125 containing fluid via a valve 122*a* and an extension line or tubing 123*a*. The fluid source 125 may be a pressurized bag to a drip line, peristaltic roller pump, or a more sophisticated dispenser of fluid (controlling volume, rate, pressure). The fluid may be used to provide lubrication within the lumen 112 for the steering catheter 150, or other devices which may pass inside the lumen (e.g., stylets, guidewires). The fluid may be physiologic saline, or contrast dye, particularly if exiting into the patient. However, if the fluid is contained within the catheter, and/or exiting only to the sterile field, the fluid could be a sterile lubricant and/or coolant not intended for internal use. In an alternative embodiment illustrated in FIG. 12B and FIG. 12C, fluid is supplied to the tip region 110 via lumen (or parallel groups of lumens) 172*b* independent of lumen 112. The fluid is routed around the transducer region to enhance cooling, and then returned to the proximal end. The fluid return may also be through a separate lumen (or parallel groups of lumens) 172*c*. In embodiments where the fluid is completely contained in lumens that do not exit to the sterile field, non-sterile fluid may be used. In other embodiments, fluid is provided through the dedicated lumen 172*b* and/or 172*c* and returned through the lumen 112, or provided via lumen 112 and returned via the dedicated lumen 172*b* and/or 172*c*. The dedicated lumens 172*b* and 172*c* have associated ports 122*b*/122*c*, valves 123*b*/123*c*, and fluid lines 124*b*/124*c*.

Figure 13A:
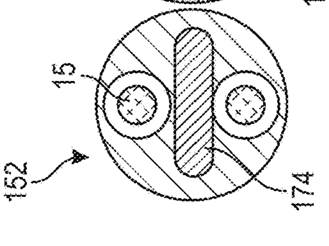
Figure 13B:
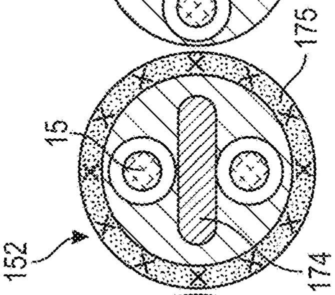
Figure 13C:
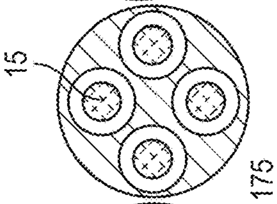
Figure 13D:
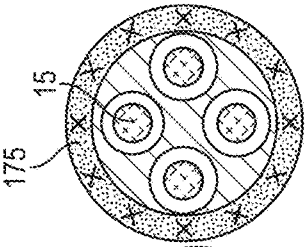
Figure 13E:
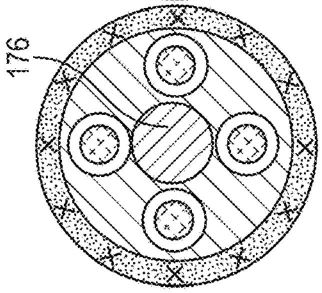
Figure 13F:
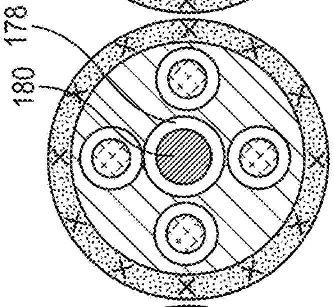
Figure 13G:
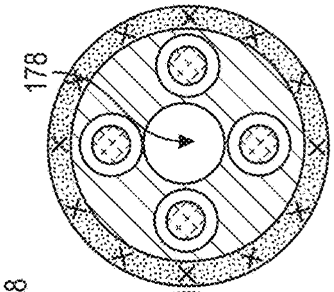

As illustrated in FIG. 10, the steering catheter 150 comprises a shaft 152 and a handle 161. The imaging catheter shaft 152 may be configured to be a single construction and stiffness, but preferably has three shaft sections, a proximal 154, mid 156, and distal shaft 158, with the transitions generally becoming more flexible toward the distal ends. Different models of the steering catheter 150 may be made available to the user with variations on the shaft stiffnesses depending on the use application. In general, as illustrated in section B-B in FIGS. 13A-13G, the handle 161 is used to operate pull lines 15 within the catheter 150. The pull line construction is similar to that described previously. Controls 162 and 164 (FIG. 10) may be used to apply and relax tension to the pull lines 15. One control may be used to deflect the catheter in one plane, and the other in a plane orthogonal to the first. Section B-B of FIG. 10 is illustrated in various construction embodiments in FIGS. 13A-13G. FIG. 13A shows catheter shaft 152 comprising a polymer material (e.g., Pebax of different durometer choices or polyethylene of a single low or high density type or blend of these) that contains one or more lumens inside through which pass a pull line 15. The lumens may be formed as part of the polymer extrusion and/or with the reflow of the polymer around removable mandrels. A lubricious liner for the lumen (e.g., PTFE) may also be present. The center of the catheter body 152 may include a flattened member 174 which creates a bending bias perpendicular to the flattened member (in the direction of the pull lines). The member 174 may be a polymeric extrusion or metallic (e.g., stainless steel or nitinol) material. The member 174 is preferably located within at least the distal shaft 158, but may extend though the entire length of the catheter 152. In other embodiments, the distal end of member 174 may be non-round and the proximal end round. FIG. 13B shows the embodiment of FIG. 13A with a braided structure 175 around the shaft that is laminated with a polymer similar to that previously described. The braided structure provides torsional strength and may be metallic wires or ribbons (e.g., stainless steel or nitinol), or high strength polymer fibers (e.g., aramid), or a combination of these. FIGS. 13C and 13D are similar to FIGS. 13A and 13B, respectively, but show four lumens and pull lines to provide orthogonal deflection capabilities. FIG. 13E illustrates the addition of central member 176 that is fused within the catheter shaft 152 that provides structural strength. The central member 176 may be continuous or selectively placed within the catheter shaft 152 to achieve different strength and stiffness characteristics. The construction of member 176 may also be different over the catheter length to achieve different strength and stiffness characteristics. The member 176 may be a substantially round polymeric extrusion or a metallic wire. The member 176 may be altered or tapered to a smaller diameter distally for enhanced flexibility distally. FIG. 13F illustrates the center of catheter body 152 formed into a lumen 178 containing a central member 180. The member 180 may be similar to member 176 but in this embodiment is not fused within the catheter shaft 152. In an alternative embodiment, the member 180 may be moveable and/or removable from the lumen 178 by an operator actuating it from a port on the proximal end of the catheter 150. FIG. 13G is similar to 13F but shows the catheter with just an open lumen 178 in the center. Placement of a member such as 180 is optional.

Figure 11:
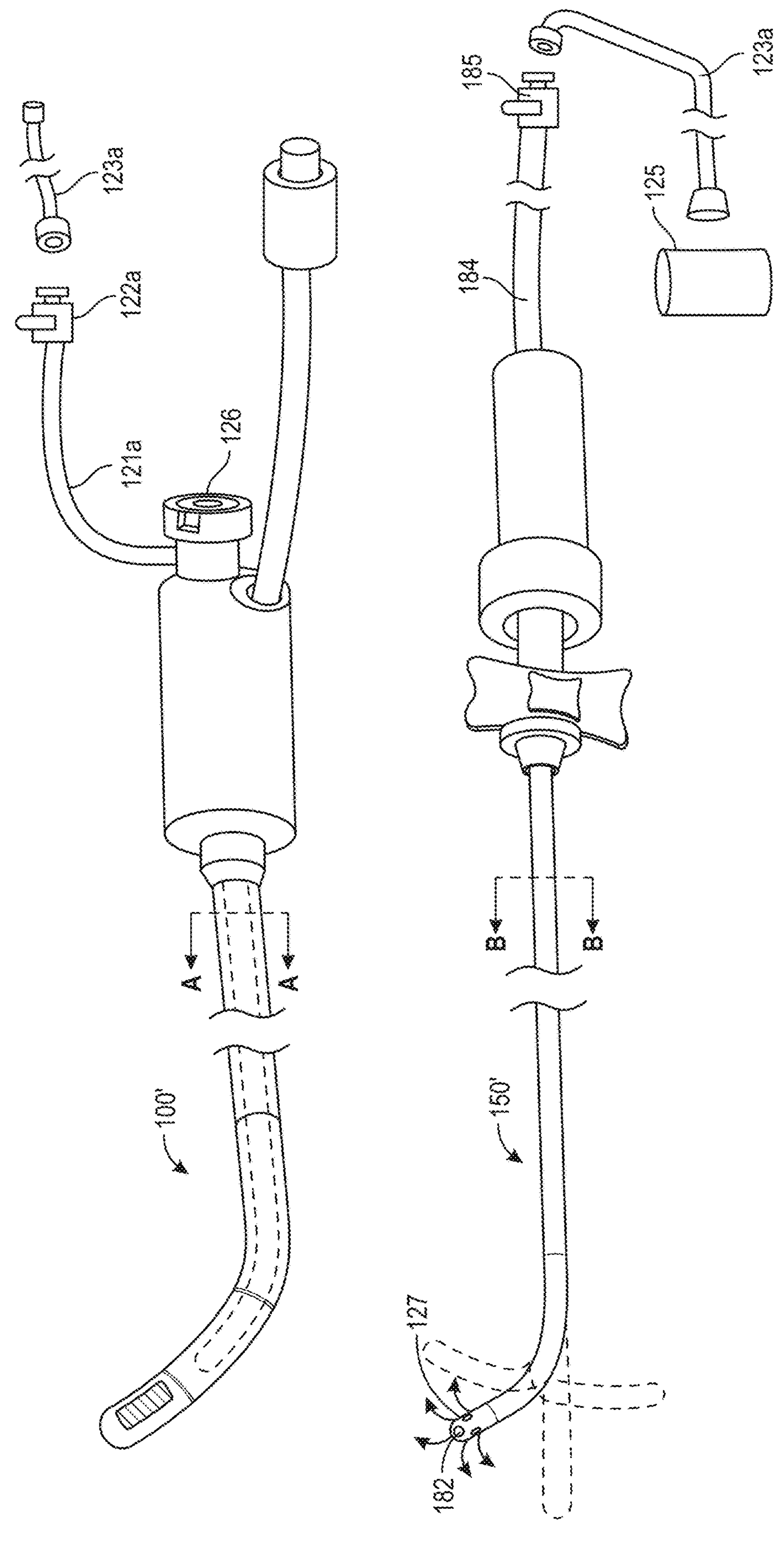

FIG. 11 shows an alternative configuration to FIG. 10. In this embodiment, delivery of fluid to the central lumen of the catheter 100' is provided through the catheter 150'. Preferably, the fluid is delivered to the catheter 100' via source 125, passes through extension tubing 123*a* and into catheter tubing extension 184 (fitted with valve 185), proceeds through central lumen 178 (FIGS. 13F and 13G), and exits the distal tip region 160 of the catheter 150' through ports 182 in communication with the central lumen 178. The proximal end of the catheter 150' could alternatively be fitted with a port 126 (with a valve) and side port/tubing 121*a*/122*a* similar to that on catheter 100'. When catheter 150' is placed within central lumen 112 of the catheter 100', the fluid exiting ports 182 travels proximally through catheter 100' where it exits port 126 or side port/tubing/valve 121*a*/122*a*. The fluid 127 may be disposed of or allowed to circulate back through source 125. In a specific embodiment as illustrated in section C-C in FIG. 14A, the distal region 160 (and possibly distal shaft section 158) of the catheter 150' is designed to fit under the transducer 115 in the distal section 108 of the catheter 100' (within the lumen 113). Thus, similar to that described for the embodiments of FIG. 10, the fluid used in the embodiments of FIG. 11 provides a similar purpose of lubrication of the lumen and/or cooling of transducer 115.

Referring collectively to FIGS. 10 and 11, during use, the operator may choose how far distally into the catheter 100 the catheter 150 is inserted. Steering catheter 150 may be deflected using the steering knobs 162 and/or 164 located on the handle 161. As a method of use, the steering catheter 150 may be inserted into the ICE catheter 100 prior to insertion of the ICE catheter 100 into the patient's anatomy. As the middle shaft 106 and distal shaft 108 of catheter 100 (or 100') are intended to be more flexible than when the catheter 150 (or 150') is inserted into it, the distance the catheter 150/150' is inserted can be influenced by how flexible the operator wants the catheter 100/100' to remain at the distal end, and how much distal steering is required. In another method of use, a shapeable stylet (similar to those used with pacing lead placement and known in the art) could be placed inside the catheter 100/100' at various insertion distances to aid in advancing the catheter within the patient anatomy.

In another method of use, the catheter could be configured as illustrated in FIGS. 14B and 14C to allow use with a guidewire. In this case a guidewire could be placed first and the catheter 100 (with or without the aid of dilator 200) tracked over it to a desired location. The guidewire (and dilator if present) could then be removed and the steerable catheter 150 inserted into the catheter 100 in its place to aid in further catheter manipulation.

Figure 14D:
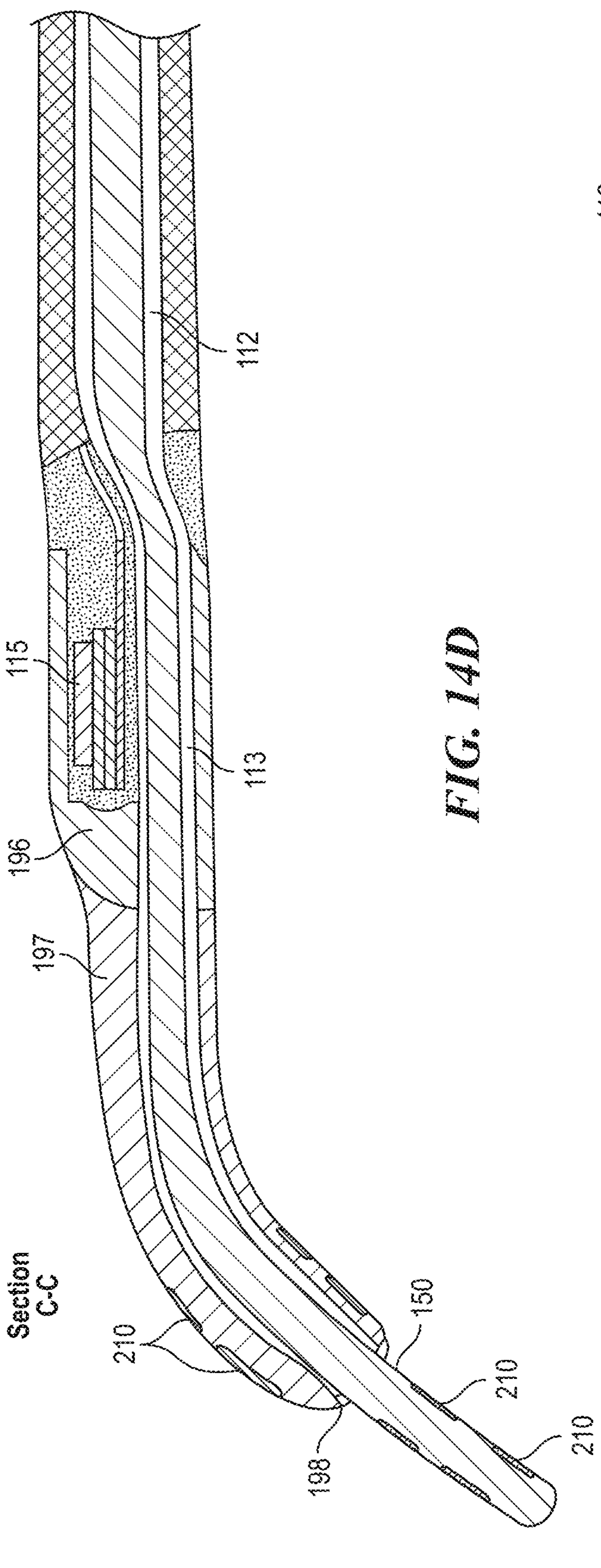
Figure 14E:
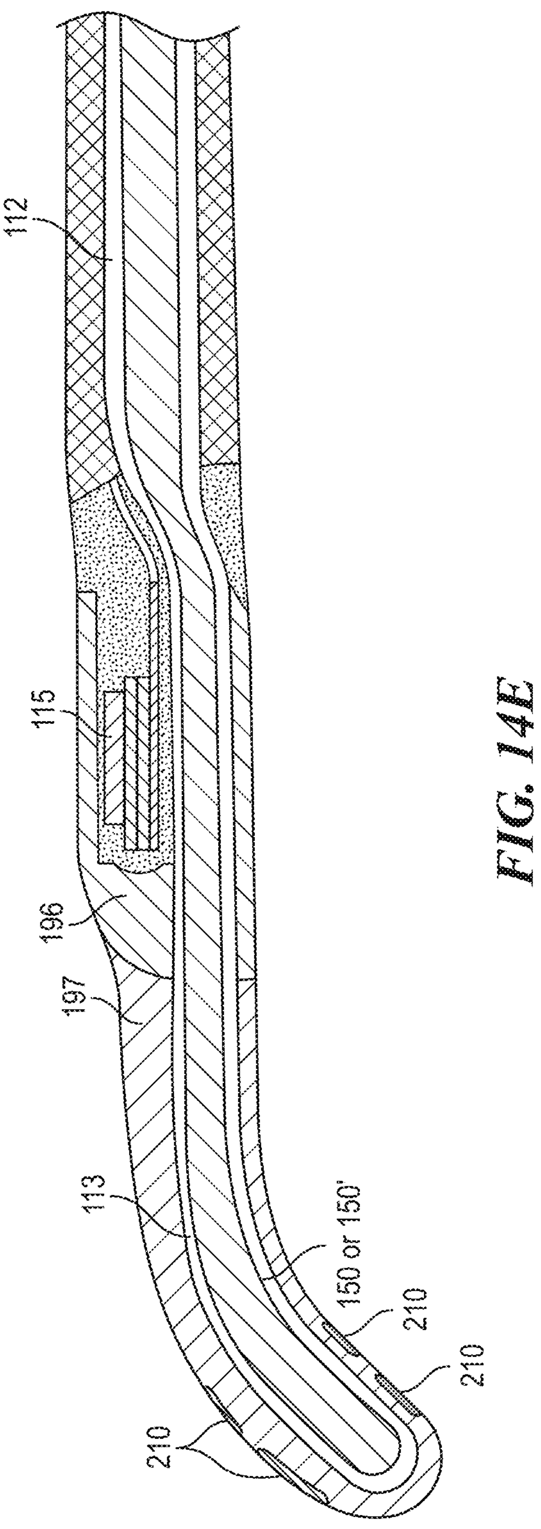

Another exemplary embodiment of catheter 100 section C-C is shown in FIG. 14D. In this case, a tip extension 197 is formed to be attached to the tip 196 (via adhesive bonding, polymer heat fusing, or internal wires/fibers, or any combination thereof) such that the relatively stiff tip region 110 around the transducer 115 of the catheter 100 has a transition distally to a more flexible material that can bend with a device placed inside of it. In this case, the intent is to advance the catheter 150 past the opening 198 to provide an alternative means of steering the catheter 100. The embodiment shown in FIG. 14E is similar to that of FIG. 14D except that the distal end of extension 197 is closed to contain any fluid introduced into the lumens 113 and 112. Thus, the catheter 150' could also be introduced to provide lubricating fluid to the lumen that can flow proximally through the distal extension, past the transducer (providing cooling as necessary), and out through the proximal end of the catheter 100'. To facilitate fluoroscopic visualization of the extension 197, the material could be loaded with an additive Barium Sulfate or Tungsten particles, or incorporate an imbedded bands, a coil or a braid of a radiopaque metal such as platinum, gold, or alloys thereof. The extension 197 could also be fitted with one or more sensors 210 connected to an external mapping system via conductors (not shown) routed through the catheter to a proximal connector. The sensors 210 could be electrodes in contact with the blood which when connected to an impedance measuring system, can provide localization of the tip in an electro-anatomical mapping system. The sensors 210 could also be imbedded electrical coils that work in a magnetic field of the patient can provide similar localization of the device in a similar mapping system.

In an alternative embodiment and method of use, the catheter 150' could be a conventional irrigated and steerable ablation catheter (and the lumen 112 sized to fit it) that is used to steer and irrigate the catheter 100'. The ablation catheter can be used for its intended purpose before and/or after being used to steer the ICE imaging catheter 100'. A similar use could be contemplated for a non-irrigated commercial steerable catheter used with the catheter 100.

It is noted that any of the disclosure from any of the examples and embodiments above may be integrated with any of the disclosure from any of the examples and embodiments below, and vice versa.

Figure 15B:
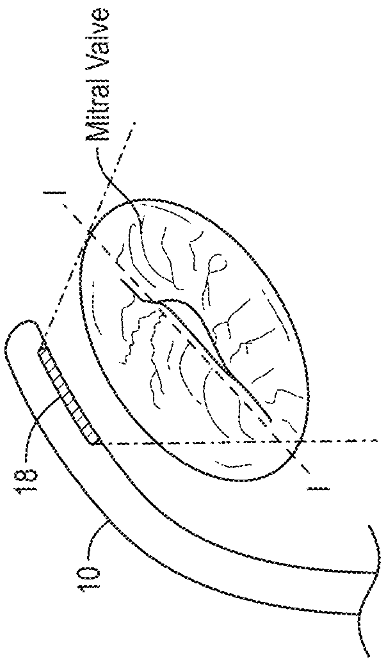
FIGS. 15A-15C illustrate imaging the mitral valve of a patient's heart using an ICE catheter and in accordance with embodiments of the present technology.
Figure 15C:
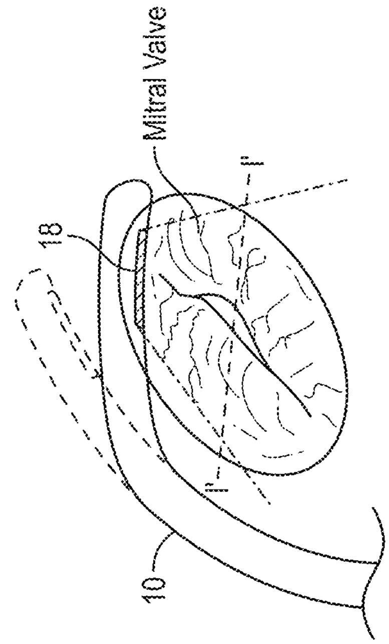
Figure 15A:
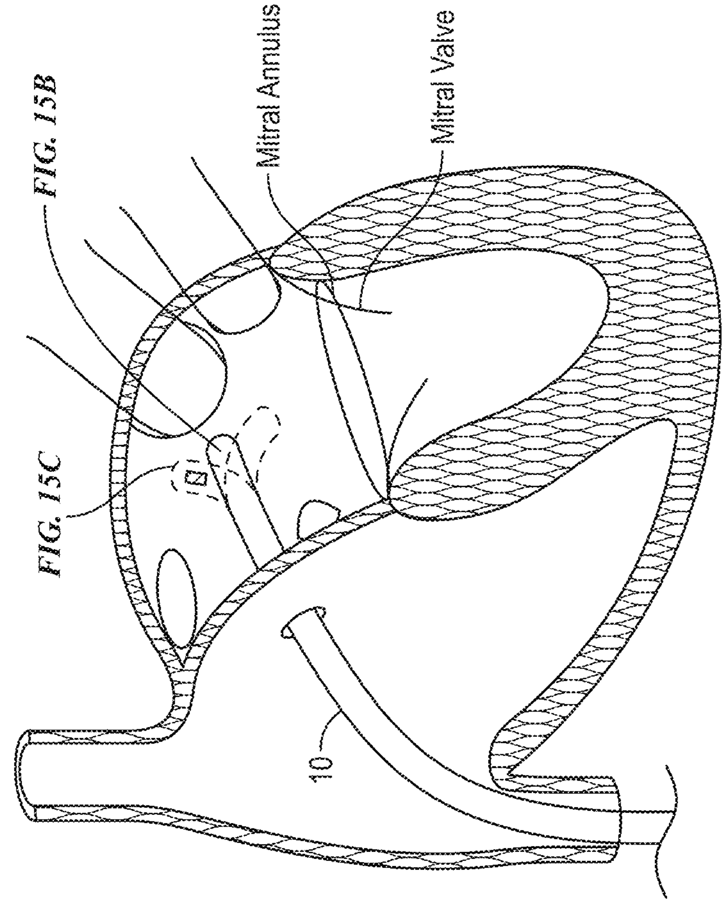
Figure 16B:
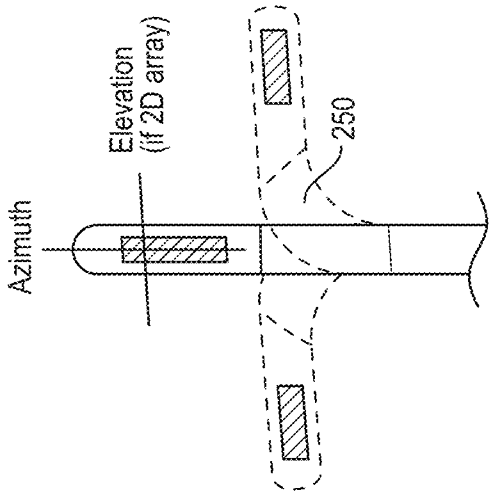
FIGS. 16A-17C illustrate an ICE catheter having a distal shaft hinge region and configured in accordance with embodiments of the present technology.
Figure 16A:
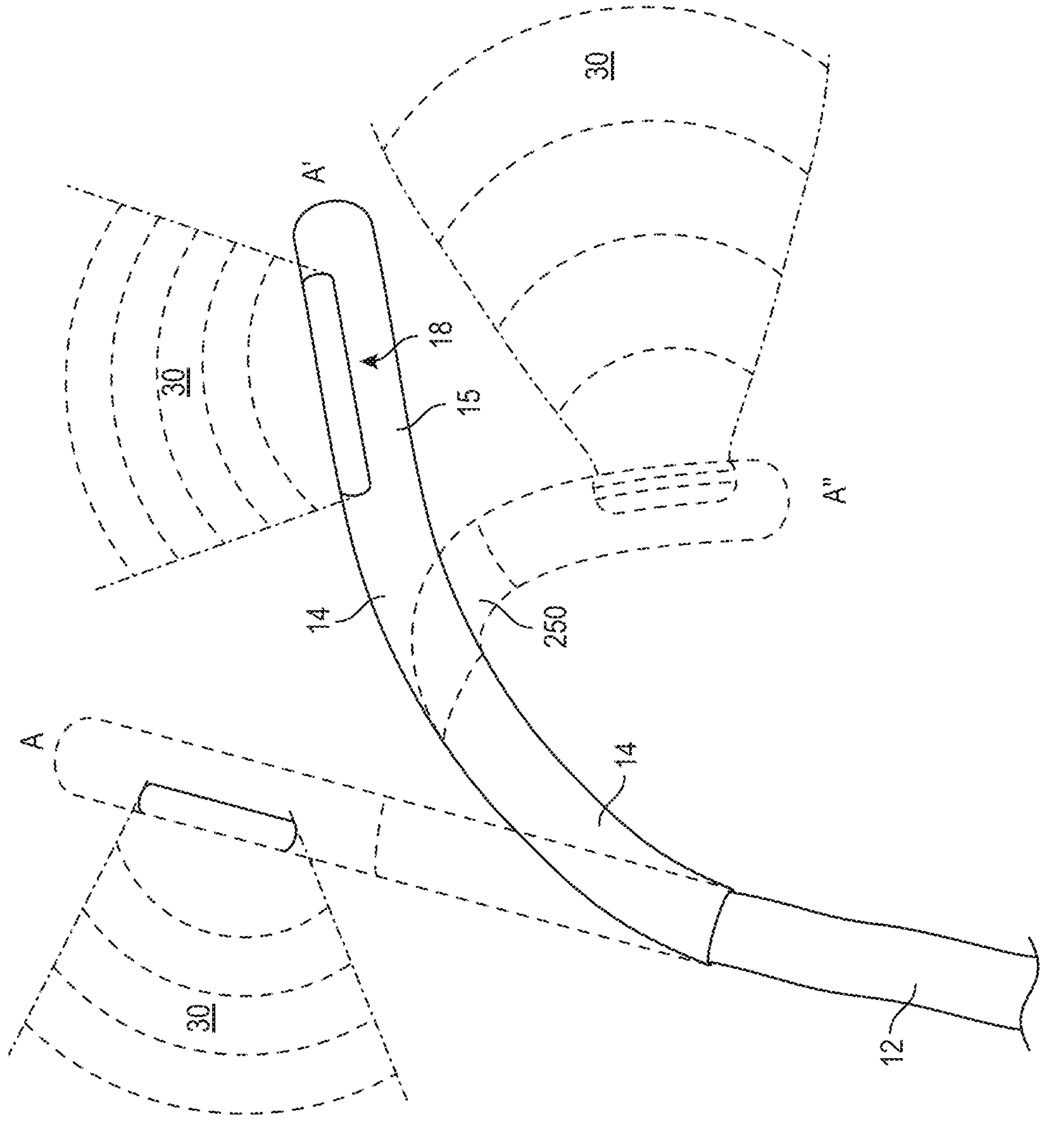
Figure 17B:
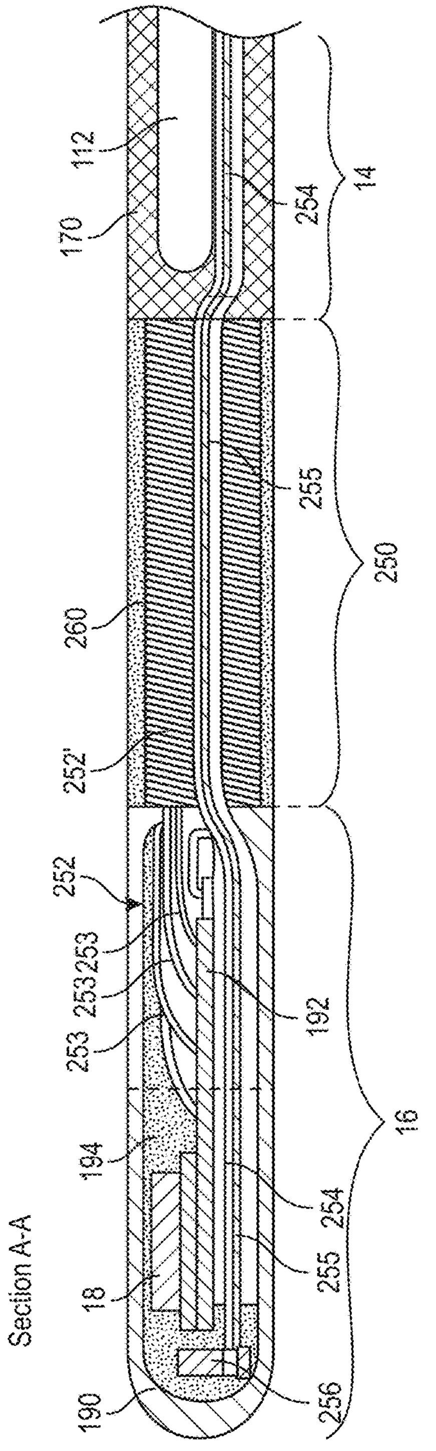

As noted previously, depending on the application, there may be a need for catheters with novel means to re-orient the transducer proximity to tissue independent of the sweeping deflection arc of the catheter, and to alter the azimuthal alignment of the transducer relative to the target tissue, also independent of the primary catheter deflection. FIGS. 15A and 15B illustrate such a need in the specific example of imaging the mitral valve from an ICE catheter 10 placed transeptally into the left atrium. The catheter 10 in the transseptal position is constrained to have an azimuthal orientation that is optimized for imaging plane I-I in FIG. 15B. However, for certain procedures, such as mitral valve clipping, the preferred imaging plane is I'-I' as shown in FIG. 15C. A need exists for a catheter which can change the azimuthal imaging plane from I-I to I'-I' easily during the procedure without substantially disrupting the transseptal position of the rest of the catheter 10. FIGS. 16A and 16B illustrate an example of how incorporation of a distal shaft hinge region 250 can provide a very tight radius curve that can reorient the azimuthal imaging plane of the transducer 18. FIGS. 17A and 17B provide more exemplary construction details for how a hinge 250 may be constructed. As shown in 17A, using the example of the catheter 10 from FIG. 2, the hinge section 250 is provided between the catheter distal deflection shaft 14 and the tip region 16. As illustrated in section A-A shown in FIG. 17B, within the tip region 16, the transducer 18 has electrical flex extension 192 to which a plurality of electrical conductors 252 are connected in a plurality of locations 253. The transducer 18 is contained within the tip material 190 and secured in place with adhesive or reflow material 194 (all of which has been described previously). The conductors 252 are routed as 252' in region 250 in a coiled and/or braided with a high picks/in count around the lumen 255 containing a pull line 254. The conductors 252' may be coiled or braided in a single layer, or may be formed in overlapping layers. Additional reinforcement structures (not shown) could also be added into the region 250. This includes wire or ribbons formed from stainless steel, nitinol, platinum-iridium, aramid fiber, or any combination thereof, formed into coils, braids, straight lines, or any combination thereof, in a single or multiple layers. The conductors 252 transition as part of routing 170 in shaft region 14 as previously described. Any reinforcement structures could be confined to the hinge region 250, or be continuous with similar reinforcement structures contemplated within the conductor routing 170. The shaft hinge region 250 is formed from the conductors 252' surrounded in a polymer 260, which is preferably a soft durometer material such as 35D pebax, and constructed to bend easier than the tip 16 or the shaft 14. The lumen 255 is preferably formed using a tubing such as PTFE, supported by a removable mandrel when potting or heat forming the material around it. The pull line 254 preferably extends under the transducer 18 where it is secured to an anchor 256. However, the pull line 254 could alternatively be secured at any point just distal to the shaft 250. While the pull line 254 is illustrated as being a single line routed under the transducer 18, which would deflect the transducer from A' to A" as illustrated in Fib 16A, the line 254 could alternatively be routed to the side of the transducer 18 to achieve a deflection similar to that illustrated in FIG. 16B. More than one pull line 254 could also be configured with different routing/anchor locations distal to region 250 to allow multiple deflection directions. The length of the shaft hinge region 250 may be 5-30 mm long, preferably about 10 mm, and deflectable to an angle of at least 90 degrees, preferably at least 120 degrees.

Figure 17C:
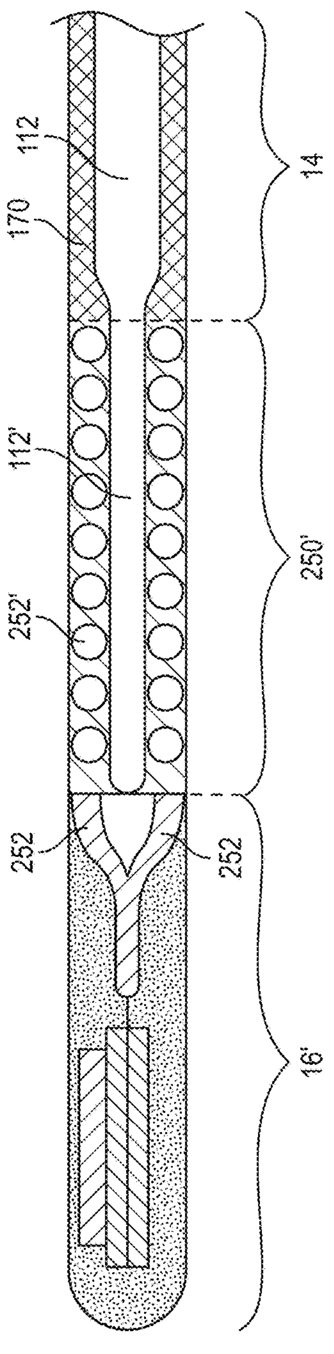
Figure 17A:
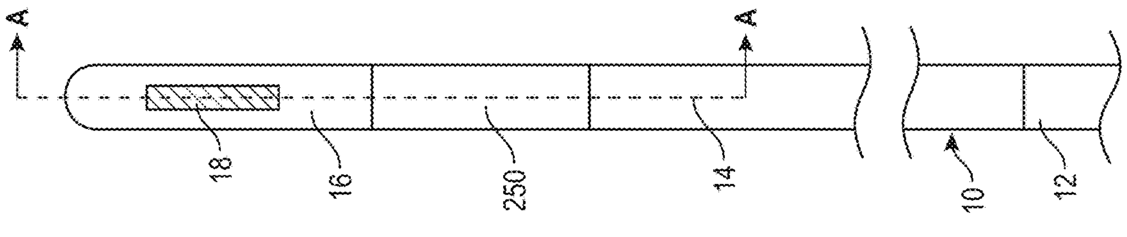

FIG. 17C illustrates an alternative embodiment of the hinge region 250, described as 250', in which the pull line 254 and the lumen 255 are replaced with the lumen 112' (an extension of lumen 112) that could be the same size or preferably smaller than the lumen 112. Similar to other embodiments, a shaped stylet and/or the catheter 150 or 150' could be configured to fit inside the lumens 112 and 112'. Catheter 150 or 150' could be fitted with a core wire (similar to 178 in FIG. 13F) that extends out the distal end of tip 160 of the catheter 150/150' and into lumen 112'. Preferably, the hinge region 250' is heat set into a desired alternative orientation (e.g., 90 degrees perpendicular to the original azimuth) but is held straight with the device placed inside the lumen 112'. Movement of a device in and out of the lumen 112' then changes the orientation as desired.

Figures 18A, 18B, 18C, 18D:
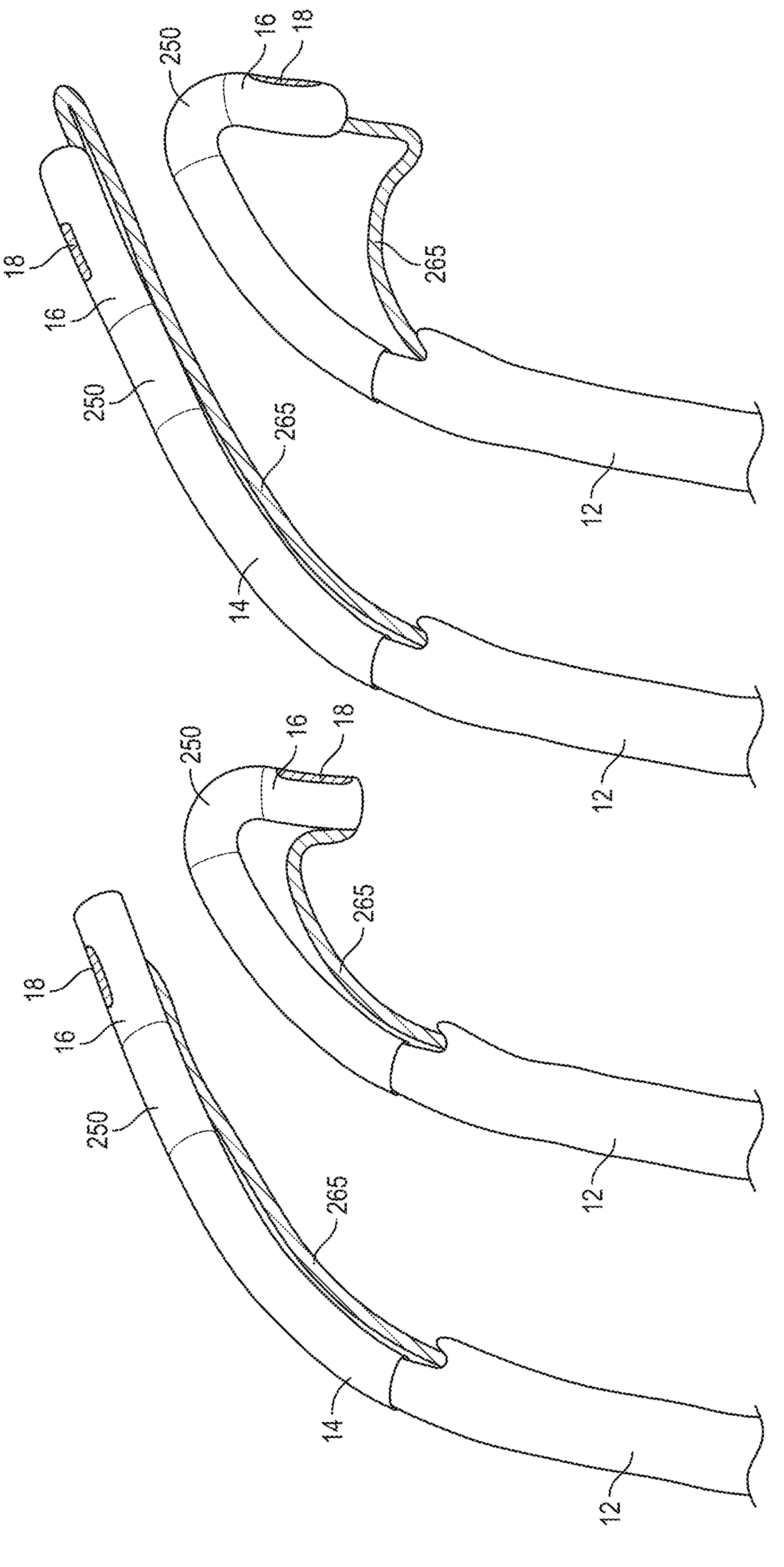
FIGS. 18A-18D illustrate additional embodiments of an ICE catheter having a distal hinge region and configured in accordance with embodiments of the present technology.

FIGS. 18A-18D illustrate other embodiments of how a hinge section 250 could be employed to achieve a tight bend. In FIG. 18A, a pull line 265 is routed externally from the shaft 12 to an anchor location on tip section 16, rather than being routed internally within the shaft 250. When tensioned, the catheter shaft 250 takes most of the bending and forms a tight radius. FIGS. 18C and 18D are similar to FIGS. 18A and 18B, except that the pull line 265 is alternatively attached externally to the distal end of the tip 16 (or anchored within the distal end of the tip 18 and extending out from the tip distally).

Figure 19A:
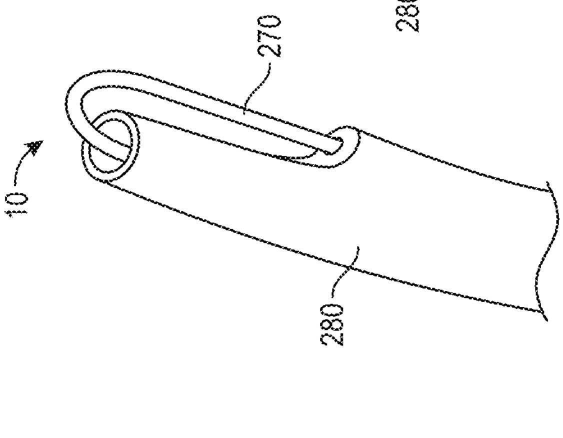
FIGS. 19A-19D illustrate additional embodiments of an ICE catheter having a distal hinge region and configured in accordance with embodiments of the present technology.
Figure 19B:
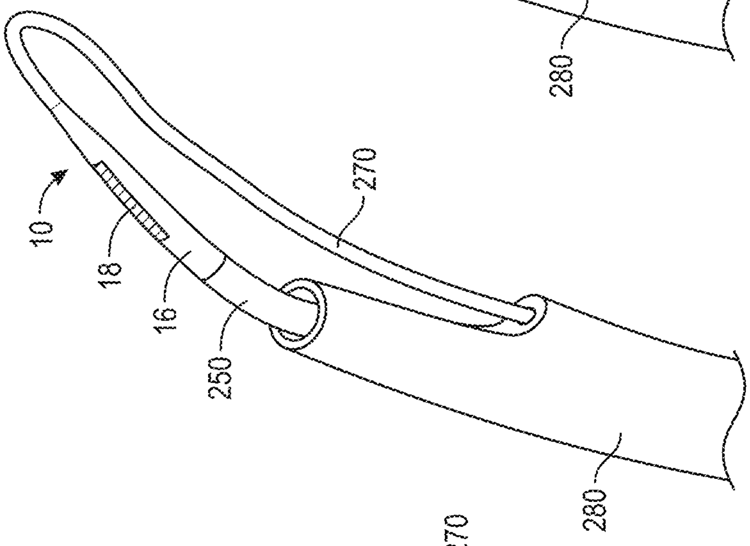
Figure 19C:
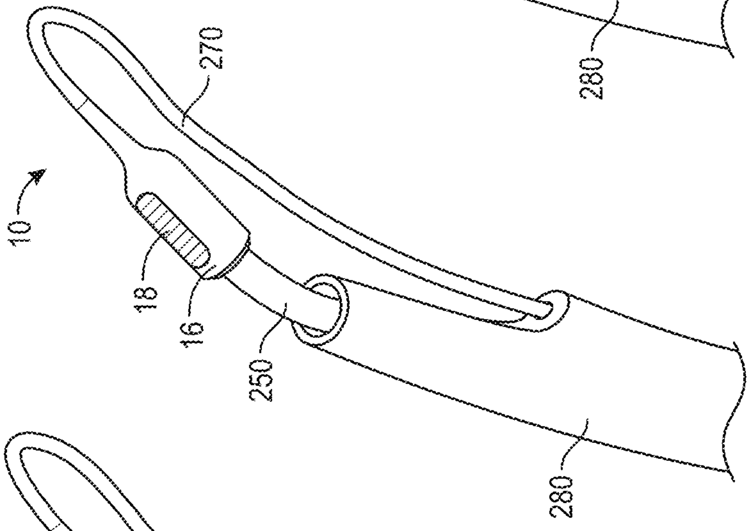
Figure 19D:
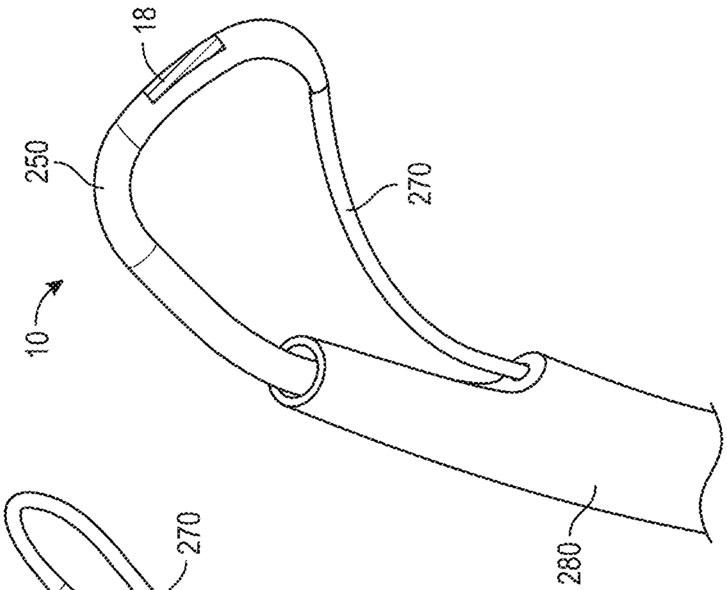

FIGS. 19A-19D illustrate another embodiment of how a hinge section 250 could be employed to achieve a tight bend. In this embodiment the main catheter body 280 houses the movable ICE catheter body (e.g., that of catheter 10) that is slidable within a lumen of catheter 280. A stabilization member 270 extends distally from the tip 16 (similar to that of FIGS. 18C and 18D) and routes back to another lumen (and/or anchor point) in the catheter 280. FIG. 19B illustrates the ICE catheter, inclusive of the tip region 16, being advanced distally from within the lumen of the catheter 280. FIG. 19C is an alternative embodiment where the tip region 16 is larger than the lumen within the catheter 280, and preferably the same outer diameter as the outer diameter of the catheter 280 where the ICE catheter exits. FIG. 19D illustrates the curvature achieved when tension is applied to the stabilization member 270 and the hinge section 250 takes a tight bend.

Figure 20A:
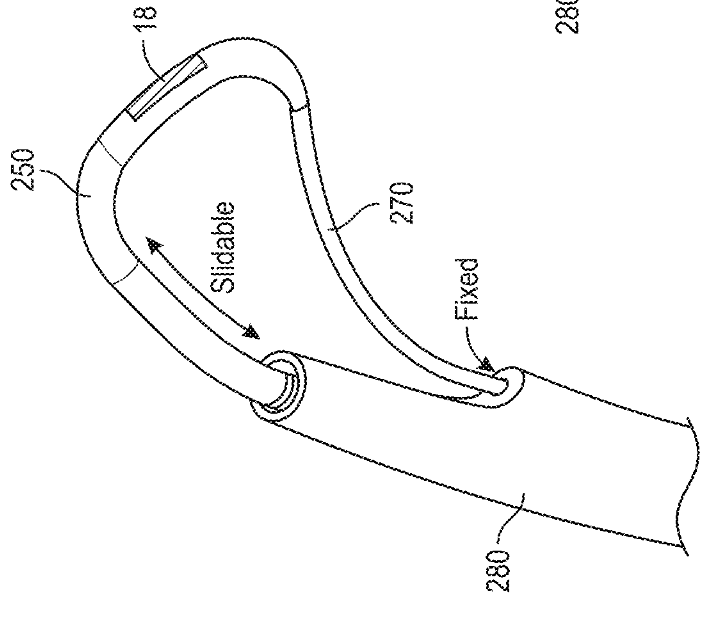
FIGS. 20A-20C illustrate additional embodiments of an ICE catheter having a sliding mechanism for changing an orientation of a transducer and configured in accordance with embodiments of the present technology.
Figure 20B:
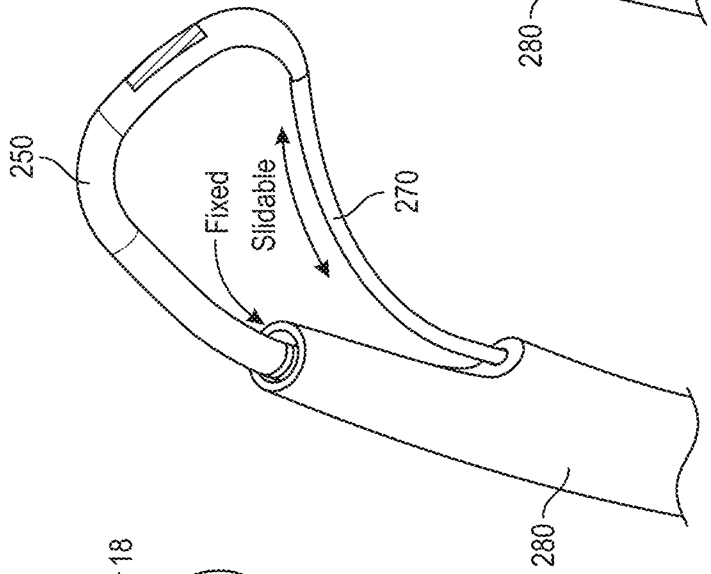
Figure 20C:
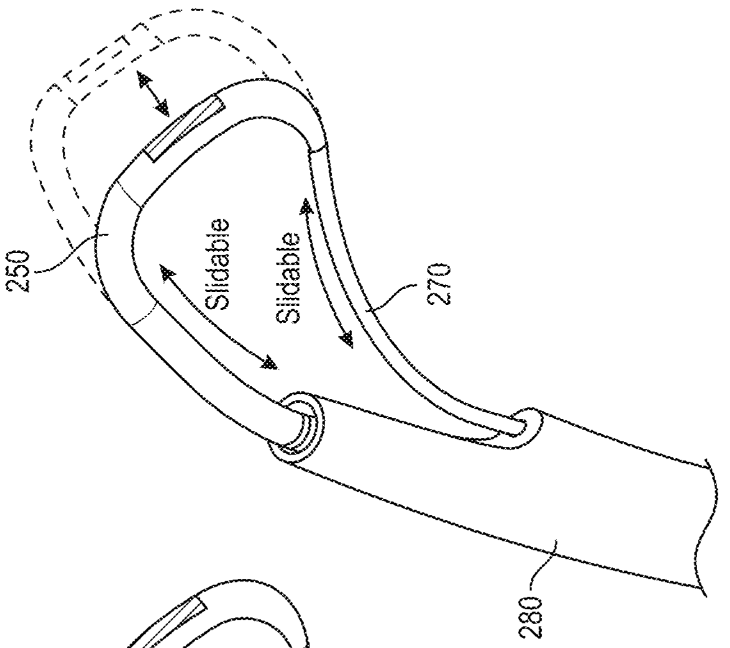

FIGS. 20A-20C illustrate different arrangement or means by which the transducer orientation change can be achieved. In FIG. 20A, the main ICE catheter body is axially slidable within a lumen of catheter 280. In FIG. 20B, the ICE catheter body is an extension of the catheter 280 and not slidable, but the stabilization member 270 is slidable. Stabilization member 270 in this case is constructed to be flexible but have enough compressive strength to transfer force to the tip of distal tip 16. In FIG. 20C, both the ICE catheter 10 and the pull line 270 are configured to be slidable in both directions. Simultaneous advancement/withdrawal allows a unique ability to translate the transducer 18 relative to the catheter body 280. The catheter body 280 may also be configured to be deflectable independent of the ICE catheter. While FIG. 19A-20C illustrate the stabilization member 270 exiting from a lumen or attachment point proximal to the exit of the ICE catheter 10, the exit point could be at the same location or even distal to the exit point of the ICE catheter 10.

Figure 21A:
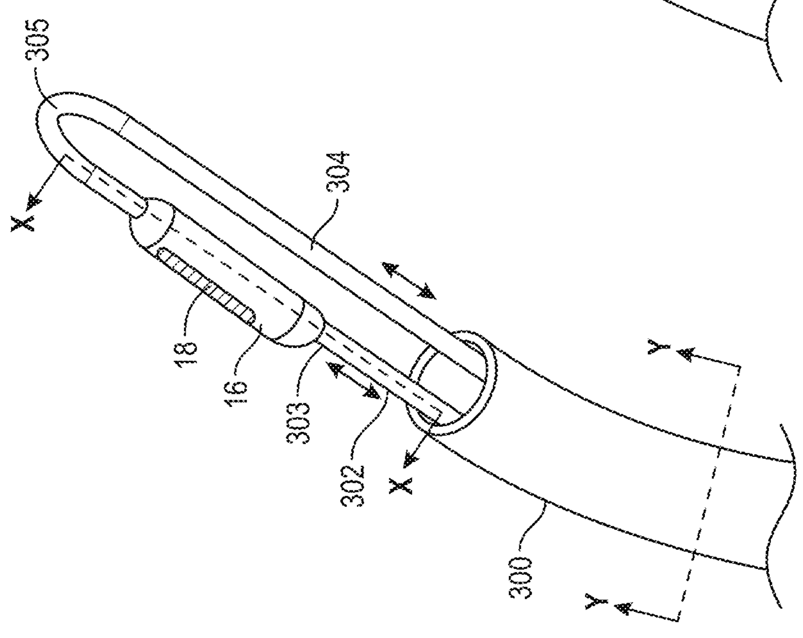
FIGS. 21A-21C illustrate additional embodiments of an ICE catheter having a mechanism for changing an orientation of a transducer and configured in accordance with embodiments of the present technology.
Figure 21B:
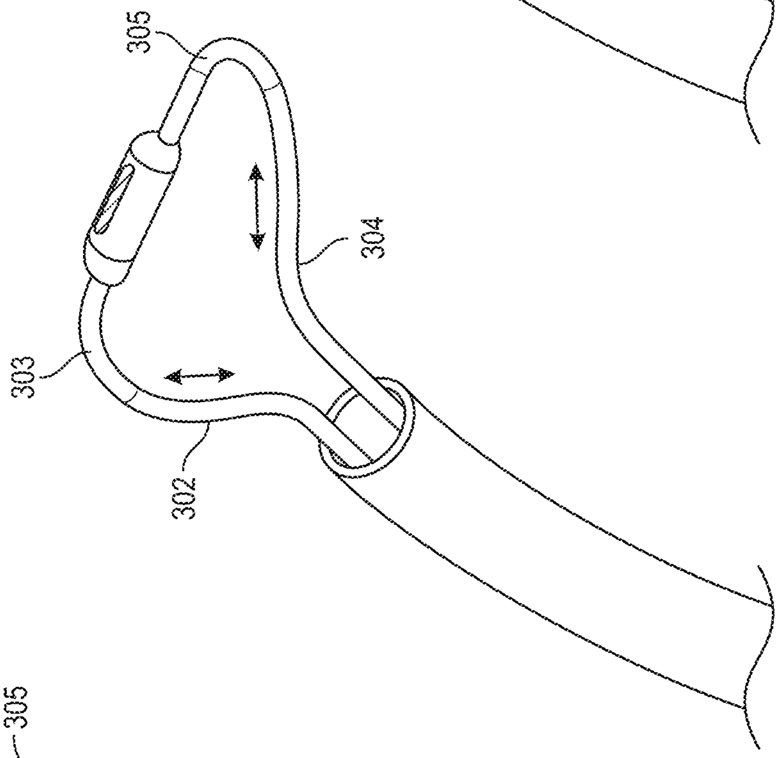
Figure 21C:
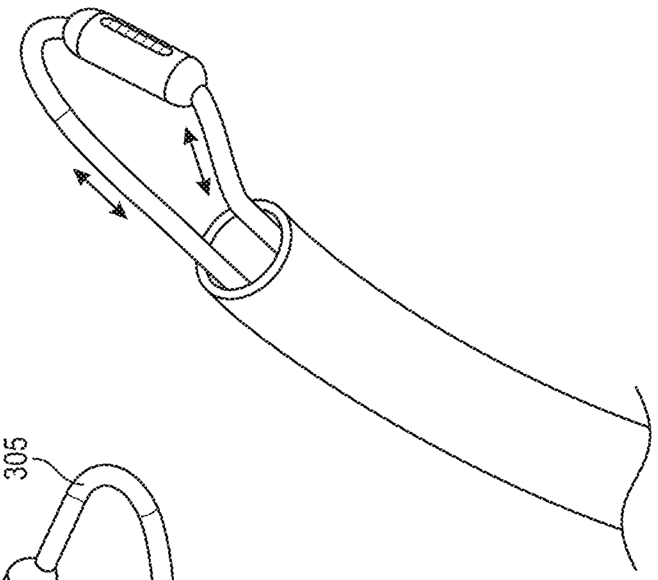

FIGS. 21A-21C illustrate another embodiment where the transducer 18 is housed in the tip region 16 that is connected to two support shafts 302 and 304 with flexible hinge regions 303 and 305. In some embodiments, the hinge regions 303 and 305 are equivalent to that previously described for the hinge section 250. The shaft/hinge 302/303 and 304/305 can be essentially identical, mirroring one another on each side of the transducer 18. This provides the advantage of fewer conductors required to be routed within a given shaft (302 or 304), so that both can be made smaller, and the same size, so as to facilitate both signal line routing and mechanical manipulation in an acceptably sized shaft body 300. As both the shafts 302 and 304 are slidable (either independently or together) within the lumen of shaft 300, the transducer orientation (and associated azimuthal imaging plane) can sweep an arc of at least 180 degrees (from FIG. 21A to 21C). Similar to FIG. 20C, the transducer may also be translated forward and back relative to the shaft 300.

Figure 22:
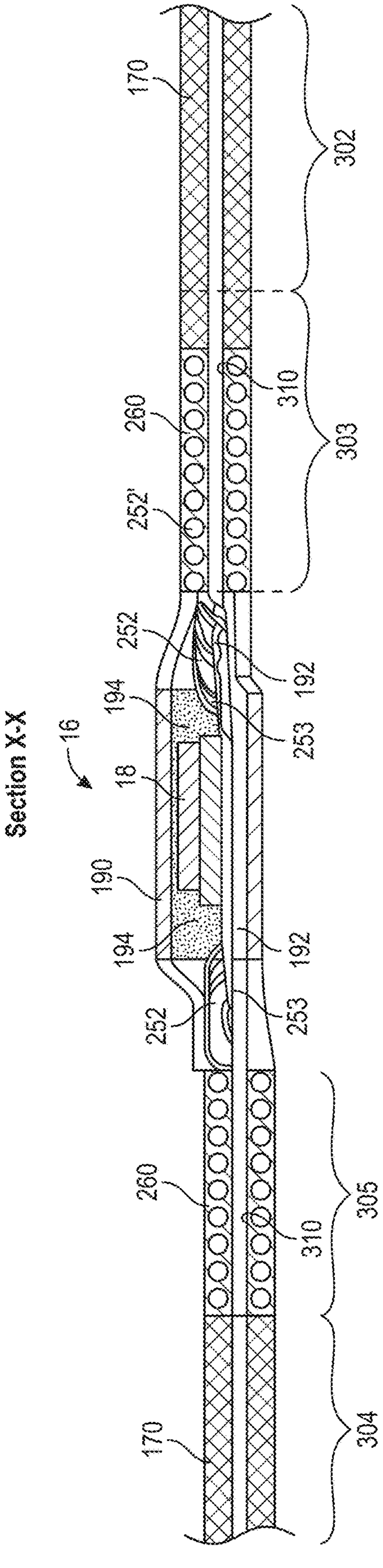
FIG. 22 is a cross-sectional view of the ICE catheter shown in FIG. 21A taken along the line X-X.

FIG. 22 illustrates section X-X taken along the lines indicated in FIG. 21A for further constructional detail. Similar to that shown in FIG. 17B, the transducer tip region 16 is formed by transducer 18 inside the tip 190 and bonded/fused with a material 194. The flex 192 extending from the transducer 18 in this case may extend from both ends of the transducer 18. Conductors 252 are attached at locations 253 on the flex. Similar to that described for FIG. 17B, the conductors 252, when routed into hinge regions 303 and 305 are designated 252', and then 170 in regions 302 and 304. Of note, a central space 310 may be formed as the conductors 252' are routed. This may be filled with a reinforcement member such as round or flat stainless steel or nitinol, or a braid of similar material or a braid of aramid fibers, or equivalent high tensile fiber structures. The reinforcement member could be anchored distal and proximal of the tip region 16, and/or extend proximally away from the transducer back through the main shafts (e.g., 302/304) to the proximal end of the device.

Figure 23B:
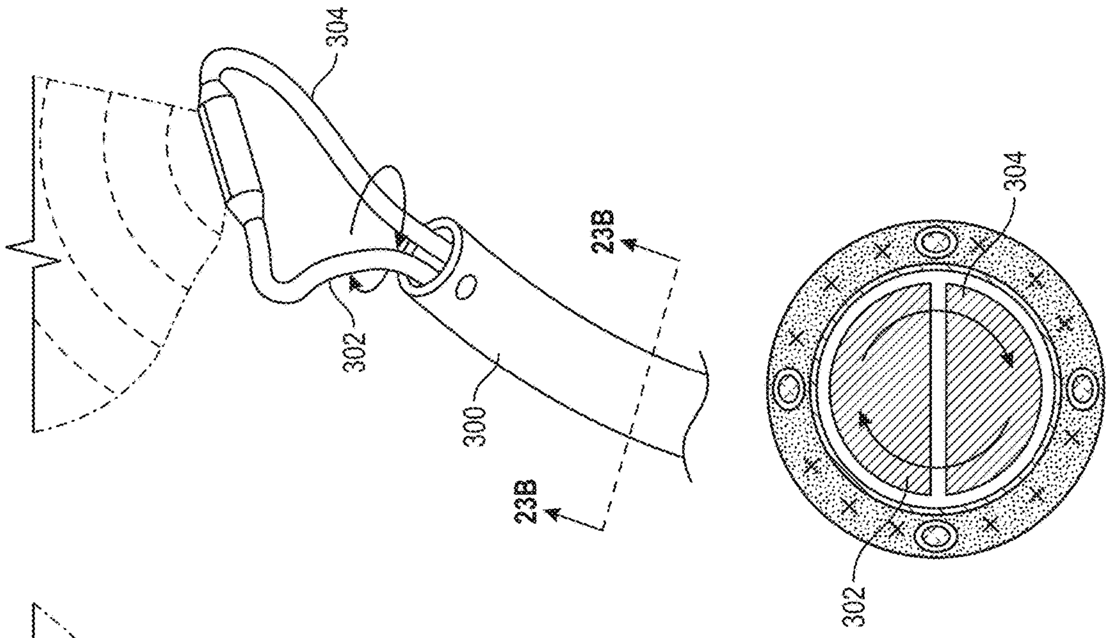
FIGS. 23A and 23B illustrate another ICE catheter having a mechanism for changing an orientation of a transducer and configured in accordance with embodiments of the present technology.
Figure 23A:
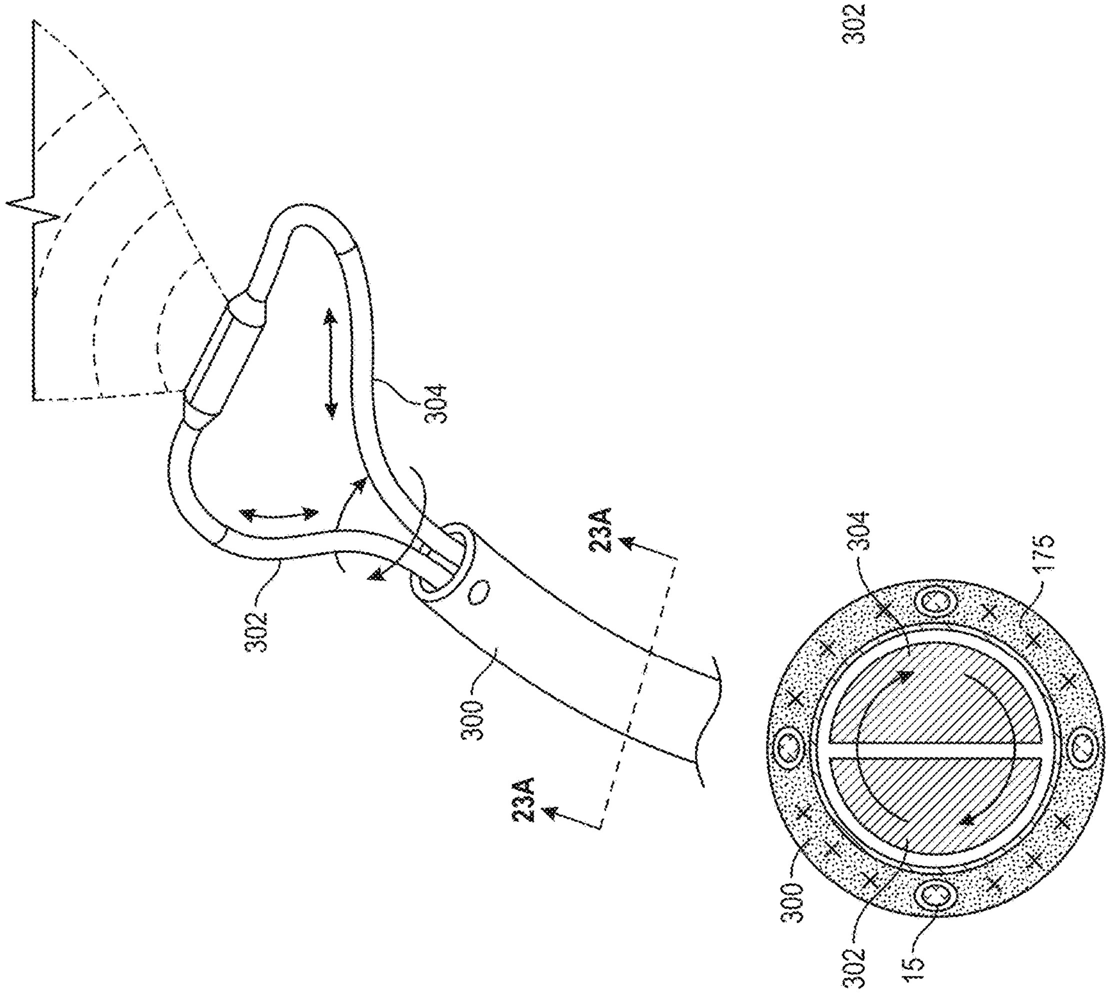

FIGS. 23A and 23B illustrate an embodiment where the shafts 302 and 304 are "D" shaped (cross sectional outer profile configuration, as illustrated in FIGS. 23A and 23B) and held within the lumen of the shaft 300. Both shafts are intended to be slidable proximally and distally (axially), but when rotated together from a proximal location, will transmit torque to one another, and because they are constrained by the lumen of the catheter 300, will not wrap up on one another. The torque transmission then allows the transducer region outside of shaft 300 to rotate to alter the preferred azimuthal imaging plane. Similar to construction of other torqueable and deflectable shafts, the shaft 300 may incorporate one or more pull lines 15 within lumens in the wall which is preferably formed of a polymer (e.g. Pebax of varying durometers) reinforced with braided strands 175. The inner lumen of the shaft 300 is preferably formed of a lubricious polymer such as PTFE and the lumen lubricated with a saline similar to that described previously. The "D" shaped shaft over a at least a portion of the length could be further defined by a "D" shaped stainless steel or nitinol hypotube which contained within it the electrical conductors. In other embodiments, the "D" shape could alternatively be an oval shape or 2-3 round tubular structures bound together. The "D" shape is an example of first and second outer shaft configurations or profiles that are each configured to interface with the other and transmit torque to one another when rotated together from a proximal location (e.g., a handle).

The operator may use a handle that includes a single knob to actuate shafts 302 and 304 in opposite directions to achieve the movement from FIG. 21A-21C. This may be, for example, a knob actuator having internal threads that engage with two interior sliding members having opposite external threads, with each sliding member coupled to a given shaft 302 or 304. Alternatively, a pully system could be employed on one side to direct motion in different directions. Rotational cams of opposite offset points could also be used the spit the movement direction. Preferably, any of these mechanisms could have a feature that allows an override to drive both the shaft 302 and 304 in the same directions (e.g., to achieve the motion illustrated in FIG. 20C). A separate deflection mechanism similar to that illustrated for the handle 161 in FIG. 10, having actuators 164 and 162 for 4-way steering, or just one of the two actuators for 2-way steering.

Figure 24:
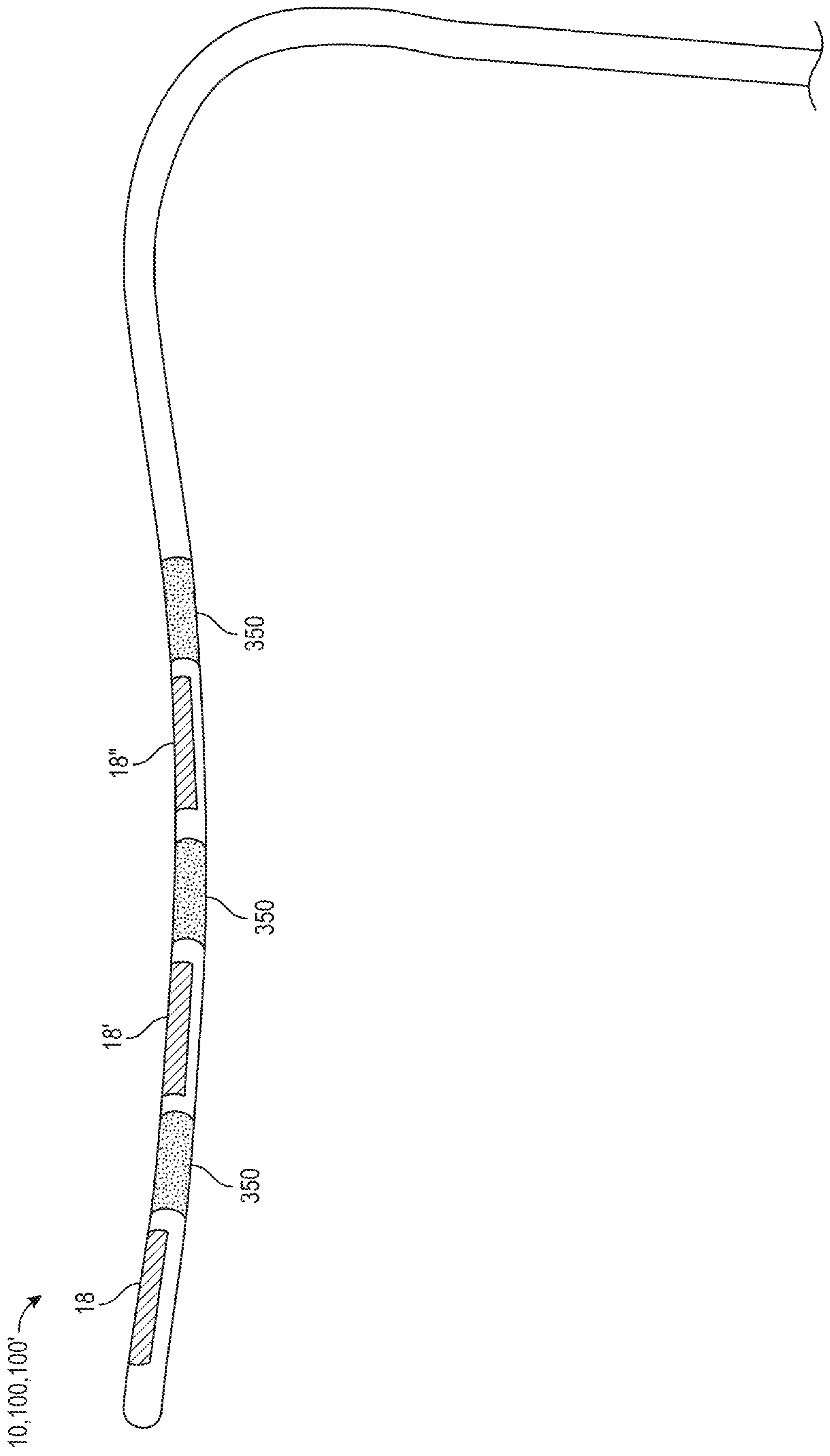
FIG. 24 illustrates an ICE catheter having a plurality of transducers and configured in accordance with embodiments of the present technology.

A current limitation to the length of an imaging transducer 18 (such as any of the transducers 18 herein) is that it may make the distal end stiff for too long of a length such that it becomes difficult and dangerous for an operator to steer the device in the heart. FIG. 24 illustrates an alternative embodiment to the previously described ICE catheters 10, 100, and 100' where a plurality of imaging transducers 18 (18', 18", etc.), each substantially elongated in that the length is at least 2 times the width, are positioned on the distal end of the catheter. Each of the elongated transducers are spaced over a given length, with flexible regions 350 provided to allow the distal shaft to have sufficient flexibility for steering into the anatomy as described in FIGS. 1, 3, and 4. The flexible regions could be made in a variety of techniques, and more specifically using the embodiments illustrated in the previous FIGS. in regions such as 250, 250', 303, and 305. The imaging system 2000 could be configured to rapidly scan through all the elements of each imaging transducer as done for other phased arrays, with some accounting for the space between the transducers when processing a single image. The system could also switch between images from a given transducer to provide the field of view of interest. Each transducer could be the length of any given transducer on the market (e.g., for a 1-D array, 64 elements long), or have each be slightly shorter for optimized catheter maneuverability and cost, but the total array length being greater than possible on the market today (e.g., 128 elements divided into 4×32 element lengths, or 3×42 element lengths).

In addition to the catheter constructions described with reference to FIGS. 5-24, the present technology further includes modular, compact, distributed, and/or otherwise modified ICE ultrasound assemblies/imaging systems. For example, as described with reference to FIGS. 25-27AB, the ultrasound assemblies described herein can be configured as a module of another system. In such embodiments, the ultrasound assembly still includes many features of conventional ultrasound imaging systems, such as high voltage signal transmit pulsers (e.g., up to 100V; preferably 20-60V), an Analog Front End containing Analog-Digital circuitry and FPGA (field programmable gate arrays) for beamforming, means to measure and control power and temperature, and the like. However, in various embodiments, such as described in detail with reference to FIGS. 25 and 26, the ultrasound assemblies can be designed to share/leverage certain features with other systems typically found in a catheter lab setting. Examples of shared features can include a shared processor and other computing architecture, a shared user interface (UI), a shared display, and the like. And, in various embodiments, such as described in detail with reference to FIGS. 27A-28F, certain select components of the ultrasound assembly can be positioned in a separate, compact housing that in use is positioned near the ICE catheter itself. As described in greater detail below, these modular, compact, and/or otherwise modified ICE ultrasound assemblies are expected to provide several advantages over conventional ICE ultrasound assemblies.

Figure 25:
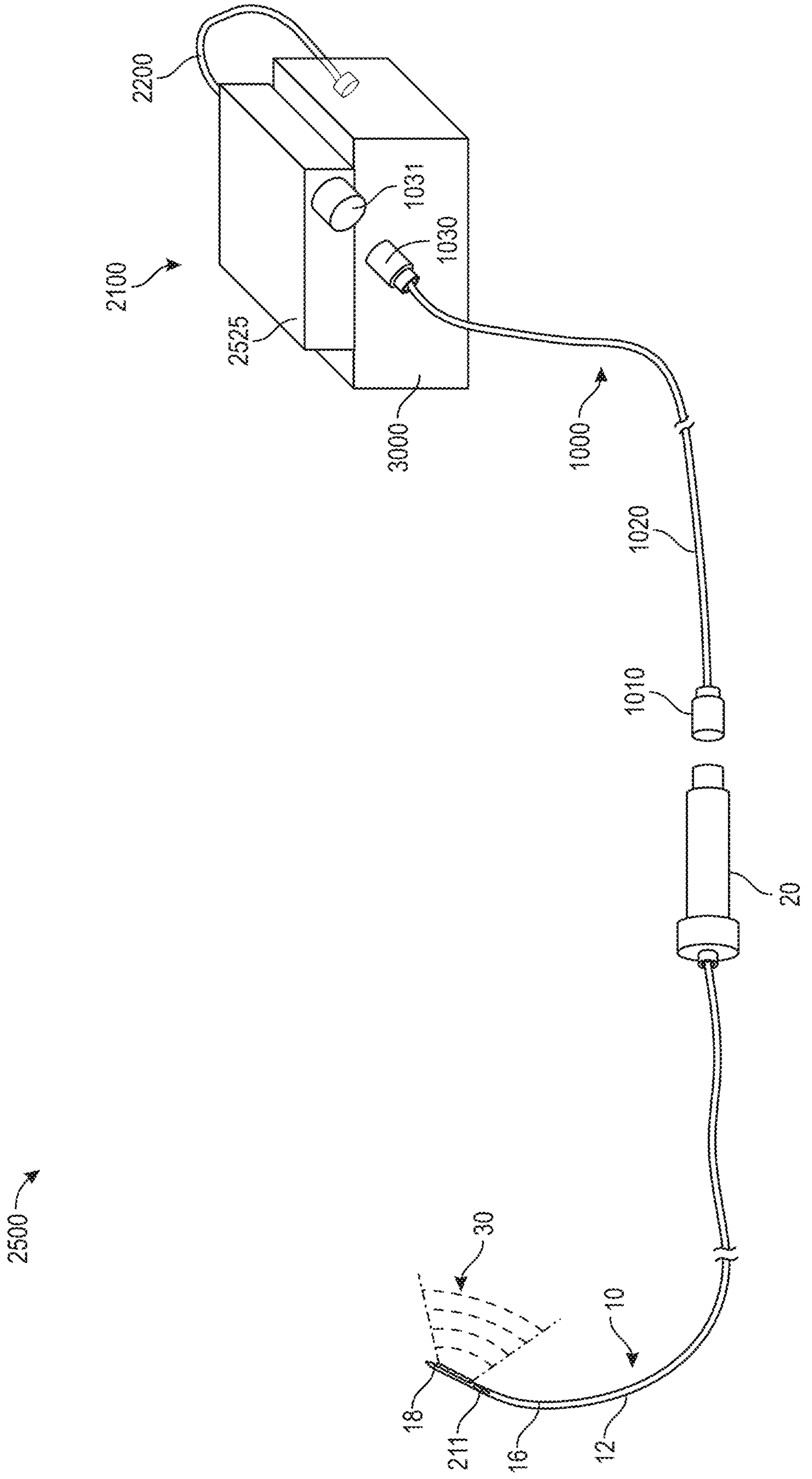
FIG. 25 illustrates an ICE system having an ICE catheter and an ultrasound assembly configured in accordance with embodiments of the present technology.

For example, FIG. 25 illustrates a distributed intracardiac echocardiography system 2500 configured in accordance with embodiments of the present technology. The ICE system 2500 can include an ICE catheter 10 and an ultrasound module or assembly 2100. The ICE catheter 10 can be generally similar to or the same as any of the ICE catheters described throughout this Detailed Description. For example, the ICE catheter 10 can include a handle 20, a shaft 12, and a transducer tip region 16 having an imaging transducer 18 for generating an ultrasonic field 30. The transducer 18 can have any number of elements suitable for ICE procedures, such as between about 32 and about 128 elements, or between about 64 and about 96 elements, or between about 64 and about 88 elements, or about 64 elements. In some embodiments, the number of elements can be selected to balance between image quality and catheter size. The elements can be arranged in a one-dimensional linear array or other suitable configuration for ICE procedures.

The shaft 12 can have a diameter suitable for ICE procedures, such as between about 6 French and about 14 French, or between about 7 French and 11 French, or between about 8 French and about 10 French, or about 9 French. As one skilled in the art will appreciate, the size of the shaft 12 is typically a tradeoff between the cabling required to support the intended operation of the catheter, and the intravascular route the catheter must navigate. The size of the shaft 12 can also be based at least in part on the size of the transducer 18, which can be based on, among other things, the number of elements as set forth previously. The size of the transducer 18 can dictate the diameter of the transducer tip region 16, which itself generally matches the diameter of the shaft 12. For example, a relatively larger transducer allows for a larger aperture which generally provides better image resolution, while a relatively smaller shaft diameter allows the use of a smaller vascular access sheath (not shown) and in general allows the catheter shaft to be more maneuverable. In the context of ICE, the foregoing ranges represent the balance between enabling ultrasound abilities with the catheter and enabling the intravascular navigation of the catheter into the heart.

Additional clinical or procedural requirements may further dictate the size of the shaft 12. Generally, the vascular access sheath is placed in the groin for access to the femoral vein leading up to the inferior femoral vein that enters the right chambers of the heart. In some procedures, the same vascular access sheath is used for therapeutic catheters, although in other procedures a separate vascular access sheath can be placed in the femoral vein on the other side, such that there are vascular access sheaths in both the left and right femoral vein. In yet other procedures, two vascular access sheaths are placed into the same vein on the same side (e.g., right or left). In this case, having a smaller vascular access sheath for the ICE catheter can provide a better fit for both, particularly where larger therapeutic access sheaths are required (e.g., those required for certain ablation catheters, left atrial appendage occlusion devices, or valve repair/replacement devices). Similarly, when accessing the left atrium with these devices via an atrial transseptal puncture, the catheters may be placed alongside one another in the transseptal access hole. In this case, a smaller ICE catheter will reduce the expansion of the transseptal hole.

The ICE system 2500 further includes an ultrasound console or assembly 2100. The ultrasound assembly 2100 can include a housing 2525 with various imaging related features positioned therein, such as an Analog Front End, other beam-forming components (e.g., FPGAs, transmit and receive beamformers, etc.), electronics for controlling the AFE 2722 or other beam-forming components (e.g., transmit and receive electronics), a mixer, one or more fans, a processor, memory, and the like. The ultrasound assembly 2100 can be connected to the ICE catheter 10 via a cable 1000. Specifically, the cable 1000 includes a catheter-side connector 1010, a cable body 1020, and system-side connector 1030. In some embodiments, the cable 1020 can be between about 10 feet and about 20 feet long in order to reach from the patient table to the equipment rack and/or ultrasound assembly 2100 in the catheter lab. The ultrasound assembly 2100 can send analog signals to the transducer 18 via the shaft 12, and the transducer can convert the analog signal into acoustic waves 30 which are sent and received by the transducer 18.

In some embodiments, the housing 2525 (and thus the ultrasound assembly 2100) does not include a dedicated user interface and/or a display. Instead, the ultrasound assembly 2100 can be connected to another computing system 3000 via a physical connection 2200 (e.g., USB 3.x or faster or LAN ethernet cable, as well as power if required separately from USB provided power). In such embodiments, the ultrasound assembly 2100 may utilize (e.g., share) certain components within the computing system 3000, such as a user interface (e.g., controls) (not shown), a display (not shown), computing architecture, and/or a power supply. For example, in some embodiments one or more software modules associated with the ultrasound assembly 2100 (e.g., an image processing unit, a control unit, etc.) may be incorporated into the computing architecture of the computing system 3000, rather than into the computing architecture included in the housing 2525. Additionally or alternatively, a user can interact with a single set of controls or displays when operating both the computing system 3000 and the ultrasound assembly 2100. In some embodiments, the computing system 3000 can be another system commonly found in catheter labs, such as an electrophysiology mapping system ("EPMS").

Figure 26:
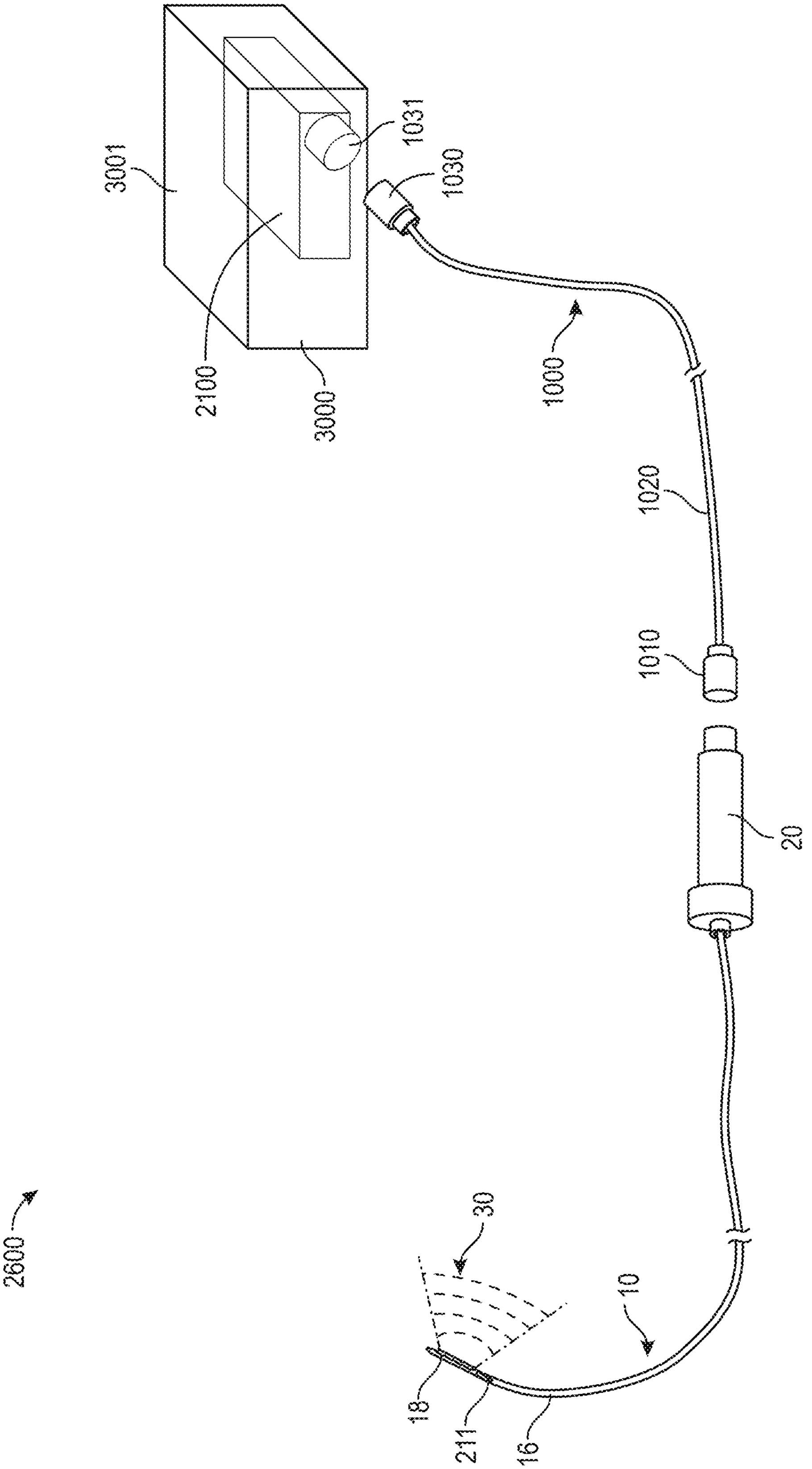
FIG. 26 illustrates another ICE system having an ICE catheter and an ultrasound assembly configured in accordance with embodiments of the present technology.

FIG. 26 illustrates another distributed ICE system 2600 configured in accordance with embodiments of the present technology. The ICE system 2600 can be generally similar to the ICE system 2500. Accordingly, the description of similarly numbered components in FIG. 25 applies equally to FIG. 26, except as otherwise noted. Relative to the system 2500 of FIG. 25, in the system 2600 of FIG. 26 the ultrasound assembly 2100 can by physically integrated within the computing system 3000. For example, the ultrasound assembly 2100 can reside within a common housing 3001 of the computing system 3000 (e.g., the ultrasound assembly 2100 circuitry can be integrated into the same enclosure as the computing system 3000 and hardwired to it over minimal connection lengths). Without intending to be bound by theory, integrating the circuitry into the computing system 300 can minimize system signal losses and cross talk over cabling to improve the overall signal to noise ratio and thus improve the quality of the displayed image. In embodiments in which the computing system 3000 is an EPMS, the EPMS can be used as the UI and display, such that the ultrasound image may be displayed within a window of the EPMS, and the ultrasound image controls manipulated through the EPMS software and EPMS UI. The ultrasound image could alternatively be displayed on a dedicated monitor screen and the UI controlled through a separate software and input means (e.g., separate laptop computer).

It can be advantageous during certain procedures to merge ultrasound images from an ICE system with images from an EPMS. To do this using existing systems, the output of the processed images from the ultrasound system must be sent to the EPMS. But existing ultrasound systems and EPMSs are distinct systems that are typically manufactured by and/or owned by different companies, are generally not designed to be compatible, and must retain the ability to function independent of one another for typical use. As a result, various components of the systems cannot be "shared." However, the system 2600 addresses this shortcoming by providing an ultrasound assembly 2100 integrated within the system 3000. Accordingly, the ultrasound assembly 2100 can share certain components (e.g., computational hardware, user interface terminal, etc.) with the system 3000, which may reduce overall capital equipment requirements, associated cost, and physical space required for the systems.

Figure 27A:
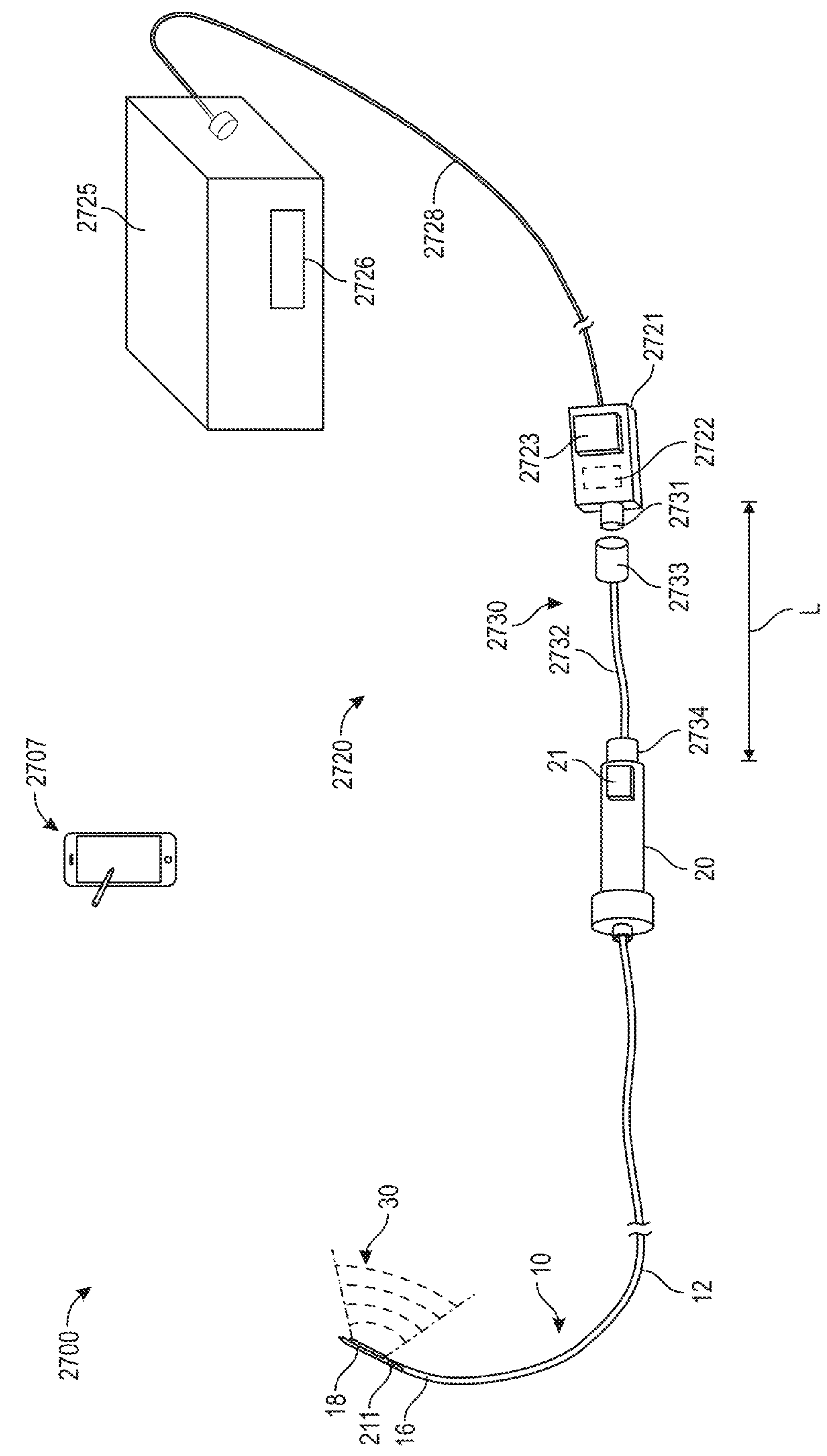
FIGS. 27A-27G illustrate another ICE system having an ICE catheter and an ultrasound assembly configured in accordance with embodiments of the present technology.

In some embodiments, one or more components of the ultrasound assembly such as the analog-front-end can be positioned within a housing configured to be positioned near the ICE catheter. For example, FIG. 27A illustrates ICE system 2700 configured in accordance with embodiments of the present technology. Similar to the ICE systems 2500 and 2600 of FIGS. 25 and 26, the ICE system 2700 includes an ICE catheter 10 and an ultrasound module or assembly 2720. The ICE catheter 10 can be generally similar to or the same as any of the ICE catheters described throughout this Detailed Description. For example, the ICE catheter 10 can include a handle 20, a shaft 12, and a transducer tip region 16 having an imaging transducer 18 for generating an ultrasonic field 30. The shaft 12 can have a diameter suitable for ICE procedures, such as between about 6 French and about 14 French, or between about 7 French and 11 French, or between about 8 French and about 10 French, or about 9 French.

The ultrasound assembly 2720 has multiple, distinct housings for housing different components of the ultrasound assembly 2720. In the illustrated embodiment, for example, the ultrasound assembly 2720 includes a first housing or enclosure 2721 and a second housing or enclosure 2725. The first housing 2721 can include an analog-front-end ("AFE") 2722 of the ultrasound assembly 2720 for converting signals between analog and digital formats. The first housing 2721 can further include additional components, such as other beam-forming components (e.g., FPGAs, transmit and receive beamformers, etc.), electronics for controlling the AFE 2722 or other beam-forming components (e.g., transmit and receive electronics), a mixer, one or more fans, etc. In some embodiments, the first housing 2721 can have no fans or at least fewer fans than in conventional ultrasound systems by virtue of the first housing 2721 including only a subset of components commonly co-located within a single housing in ultrasound systems, as described in greater detail below. For example, in some embodiments, the first housing 2721 does not include any image construction firmware or hardware.

The second housing 2725 can include an image processing unit 2726 for processing signals received from the AFE 2722. For example, the image processing unit 2726 can process digitized signals received from the AFE 2722 and render a two- or three-dimensional image based on the digitized signals. The image processing unit 2726 can be operably coupled to a user display (not shown) to display the rendered two- or three-dimensional image. The second housing 2725 may house additional features, such as flow estimate software modules for processing I/Q vectors to estimate flow.

In some embodiments, the image processing unit 2726 can be incorporated into another computing system such as an EPMS or a dedicated laptop or other computing system with a processor, memory, user display, and the like, as described with reference to FIG. 26. Indeed, by virtue of positioning the AFE 2726 (and other ultrasound-specific components) in the first housing 2725, the remaining components needed to support the ultrasound assembly 2720 (e.g., computer architecture for the image processing unit 2726) can be shared with another system. In embodiments in which the image processing unit 2726 is incorporated into an EPMS, the second housing 2725 can be a housing of the EPMS. The second housing 2725 can therefore include the image processing unit 2726 and other computing modules for supporting EPM. For example, the second housing 2725 can include an EPM processing unit that can receive electrical signals and 3D positional data from an EPM catheter having electrodes for measuring the electrical activity of the heart and/or a sensor able to detect the 3D position of at least a portion of the EPM catheter in the heart. The EPM processing unit can process the received electrical signals and/or sensor data to produce a map of an electrical activity of a patient's heart and/or a 3D model of the physical structure of the cardiac chambers and other tissue structures, which may optionally have the electrical data overlaid on the surface of the structure. In such embodiments, the first housing 2721 can be electrically connected to and between the ICE catheter 10 and the second housing 2725, while the EPM catheter can be electrically connected to the second housing 2725 without being electrically connected to the first housing 2721.

The first housing 2721 can be connected to the second housing 2725 via one or more cables 2728. The cables 2728 can include power cables for transmitting power to the first housing 2721, and/or data cables for transmitting digitized signals from the AFE 2722 in the first housing 2721 to the image processing unit 2726 in the second housing 2725. Example cables include, but are not limited to, USB 3.x (or faster) or LAN ethernet cable with power. The one or more cables 2728 can have a length of between about 1 meter and about 10 meters, or between about 2 meters and about 9 meters, or between about 4 meters and about 8 meters, or between about 5 meters and about 7 meters, although in other embodiments the one or more cables 2728 may have lengths outside of the foregoing ranges. For example, in some embodiments the first housing 2721 and the second housing 2725 can be designed to be positioned in close proximity such that the cable 2728 has a length of less than about 2 meters, less than about 1 meter, or less than about 0.75 meters.

In some embodiments, the first housing 2721 is relatively smaller than conventional ultrasound system housings. For example, the first housing 2721 may have a volume of less than about 5,000 $cm^3$, less than about 3,000 $cm^3$, less than about 1,500 $cm^3$, less than about 1,000 $cm^3$, less than about 750 $cm^3$, less than about 500 $cm^3$, less than about 400 $cm^3$, less than about 300 $cm^3$, less than about 200 $cm^3$, or less than about 100 $cm^3$. As described in greater detail below with reference to FIGS. 28A-28F, having a relatively smaller first housing 2721 can be advantageous in embodiments in which the first housing 2721 is positioned within or in close proximity (e.g., within 1.5 meters, or 2.0 meters) to the sterile field of the operating room. As also described in detail below, this can, among other things, reduce lab clutter and improve signal fidelity and accuracy. A number of factors can contribute to reducing the size of the first housing 2721 relative to conventional systems, as set forth below.

In some embodiments, the first housing 2721 is smaller than conventional ultrasound systems by virtue of being dedicated specifically to ICE. Conventional ultrasound systems relied upon a single, multi-functional system or console that worked with multiple probes, each having different sizes and applications. Such systems/consoles would therefore be configured to accommodate the specific imaging needs of all the various probes, and thus have a wide range of capabilities built in. Moreover, because each system/console would only have a single AFE and image processing unit, the capabilities of each of these component must be designed for the most demanding probe. This in turn contributed to conventional, multi-functional systems/consoles being large and expensive. In contrast, the first housing 2721 may be smaller by virtue of the ultrasound assembly 2720 being designed specifically for ICE, rather than being designed to support many types of ultrasound. As a result, the AFE 2722 must just be compatible with the minimum imaging and connectivity requirements of a single probe, in this case the ICE catheter 10, instead of having large and generalized connectors to different probes and the ability to support a wide number of probes with differing numbers of transducer elements. With ICE catheters having fewer channels to support than many probes, both the number of AFE chips and associated circuitry is reduced, reducing the size requirements of the AFE 2722. For example, in some embodiments the AFE 2722 has 3 chipsets, 2 chipsets, or even 1 chipset (each supporting 32 channels). This further reduces the processing load at the AFE 2722, which can also reduce cooling requirements, which in turn can reduce the number and size of air circulation fans needed in the housing 2721. Alternative cooling methods such as customized heat fin shapes and materials or fluid circulation can also contribute to a reduction in size of the housing 2721.

In some embodiments, the first housing 2721 is smaller than conventional ultrasound systems by virtue of placing certain components in the second housing 2725. Conventional ultrasound systems/consoles have the circuitry for the AFE integrated with the image processing over a short distance to maintain data transfer rates. However, with the advent of USB 3.x and higher connections, digital transfer of the data from the AFE 2722 to the image processing unit 2726 is possible over further distances. Embodiments of the present technology leverage this to move certain components (e.g., the image processing unit 2726) into a separate housing (e.g., the second housing 2725), thereby taking advantage of shorter analog transfer distances and greater digital transfer distances and enabling a reduction in the size of the first housing 2721.

Other factors in addition to those set forth above can contribute to the relatively small form factor of the first housing 2721. For example, the first housing 2721 may be designed to operative with "simpler" imaging techniques, such as B-mode ultrasound, that requires less AFE circuitry and less cooling requirements than advanced ultrasound techniques such as acoustic radiation force impulse (ARFI) or push ultrasound imaging. In other embodiments, however, the ultrasound assembly 2720 is designed to enable color-flow imaging.

As illustrated in FIG. 27A, the first housing 2721 can be removably coupleable to the ICE catheter 10 via a connection assembly 2730. In the illustrated embodiment, the connection assembly 2730 includes a first connector 2731 extending from the first housing 2721, and a connector cable 2732 having a connector cable first end 2733 and a connector cable second end 2734. To couple the first housing 2721 to the ICE catheter 10, the connector cable first end 2733 can be connected to the first connector 2731 on the first housing 2721, and the connector cable second end 2734 can be connected to the handle 20 of the ICE catheter 10. The connections can be formed using any suitable connection mechanism that permits the transmission of analog signals. Similarly, the connector cable 2732 can have any suitable structure for transmitting analog signals between the AFE 2722 and the ICE catheter 10. Example structures include, but are not limited to, co-axial cables and twisted pair cables. In some embodiments, the structure of the connector cable 2732 is designed to match the structure of corresponding cables within the ICE catheter 10. In various embodiments, the connector cable 2732 can be fixedly (e.g., non-removably) connected to and extending from one of the first housing 2721 or the handle 20. In some embodiments, the connector cable 2732 is omitted entirely and the first connector 2731 is configured to be plugged directly into the handle 20 such that the first housing 2721 is directly coupled to and in apposition with the handle 20.

Figure 27B:
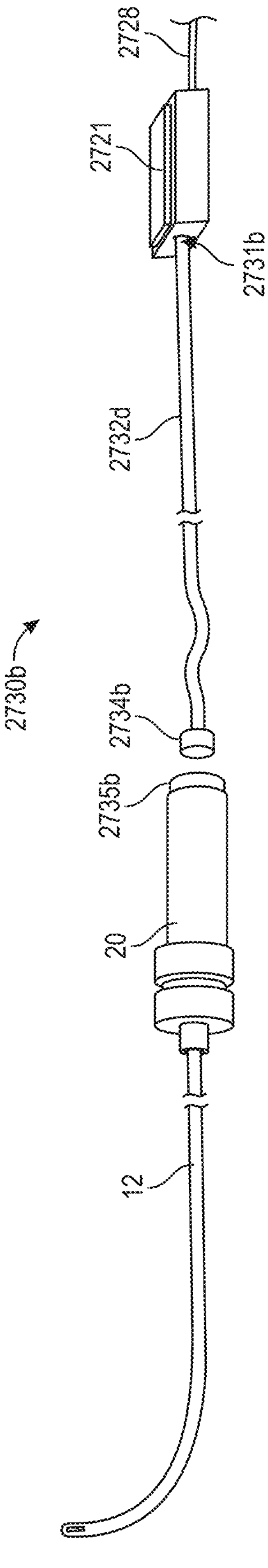
Figure 27C:
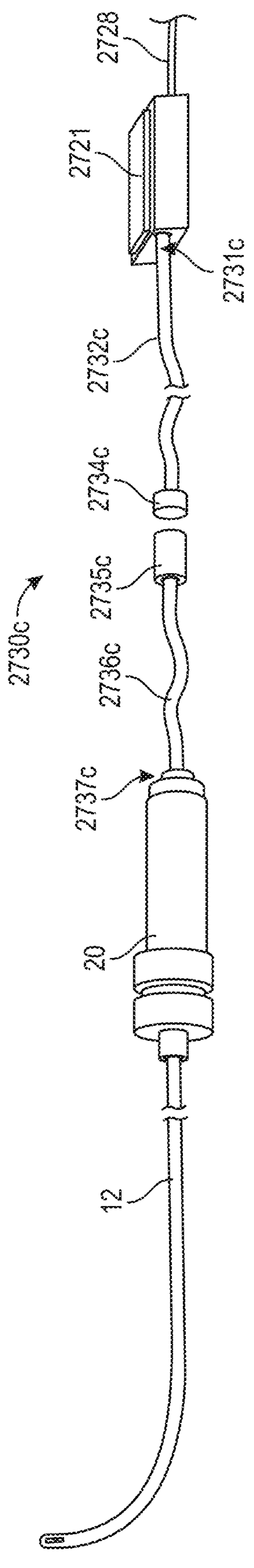

FIGS. 27B-27F illustrate various alternative embodiments of connection assemblies 2730*b-f*. For example, FIG. 27B illustrates a connection assembly 2730*b* in which a connector cable 2732*b* has a first end 2731*b* integrated into or otherwise fixedly coupled to the first housing 2721 and a second end with a catheter-side cable connector 2734*b*. The catheter-side cable connector 2734*b* can be configured to be releasably coupled to a connector receptacle 2735*b* on the handle 20. FIG. 27C illustrates a connection assembly 2730*c* having a connector cable 2732*c* with a first end 2731*c* integrated into or otherwise fixedly coupled the first housing 2721 and a second end with a catheter-side cable connector 2734*c*, similar to the connection assembly 2730*b* of FIG. 27B. Relative to FIG. 27B, however, the connection assembly 2730*c* includes an extension cable 2736*c* extending from a first end 2737*c* that is integral with the handle 20 to a second end having a connector receptacle 2735*c* for releasably coupling to the catheter-side cable connector 2734*c*.

Figure 27D:
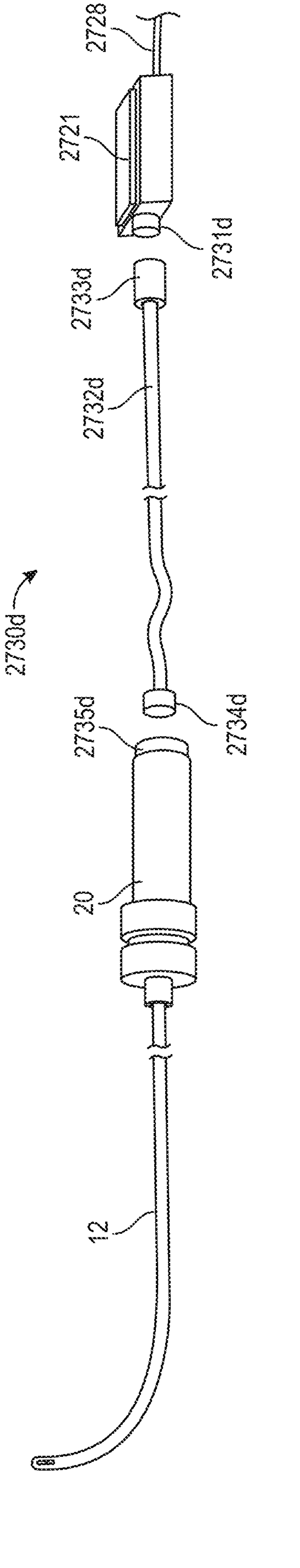
Figure 27E:
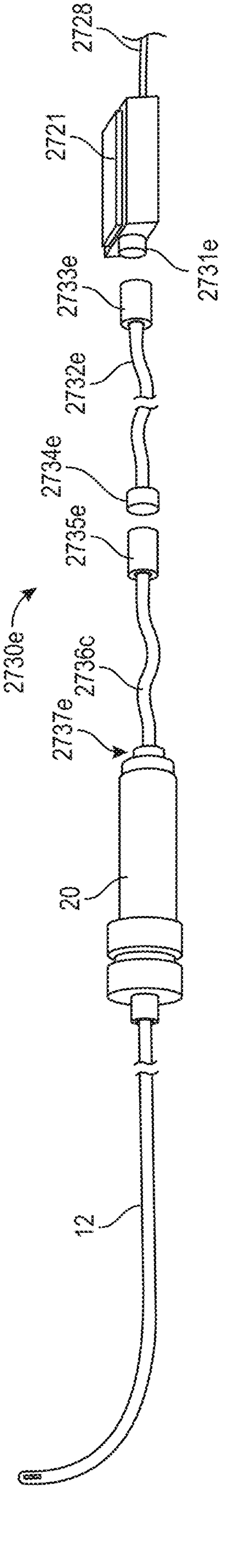
Figure 27F:
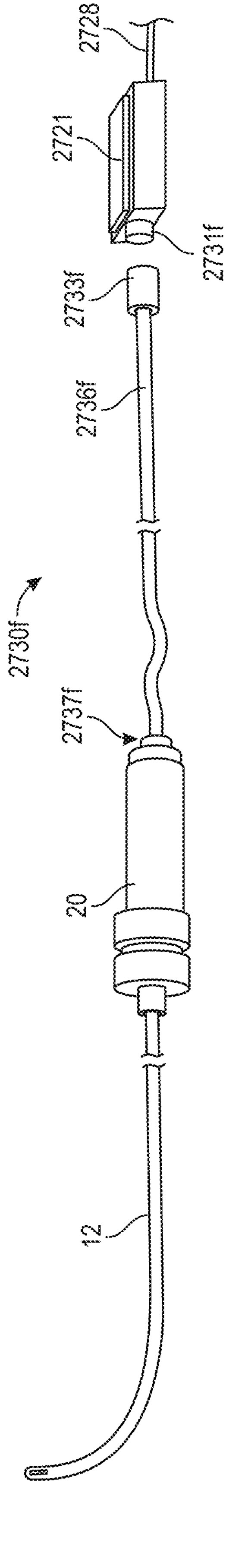

FIG. 27D illustrates an embodiment of a connection assembly 2730*d* in which a connector cable 2732*d* is configured to be directly and releasably connected to the handle 20 and the first housing 2721. In particular, the connector cable 2732*d* includes a connector cable first end 2733*d* configured to be releasably coupled to a first connector 2731*d* on the first housing 2721, and a connector cable second end 2734*d* (which can also be referred to as a catheter side connector) configured to be releasably coupled to a connector receptacle 2735*d* on the handle. FIG. 27E illustrates an embodiment of a connection assembly 2730*e* in which a connector cable 2732*e* has a connector cable first end 2733*e* configured to be releasably coupled to a first connector 2731*e* on the first housing 2721, and a connector cable second end 2734*e* (which can also be referred to as a catheter side connector), similar to the connection assembly 2730*d* of FIG. 27D. Relative to FIG. 27D, however, the connection assembly 2730*e* includes an extension cable 2736*c* extending from a first end 2737*e* that is integral with the handle 20 to a second end having a connector receptacle 2735*e* configured to be releasably coupled to the connector cable second end 2734*e*. FIG. 27F illustrates an embodiment of a connection assembly 2730*f* with an extension cable 2736*f* extending between a first end 2737*f* integrated into or otherwise fixedly coupled to the handle 20, similar to the connection assembly 2730*e* of FIG. 27E. Relative to FIG. 27E, however, the extension connector cable 2736*f* includes a connector cable first end 2733*f* (which can also be referred to as the system side connector) configured to releasably couple the extension connector cable 2736*f* directly to a first connector 2731*f* on the first housing 2721.

Figure 27G:
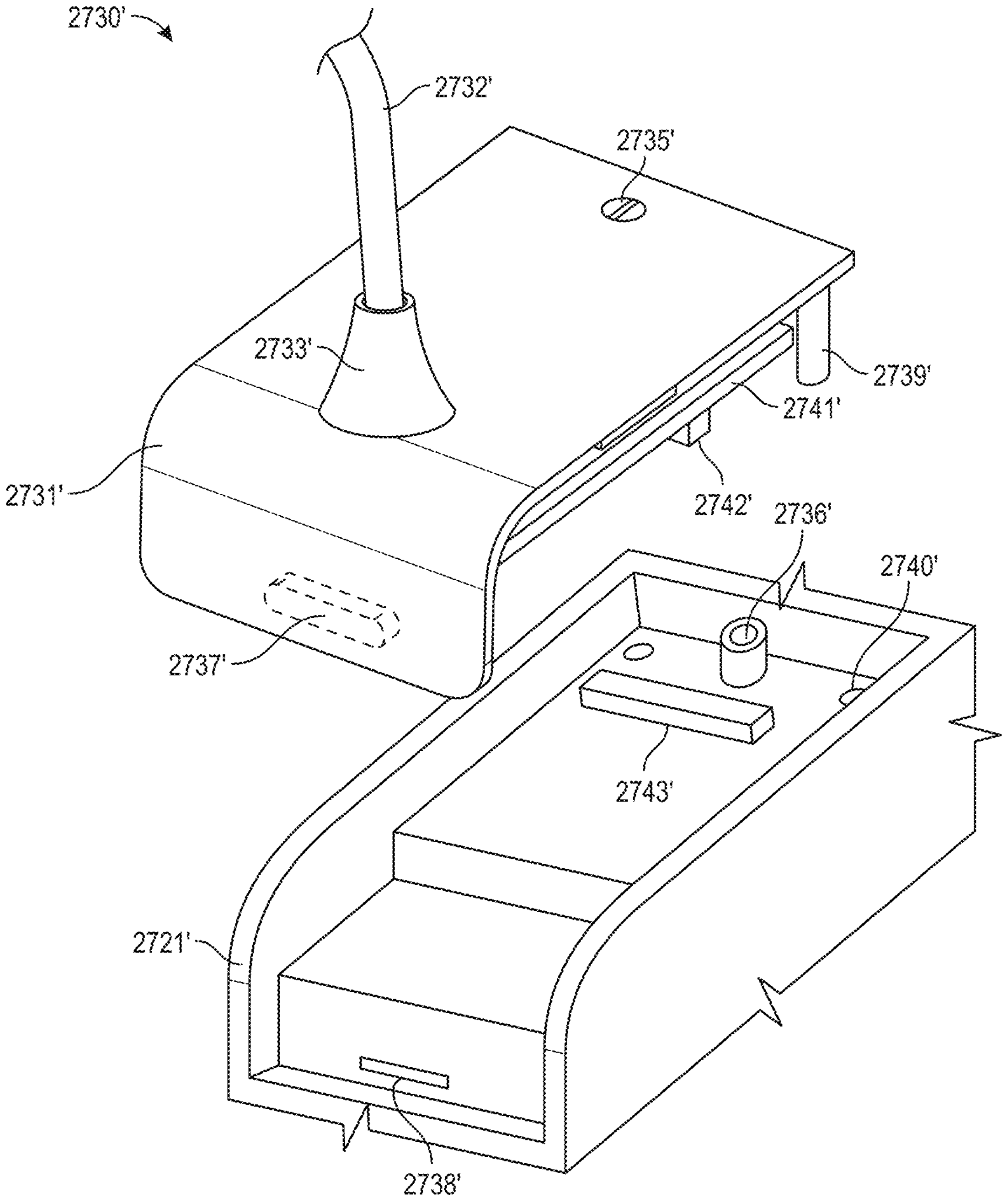

FIG. 27G illustrates another embodiment of a connection assembly 2730' that can be used with the system 2700 of FIG. 27A and configured in accordance with embodiments of the present technology. In this embodiment, a first housing 2721' (which can hold the AFE 2722; not shown in FIG. 27G) can include a removable panel 2731', which is shown in a partly removed configuration for purposes of illustration. The removable panel 2731' can include an integrated connector cable 2732' connected to the removable panel 2731' via a connector cable first end 2733'. Although not shown, a second end of the connector cable 2732' can be configured to be removably coupled to a connector receptacle within an ICE catheter handle, or incorporated into an extension cable extending from a location integrated within the handle, as described above with reference to FIGS. 27B-27F. A printed circuit board 2741' can be connected to an interior face (not shown) of the removable panel 2731' and can be electrically coupled to an interior of the first housing 2721' (e.g., to the AFE 2722) via corresponding pin mating connectors 2742' and 2743'. The removable panel 2731' can be removably locked to the first housing 2721' via a screw (or similar conventional fastener) 2735' that can be inserted into a corresponding screw hole 2736' on an interior of the first housing 2721'. For example, turning the screw 2735' 90-degrees in a first direction may lock the removable panel 2731' to the first housing 2721', and turning the screw 2735' 90-degrees in a second direction may unlock the removable panel 2731' from the first housing 2721'.

The connection assembly 2730' shown in FIG. 27G can have additional locking and alignment features. For example, the removable panel 2731' can have a tab 2737' configured to removably fit (e.g., snap-fit) into a corresponding slot 2738' on an interior of the housing 2721'. The removable panel 2731' can also have one or more pins 2739' that can fit into corresponding apertures 2740' on an interior of the housing 2721', e.g., to ensure proper alignment between the removable panel 2731' and the first housing 2721'. As one skilled in the art will appreciate, the connection assembly 2730' may include only some of the foregoing connection/alignment mechanisms, and/or may include additional connection/alignment mechanisms, in addition to or in lieu of the foregoing. Potential advantages of the embodiment shown in FIG. 27G include, but are not limited to, the ability to "lock" the cable 2732' to the first housing 2721' to prevent user access to the interior of the housing 2721' and/or to ensure a stable connection between the cable 2732' and the first housing 2721'. Further, the cable 2732' can be replaced, if needed, using a standard tool such as a flat head screw driver, Allen wrench, Torx wrench, or other conventional tools for the specific type of fastener used.

Regardless of its configuration, the connection assemblies of FIGS. 27A-27F can each have a length L of less than about 3 meters. Referring specifically to FIG. 27A, this length L is inclusive of the length of the connector cable 2732 and any non-overlapping length of the first connector 2731. Accordingly, the maximum distance separating the handle 20 and the first housing 2721 is about 3 meters, although the handle 20 and the first housing 2721 can be positioned relatively closer together due to the flexibility of the connector cable 2732. Stated otherwise, signals being transmitted between the AFE 2722 and the handle 20 travel a maximum of about 3 meters. In some embodiments, the connection assembly 2730 has a length L of less than about 2.5 meters, less than about 2 meters, less than about 1.5 meters, less than about 1 meter, less than about 0.8 meters, less than about 0.6 meters, less than about 0.5 meters, less than about 0.4 meters, less than about 0.3 meters, less than about 0.2 meters, or less than about 0.1 meters. In such embodiments, the maximum distance transmitted signals must travel between the AFE 2722 and the handle 20 correspond to the length of the connection assembly 2730.

As described in greater detail with reference to FIGS. 28A-28F, one expected advantage of keeping the first housing 2721 (and thus the AFE 2722) relatively close to the ICE catheter 10 is to minimize the distance the analog signal coming from the ICE catheter 10 must travel compared to conventional ultrasound systems, because such analog signal transmissions are subject to signal decay and noise injection and emission. In conventional ultrasounds systems, for example, the analog signal generally must travel further (e.g., at least 3 meters or further) between the ICE catheter and the AFE because the AFE is co-located with the dedicated ultrasound console that is generally too large and cumbersome to be positioned proximate the ICE catheter in the generally crowded catheter lab room. In contrast, by positioning the AFE in the first (compact) housing 2526, the imaging data from the ICE catheter 10 is digitized within the first housing 2721 and can be transmitted more rapidly over the cable 2728 with less signal corruption than if the AFE 2722 was co-located with the image processing unit 2726 such that the analog signal from the ICE catheter 10 must travel the full distance to the image processing unit 2726. For example, the configuration shown in FIG. 27 is expected to result in a 0.5 to 3.0 decibel improvement in signal loss, as compared to conventional ICE ultrasound systems.

The ultrasound assembly 2720 can further include a controller 2707 having a user interface for controlling various operations of the ultrasound assembly 2720. The controller 2707 can be a cellular phone, tablet, laptop computer, desktop computer, or other similar structure with a touchscreen and/or a physical user input. The controller 2707 can be connected to the ultrasound assembly 2720 via a wired or wireless connection. In some embodiments, the controller 2707 can be configured to be located in the sterile field under a protective sterile cover for access by a sterile operator. In other embodiments, the controller 2707 can be configured to be located within the cath lab outside the sterile field, or within a control room adjacent the cath lab. In yet other embodiments, the ultrasound assembly 2720 can include a first controller (e.g., the controller 2707) configured to be located within the sterile field under a protective sterile cover for access by a sterile operator, and a second, different controller configured to be located within the cath lab outside the sterile field, and/or a third, different controller configured to be located within a control room adjacent the cath lab. In some embodiments, the controller 2707 is integrated in a controller for another medical system, such as an EPMS.

As described in greater detail below with reference to FIGS. 28A-28F, in some embodiments the first housing 2721 can be located within the sterile field under a protective sterile cover or otherwise near the sterile field. For example, the first housing 2721 can be positioned near the patient's feet, secured to a stand elevated above the patient (preferably above the lower legs or feet), or secured to a stand or IV pole adjacent or positioned near the table, or similar means. The second housing 2725 can be positioned within the sterile field under a protective sterile cover, in the cath lab outside the sterile field, and/or in a non-sterile control room. In embodiments in which the connection to the catheter handle 20 is located in the sterile field, a sterile sleeve could be extended from a secured location on the catheter handle 20 (and/or catheter's electrical connector receptacle), over the mating connector, and to a location outside the sterile field.

In operation, the AFE 2722 can transmit first electrical signals to the transducer 18 via the connection assembly 2730 and the electrical conductors within shaft 12. The transducer 18 can convert the first electrical signals into acoustic waves to generate the field 30. The transducer 18 can then sense the returned acoustic waves and convert the returned waves into a second electrical signal, which itself can then be transmitted back to the AFE 2722 via the electrical conductors within shaft 12 and the connection assembly 2730. The AFE 2722 can digitize the second electrical signal and transmit the digitized second electrical signals to the image processing unit 2726 for processing and image rendering. Depending on the length of the ICE catheter, the second electrical signal may be transmitted a total distance between the transducer 18 and the AFE 2722 of less than about 7 meters, less than about 6 meters, less than about 5 meters, less than about 4 meters, less than about 3 meters, or less than about 2 meters.

In a related optional embodiment shown in FIG. 27A, a few simple local user interface (LUI) controls 2723 could be integrated directly on the first housing 2721. This could allow a sterile user (accessing with a sterile cover) to manipulate certain commonly used imaging functions without having to ask an external operator to do so. The first housing 2721 could alternatively be outside the sterile cover but in a more convenient non-sterile location than the equipment rack, such that a non-sterile operator could manipulate the LUI controls 2723 at the request of the sterile operator. The location closer to the table would be more convenient so that the non-sterile operator could see the imaging screen and sterile operator more directly than if closer to the equipment rack or other location that is typically more remote to allow room to place large capital equipment. Additionally or alternatively, LUI controls 21 could be located directly on the catheter handle 20, allowing for the operator to manipulate the controls without having to move a hand away from the catheter handle. The LUI controls 2723 or 21 could also be on a separate unit with a wired or wireless connection to the AFE 2722 or image processing unit 2726. The LUI controls 2723 or 21 could be in the form of press buttons, switches, dials, joysticks, trackballs, sliders, or any combination thereof. They may be physical controls and/or integrated into an i-phone-like graphical interface touch screen. In some embodiments, certain features to at least include in LUI 2723 or 21 would be controls to change the imaging mode, depth, gain, and frequency to optimize the image quality during use. Other imaging features could be fully controlled from the remote UI.

The ICE catheter 10 may also incorporate a location sensor (LS) 211 within the ultrasound catheter tip 16 in a fixed orientation relative to the transducer 18. While similar to the sensor 210 described in FIGS. 14D and 14E, the LS 211 can be used to calibrate the location of the ultrasound image (from the acoustic waves 30) relative to the ultrasound transducer 18. The LS 211 can be configured from 2 or 3 coil circuits (e.g., electric wires coiled around a ferrite core, or a flex circuit with a substantially circular or tightly spiraled circuit path) that when moved within a calibrated magnetic field created around the patient can provide location information of the LS 211 back to the system in 3D space. This capability can allow the system to correlate the ultrasound image to a 3D map of cardiac structures created by the mapping system (as well known in the art). The ultrasound image can be overlaid on the 3D map, as dynamic moving model, or as gated to a particular time within the electrical ECG cycle of the heart, matched with the gated model of the heart generated by the EPMS. Multiple ultrasound images may also be obtained from the ultrasound catheter 10 and stitched together with software to create a 3D model of the heart (preferably gated to a time within the ECG cycle) and used by the EPMS to generate the model of the heart. The leads from the LS 211 can be twisted pairs or coaxes and extend through the catheter 10 to a location on the handle 20. From the handle 20, the sensor leads may be routed within, through, or around the first housing 2721, to the second housing 2725 (and/or hardware related to it) through a dedicated cable and connectors or by routing through the existing cables and connectors used for the ultrasound imaging. The LS cable may be routed directly to the EPMS (or related interface units) instead of passing through either the first housing 2721 or second housing 2725. Certain isolation circuitry may be implemented as needed for the sensor lines to isolate them from the ultrasound imaging lines. This isolation circuitry may be within the LS cable itself, the first housing, 2721, or the second housing 2725.

Figure 28A:
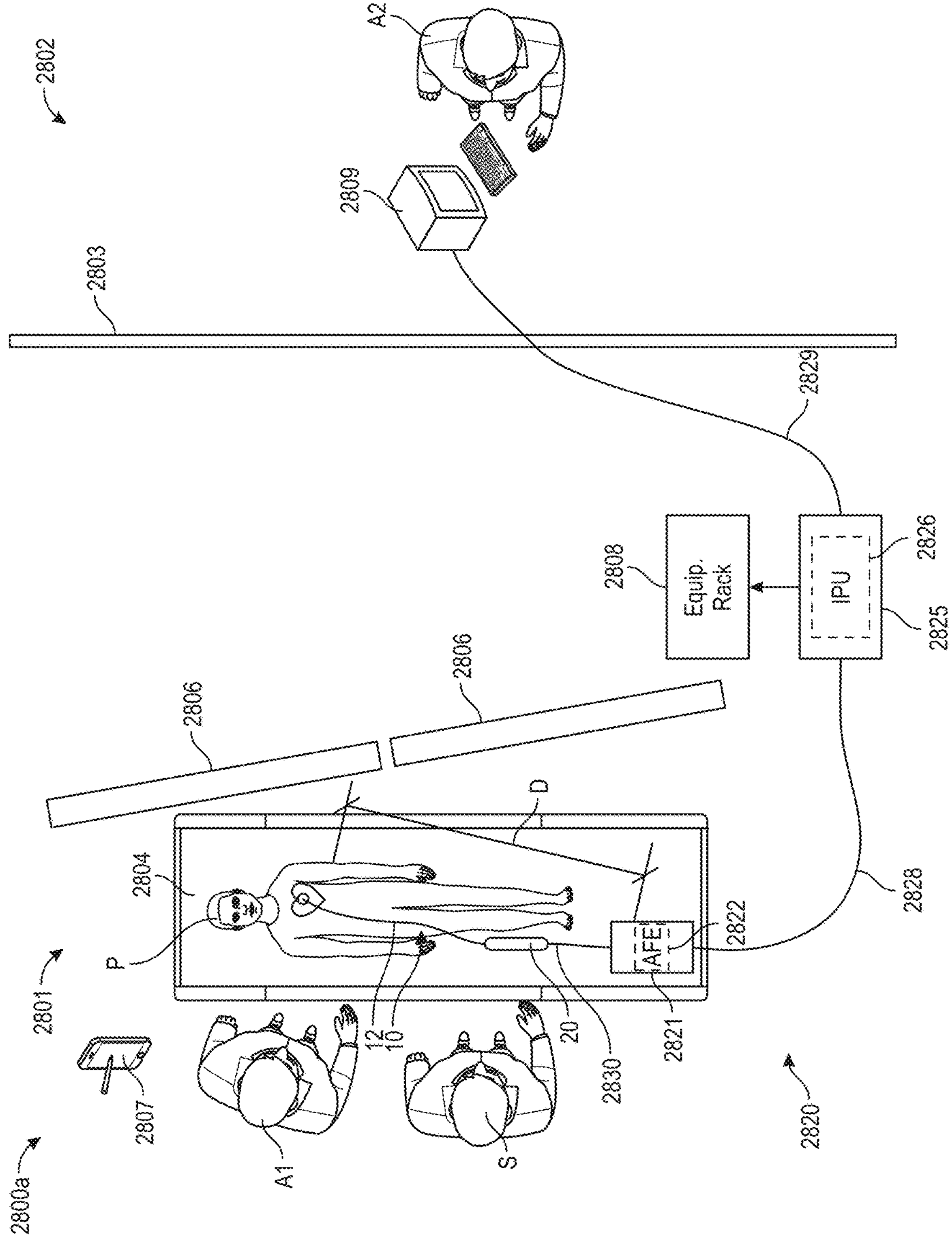
FIGS. 28A-28F illustrate various operative set ups for using an ICE system in accordance with embodiments of the present technology.

The ICE systems described throughout the present disclosure are expected to provide several advantages in operative settings. For example, FIG. 28A illustrates a first representative operative set up 2800*a* for intracardiac echocardiography configured in accordance with select embodiments of the present technology. The operative set up 2800*a* includes a (generally sterile) operating room or catheter lab 2801 and a (generally non-sterile) control room 2802, divided by a wall or other partition 2803. The operating room 2801 can include equipment for interventional operations, such as an operating table or bed 2804 for supporting a patient P, one or more monitors 2806, and an equipment rack 2808. The control room 2802 can include supplemental medical equipment for supporting procedures within the operating room 2801. For example, the control room 2802 can include a computing system 2809 for at least partially controlling one or more aspects of a medical procedure being performed in the operating room 2801. In some embodiments, the computing system 2809 can be an electrophysiology mapping system, such as the system 3000 described with reference to FIGS. 25 and 26. In other embodiments, the computing system 2809 can be a laptop or desktop computer, or other dedicated computing structure.

The operative setup 2800*a* can be used to perform procedures using the ICE catheters described herein (such as the ICE catheter 10 having the handle 20 and the shaft 12) and an ultrasound assembly 2820. The ultrasound assembly 2820 can be generally similar to or the same as the ultrasound assembly 2720 described with reference to FIGS. 27A and 27B. For example, the ultrasound assembly 2820 can have a first housing 2821 having an AFE 2822, a second housing 2825 having an image processing unit 2826, a cable 2828 connecting the first housing 2821 and the second housing 2825, a connection assembly 2830 for connecting the first housing 2821 to the ICE catheter 10, and a controller 2807. Accordingly, the description of the ultrasound assembly 2720 with reference to FIGS. 27A and 27B can apply equally to the ultrasound assembly 2820. The second housing 2825 with the image processing unit 2826 can be connected to the computing system 2809 via a secondary cable 2829.

As shown in FIG. 28A, the first housing 2821 can be positioned on the operating table 2804 due to its relatively small enclosure and ability to sit under a protective sterile cover within the sterile environment of the operating room 2801. As a result, the first housing 2821 is in relative close proximity to the ICE catheter 10. For example, as shown, a distance D between the distal end of the ICE catheter 10 and the first housing 2821 can be less than about 6 meters, less than about 5 meters, less than about 4 meters, less than about 3 meters, or less than about 2 meters. As described previously, this set up is expected to be advantageous relative to conventional ultrasound systems because it reduces the distance that analog signals must travel between the ICE catheter transducer (not shown in FIG. 28A) and the AFE 2822. In turn, this is expected to reduce the distortion (e.g., due to noise, decay of signal, etc.) of the analog signal before it is converted into a digital signal, which may enable the ultrasound assembly 2820 to produce ultrasound images with higher fidelity, accuracy, speed, etc.

In some embodiments, the operative setup 2800*a* may reduce the number of healthcare providers needed to perform ICE procedures. For example, the operative set up 2800*a* can be designed to function with three healthcare providers. For example, a surgeon S can operate the ICE catheter 10, a first surgical assistant A1 can control one or more functions of the ultrasound assembly 2820 via the controller 2807 from within the operating room 2801, and a second surgical assistant A2 can control one or more functions associated with merging the output from the ultrasound assembly 2820 and other medical equipment (e.g., an electrophysiology mapping system) via the computing system 2809 in the control room 2802 (e.g., for display via the monitors 2806). The surgeon S may also (or instead of surgical assistant A1) be able to control aspects of the ultrasound assembly 2820 via one or more controls (not shown) on the first housing 2821, similar to the LUI controls 2723 described with reference to FIG. 27A, or by using the controller 2807 protected by a sterile cover. Without intending to be bound by theory, the present technology may reduce the number of healthcare providers required to perform ICE procedures by virtue of removing the need for a dedicated ultrasound operator to be manipulating a standard ultrasound console. As one skilled in the art will recognize, however, the systems and procedures described herein may be designed to be performed with fewer or more healthcare providers, and is not limited to the particular set up shown in FIG. 28A.

The operative setup 2800*a* may provide additional advantages, in addition to or in lieu of the foregoing advantages. For example, by dividing the ultrasound module 2820 into a first housing 2821 and a second housing 2825, only the first housing 2821 must be at or near the operating table 2804, and the second housing 2825 can be positioned somewhere "out of the way" so that it does not add to the already-crowded environment near the operating bed 2804 and the surgeon S. For example, as shown in FIG. 28A, the second housing 2825 can be positioned on the equipment rack 2808, which itself can be positioned at a corner or other location of the operating room 2801 (e.g., behind the monitors 2806) that does not interfere with the surgeon S.

Figure 28B:
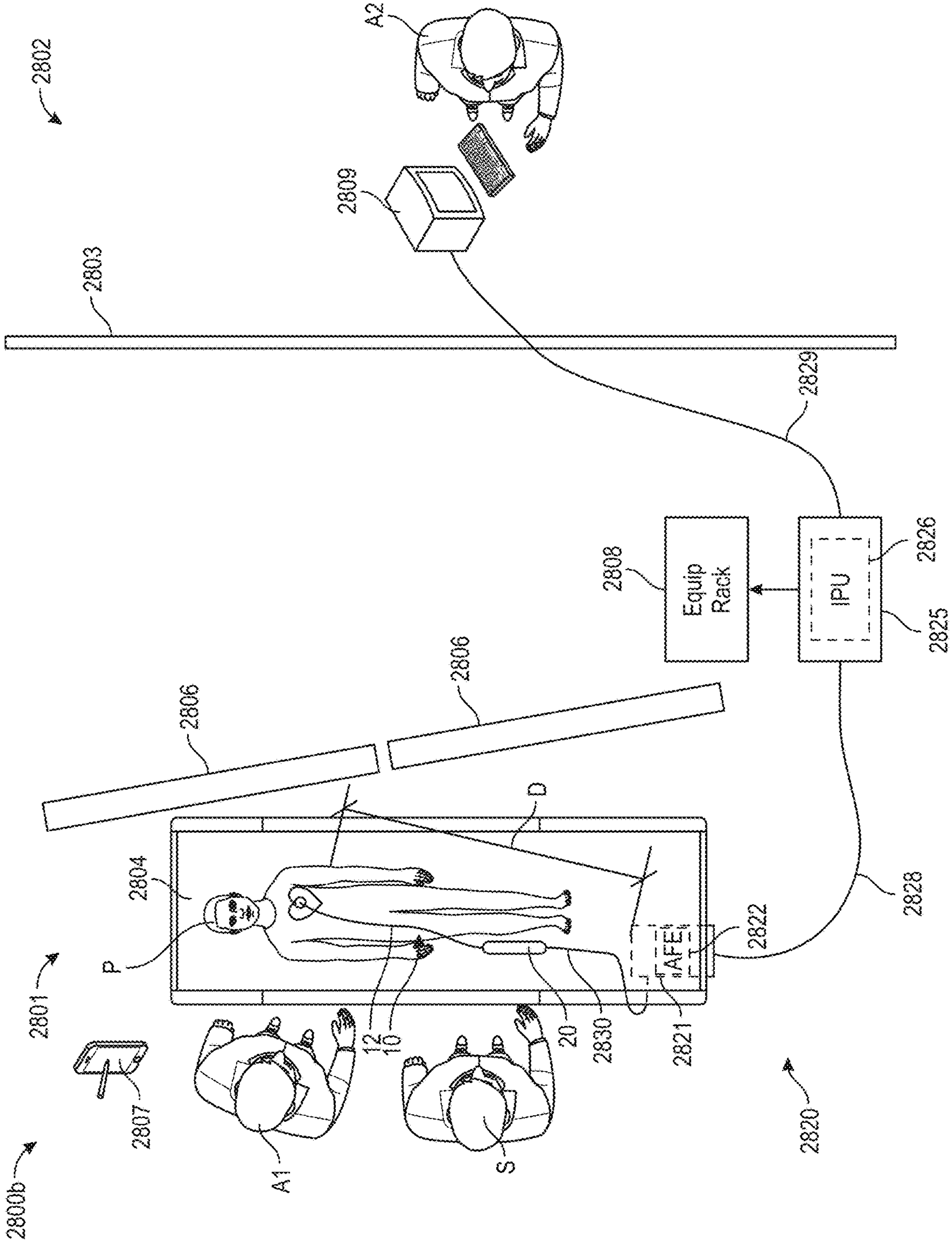
Figure 28C:
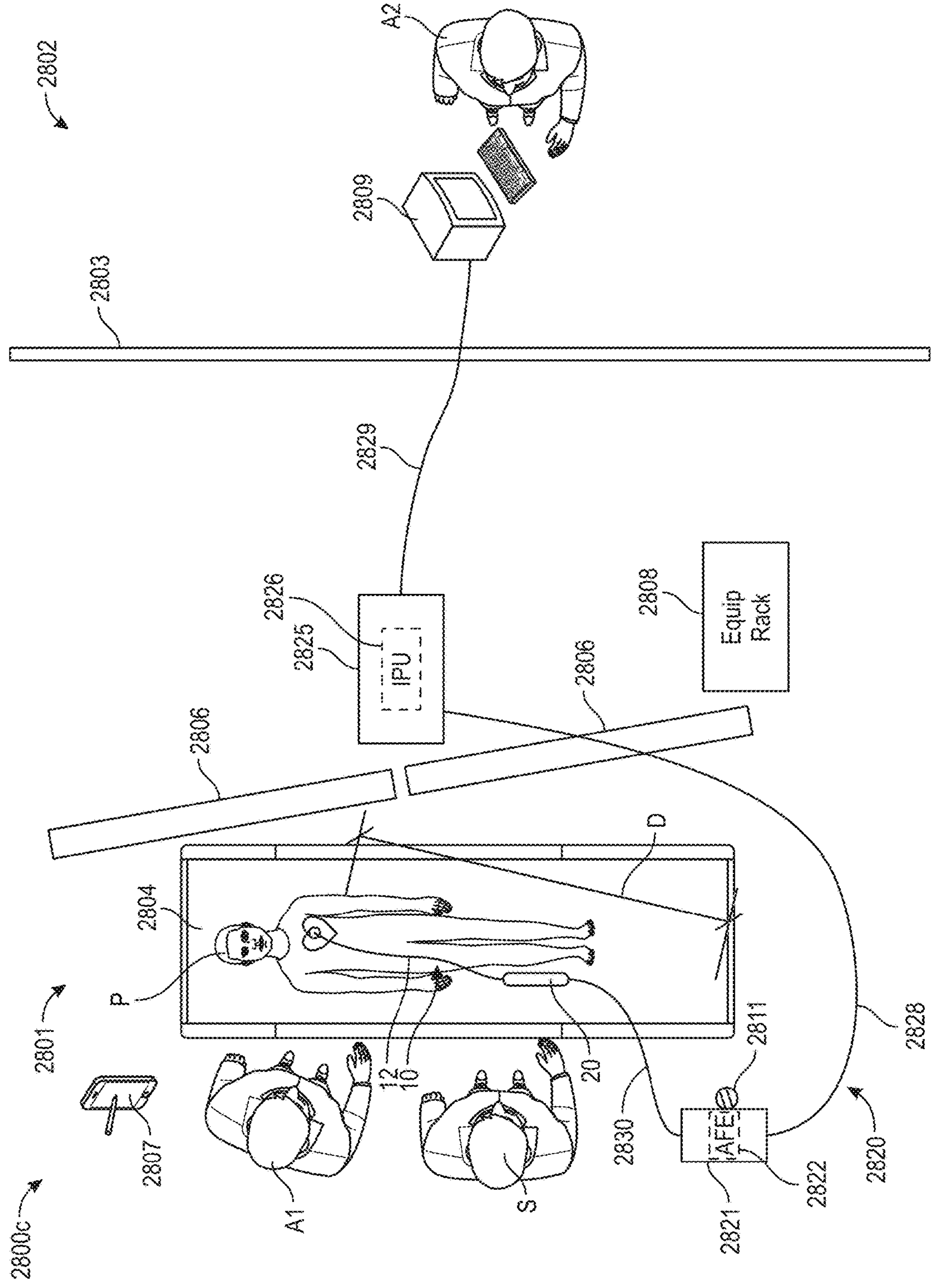

FIGS. 28B-28F illustrate additional representative operative setups 2800*b-d* for performing ICE procedures. In particular, FIGS. 28B and 28C illustrate the first housing

Figure 28D:
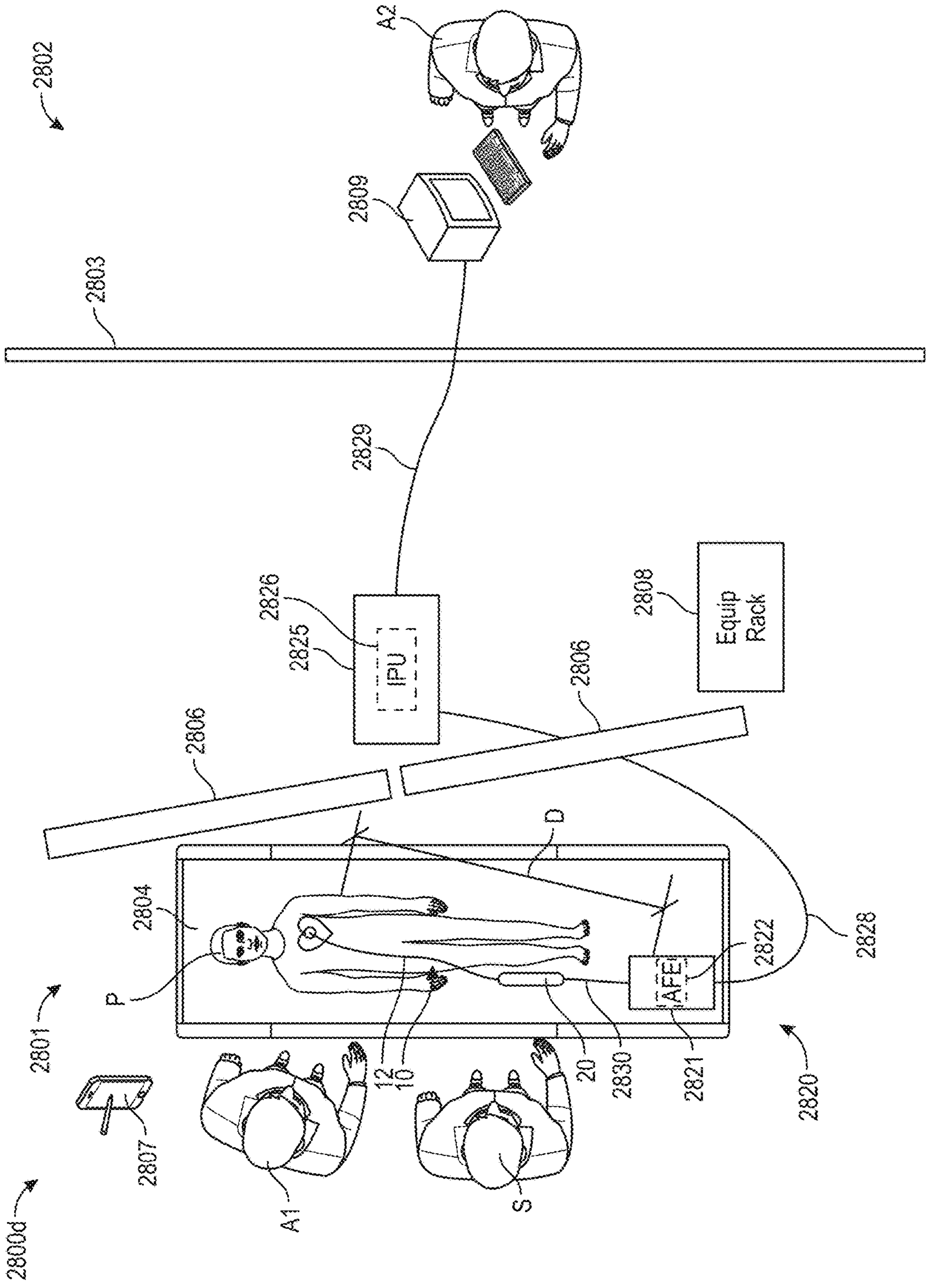
Figure 28E:
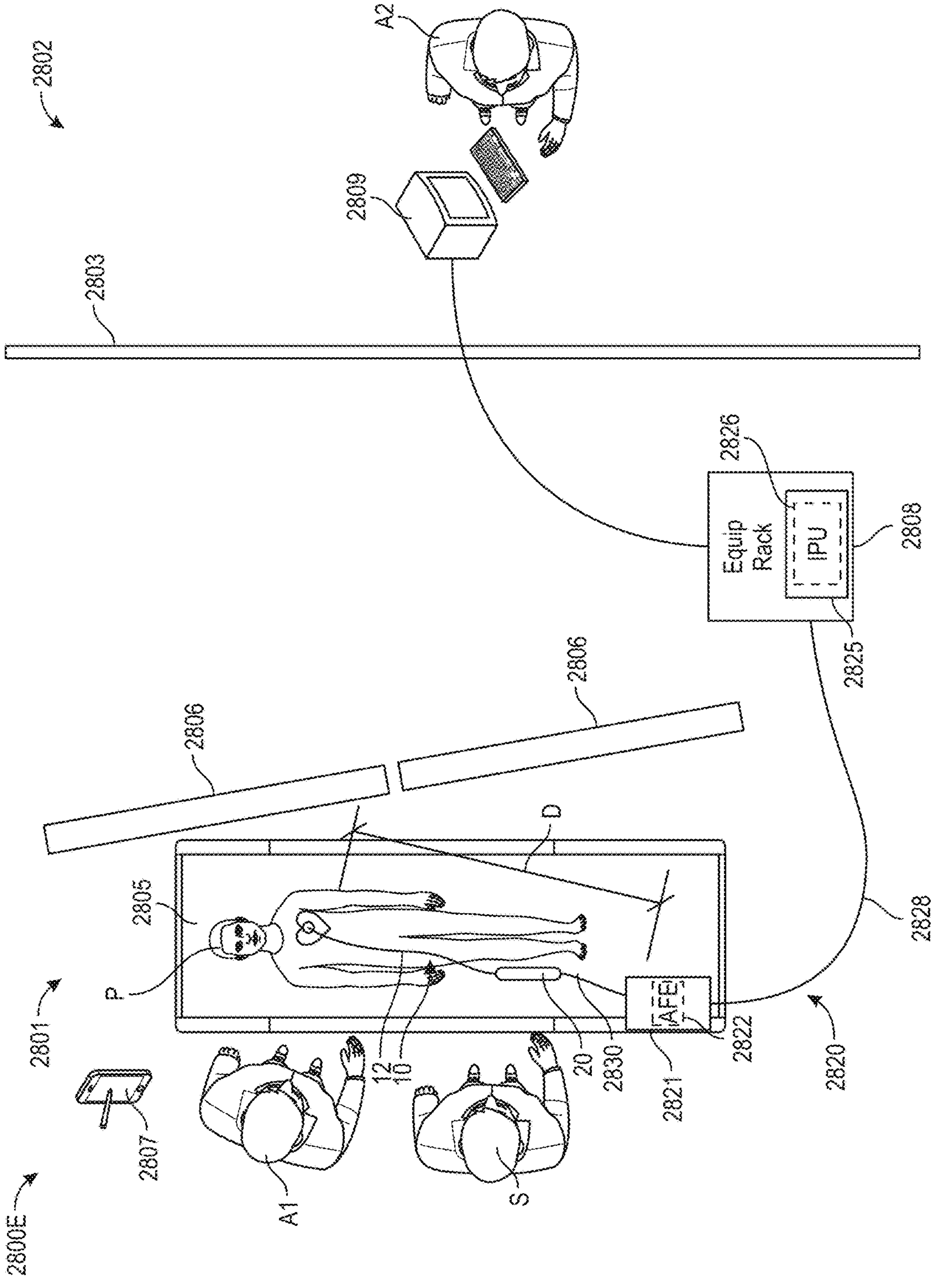
Figure 28F:
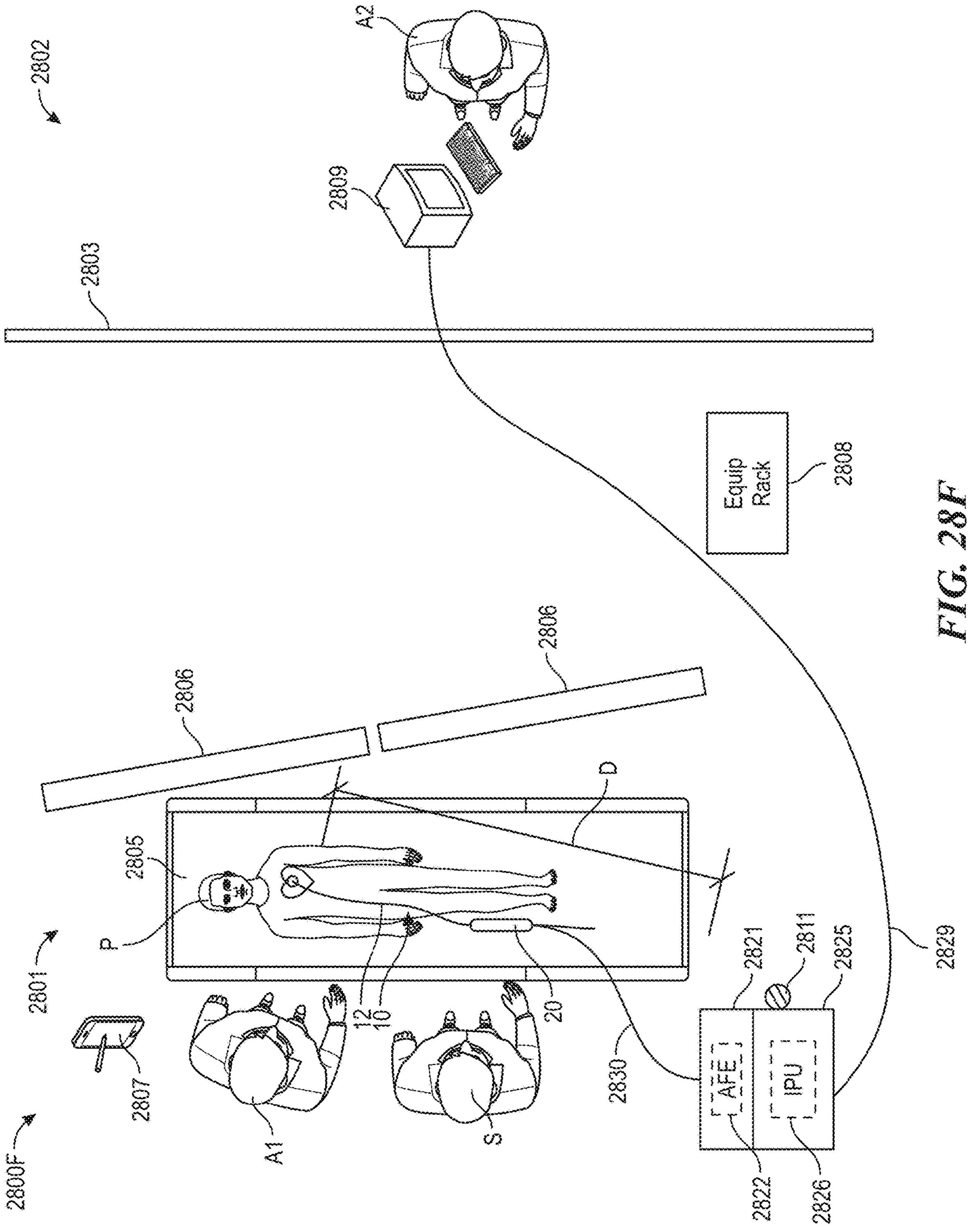

2821 positioned in a different position relative to the setup 2800*a* of FIG. 28A. For example, in the operative setup 2800*b* shown in FIG. 28B, the first housing 2821 with the AFE 2822 is mounted to an underside or to a side rail of the operating table 2804 (e.g., via a clamp, magnet, or other similar mechanism), and in the operative setup 2800*c* of FIG. 28C the first housing 2821 with the AFE 2822 is suspended from a pole 2811 (e.g., an IV dripper pole) near the foot of the operating table 2804 (e.g., via a ring, a clamp, or other similar mechanism). As one skilled in the art will appreciate, the first housing 2821 can be positioned at other locations near the operating table 2804, such as on the floor under the operating table 2804 or positioned on another structure adjacent the operating table 2804. FIGS. 28D and 28E illustrate different positions for the second housing 2825. For example, in the operative setup 2800*d* shown in FIG. 28D, the second housing 2825 can be attached to, suspended from, or otherwise positioned proximate a backside of the monitors 2806, and in the operative setup 2800*e* the second housing 2825 can be positioned on the equipment rack 2808. The first housing 2821 could alternatively be placed on the backside of the monitors 2806 either with or instead of the second housing 2825, with in the latter case the second housing 2825 placed elsewhere in the lab. In the operative setup 2800*f* shown in FIG. 28F, both the first housing 2821 and the second housing 2825 can be positioned near the operating table 2804 (e.g., suspended from the pole 2811, on the ground, on a rack, mounted to the operating table 2804, etc.). In such embodiments, the first housing 2821 can be removably coupled to the second housing 2825 for convenience.

As one skilled in the art will appreciate, each of the foregoing setup is expected to provide similar advantages to those described with reference to FIG. 28A. Further, the present technology is not limited to the setup described with reference to FIGS. 28A-28F, and instead can include other operative setups using the ultrasound module 2820 that enable the first housing 2821 to be positioned relatively close to the ICE catheter 10.

Figure 29:
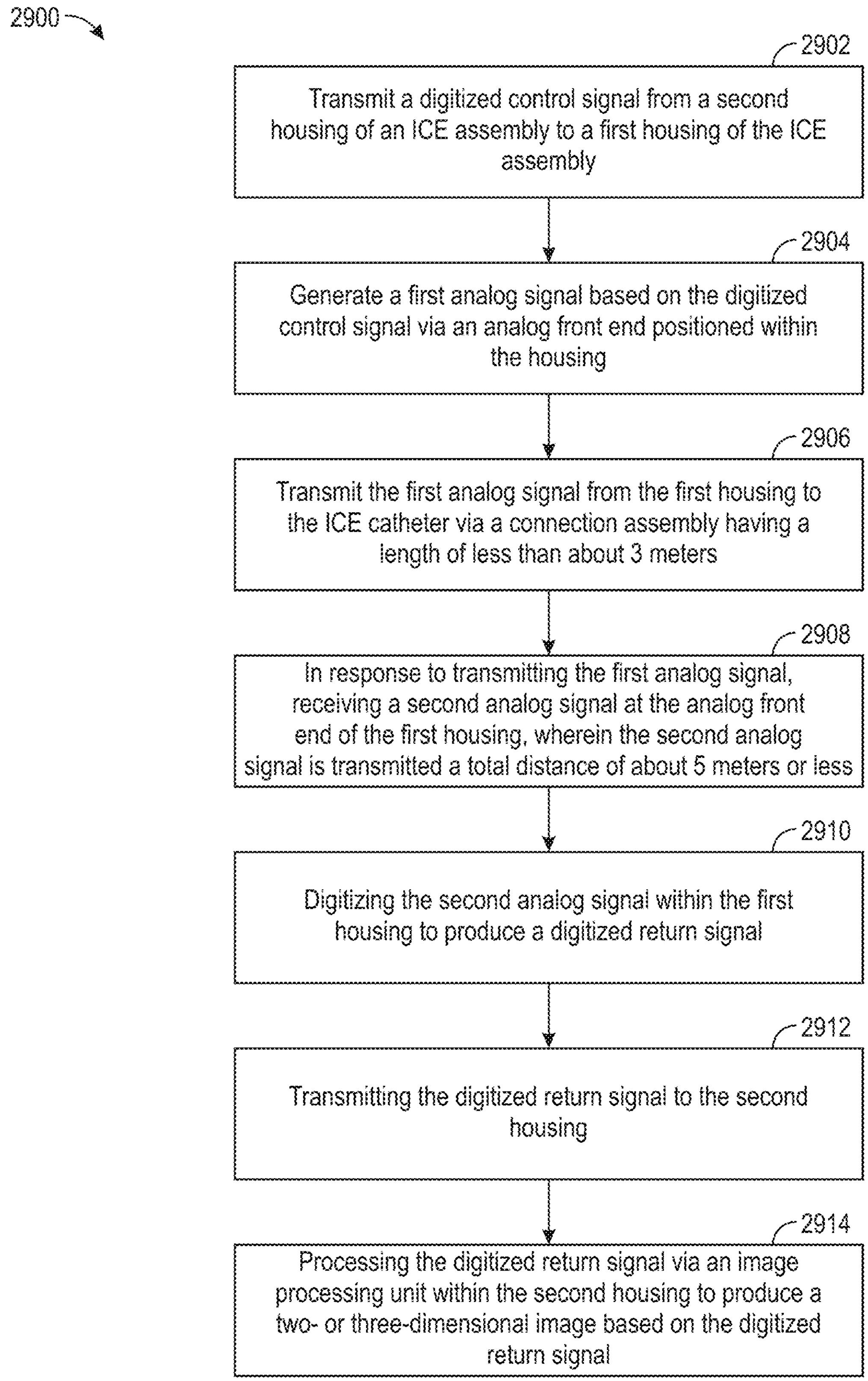
FIG. 29 is a flowchart of a method of performing intracardiac echocardiography in accordance with embodiments of the present technology.

FIG. 29 is a flowchart of a method 2900 of performing intracardiac echocardiography (ICE) on a patient in accordance with embodiments of the present technology. In some embodiments, the method 2900 of FIG. 29 can be performed using the ICE catheter 10 and the ICE ultrasound assembly 2720 or 2820 of FIGS. 27A-28F, although in other embodiments the method 2900 can be performed using other similar ICE catheters and ICE ultrasound assemblies. Accordingly, in some embodiments the method 2900 can be performed using an ICE ultrasound assembly that is at least partially incorporated into and/or shares certain components with other computing or medical systems, such as an EPMS.

The method 2900 can begin at block 2902 by transmitting a digitized control signal from a second housing of an ICE assembly to a first housing of the ICE assembly. In some embodiments, this may include transmitting the digitized signal from the second housing 2725 to the first housing 2721 of the ICE assembly 2720 of FIGS. 27A and 27B, or from the second housing 2825 to the first housing 2821 of the ICE assembly 2820 of FIG. 28. The digitized control signal can be transmitted via a connector cable, such as the cable 2728 or 2828 of FIGS. 27A-29F. The digitized control signal can be generated in response to and based on one or more user inputs received from a controller.

The method 2900 can continue at block 2904 by generating a first analog signal based on the digitized control signal. The first analog signal can be generated by an analog front end positioned within the first housing, such as the analog front ends 2722 or 2822 of FIGS. 27A-28F. At block 2906, the first analog signal can be transmitted from the first housing to the ICE catheter via a connection assembly having a length of less than about 3 meters. In some embodiments, the connection assembly can be the same as or similar to the connection assemblies 2730 and 2830 of FIGS. 27A-28F, and thus can have a total length of less than about 2.5 meters, less than about 2 meters, less than about 1.5 meters, less than about 1 meter, less than about 0.8 meters, less than about 0.6 meters, less than about 0.5 meters, less than about 0.4 meters, less than about 0.3 meters, less than about 0.2 meters, or less than about 0.1 meters. The first analog signal can be converted into ultrasound waves via a transducer on a distal tip region of the ICE catheter, which can be emitted into the patient. The first analog signal can therefore control various qualities and metrics of the ultrasound waves produced by the transducer. The return ultrasound waves can be captured by the transducer and converted into a second analog signal.

The method 2900 can then continue at block 2908 by receiving, in response to transmitting the first analog signal, a second analog signal at the analog front end of the first housing. As set forth above, the second analog signal may be generated by the transducer of the ICE catheter and be associated with the return ultrasound waves. Of note, the second analog signal can be transmitted a total distance of about 7 meters or less, about 6 meters or less, about 5 meters less, about 4 meters or less, about 3 meters or less, or about 2 meters or less. At block 2910, the method 2900 can include digitizing the second analog signal via the analog front end within the first housing to produce a digitized return signal. As set forth above, reducing the distance the second analog signal must be transmitted before being digitized is expected to advantageously reduce the distortion (e.g., due to noise, decay of signal, etc.) of the analog signal before it is converted into a digital signal, which may enable the ultrasound assembly to produce ultrasound images with higher fidelity, accuracy, speed, etc.

Once the digitized return signal is generated, the method 2900 can continue at block 2912 by transmitting the digitized return signal to the second housing, and at block 2914 by processing the digitized return signal via an image processing unit within the second housing (e.g., the image processing unit 2726 or 2827 of FIGS. 27A-28F). For example, the digitized return signal can be processed to produce a two- or three-dimensional image based on the digitized return signal for display to a user. The two- or three-dimensional image can be used to help guide additional intracardiac procedures, such as electrophysiology mapping, ablation, or the like.

ADDITIONAL EXAMPLES

Several aspects of the present technology are set forth in the following examples:

1. An ultrasound imaging catheter system, comprising:
an imaging sheath having an elongated tubular structure with a central lumen, the imaging sheath comprising a proximal shaft, a distal deflection region, a distal tip region, and an imaging window, optionally configured for deflection in the distal deflection region via one or more pull lines operably coupled to an actuator in a proximal handle.

2. The system of example 1, wherein the system further comprises an ultrasound imaging catheter that may be slidably positioned within the imaging sheath.

3. The system of example 2, wherein the ultrasound imaging catheter includes a distal imaging transducer, wherein the imaging sheath central lumen is sized and configured to allow slidable passage of the ultrasound imaging catheter therethrough such that the distal imaging transducer can be positioned within the sheath imaging window.

4. The system of example 2 or example 3, wherein the imaging window is configured to allow acoustic waves produced by the imaging catheter to pass through it without significant loss of image quality.

5. The system of any one of example 1-4, wherein the imaging window comprises an expandable member that is optionally arranged and configured to be filled with a fluid via a proximal port.

6. The system of any one of examples 2-5, wherein the system comprises a fluid lumen that is configured to facilitate fluid to be directed through the fluid lumen such that the fluid passes around the ultrasound imaging catheter transducer aligned within the sheath imaging window such that additional power may be delivered to the transducer with any heat generated by the extra power removed by the fluid such that the tissue interface with the ultrasound imaging catheter and imaging sheath does not exceed regulatory limits.

7. The system of any one of examples 1-6, wherein the imaging sheath comprises a distal extension.

8. An ultrasound imaging catheter system, comprising:

an ultrasound imaging catheter comprising a distal section including an imaging transducer, a catheter shaft, and a proximal handle, a plurality of electrical conductors coupled to the imaging transducer and routed through the ultrasound imaging catheter to a proximal connector on the proximal handle, the catheter shaft having a distal portion or section, a middle portion or section, and proximal portion or section, with a central or inner lumen therethrough, sized to accept a slidable steering device, and the plurality of electrical conductors extending proximally over the central or inner lumen of the catheter shaft.

9. The system of example 8, wherein the proximal handle includes a proximal port in communication with the central lumen of the catheter shaft.

10. The system of example 8 or example 9, further comprising a steering device comprising a steerable device shaft and a proximal handle in operable communication with the steerable device shaft, sized to be slidable within the ultrasound imaging catheter central lumen.

11. The system of example 10, wherein the steering catheter shaft is adapted to be deflected with at least one pull line in operable communication with a controller on the proximal handle.

12. The system of example 10 or example 11, wherein the steering catheter comprises a lumen in communication with a proximal port, wherein the lumen is adapted to allow fluid to be delivered through the lumen such that it exits a distal portion of the steering catheter.

13. The system of Example 12, wherein the ultrasound imaging catheter and the steering catheter are each sized, configured and arranged such that the fluid exiting the distal portion of the steering catheter is allowed to pass within the central or inner lumen of the ultrasound imaging catheter.

14. The system of example 13, wherein the distal end of the central lumen is closed to prevent communication with the surrounding body, wherein the fluid exiting the distal portion of the steering catheter is allowed to pass within the central lumen of the ultrasound imaging catheter, around one or more exterior surfaces of the steering catheter shaft, and exit a proximal port of the ultrasound imaging catheter.

15. The system of any one of examples 10-14, wherein the steerable device is slidably advanced within the central lumen to a portion within the distal section, and deflection of the steering device causes deflection of the distal shaft section of the ultrasound imaging catheter.

16. An ultrasound imaging catheter, comprising:

a distal portion comprising an imaging transducer, a catheter shaft, and a proximal handle, the catheter shaft comprising a distal shaft hinge, a distal deflectable shaft, and a proximal shaft, wherein the distal shaft hinge is between the distal portion and the distal deflectable shaft, wherein the proximal handle comprises at least one controller in operable communication with one or more pull lines routed through the catheter shaft and through the distal shaft hinge, the distal shaft hinge length being no longer than 15 mm and capable of being deflected at least 90 degrees, and has greater flexibility than the catheter portions just distal and proximal to it.

17. The catheter of example 16, wherein deflection of the distal deflectable shaft is achieved using at least one controller on the proximal handle in operable communication with a pull line routed within the distal deflectable shaft that is separate from the controller in operable communication with the distal shaft hinge.

18. The catheter of example 16 or example 17, wherein a plurality of electrical conductors are wound or braided within the catheter shaft at a first location at a greater picks per inch than a continuation of the plurality of electrical conductors within the shaft just proximal to the first location.

19. An ultrasound imaging catheter, comprising:

an outer shaft and an inner ultrasound member, the outer shaft having at least one lumen sized to slidably accept the inner ultrasound member therein, the inner ultrasound member comprising a proximal shaft section and a distal shaft section, and an ultrasound imaging transducer between the proximal and distal shaft sections.

20. The catheter of example 19, wherein an inner ultrasound member shaft hinge is positioned between the ultrasound imaging transducer and each of the proximal and distal inner shaft sections.

21. The catheter of example 19 or example 20, wherein a plurality of electrical conductors pass through the interior of at least one of the proximal or distal inner shaft sections to at least one electrical connector proximal to the proximal end of the outer shaft.

22. The catheter of any of examples 19-21, wherein each of the distal and proximal shaft sections extend proximal to the proximal end of the outer shaft and are independently slidably operable from a location proximal to the proximal outer shaft.

23. The catheter of any of examples 19-22, wherein the outer shaft is in operable communication with a mechanism on a proximal handle such that the outer shaft is adapted to be deflected in at least one direction.

24. An intracardiac ultrasound imaging catheter, comprising:

a distal portion and a catheter shaft, wherein the distal portion comprises a plurality of elongated transducer arrays, with each of the plurality of arrays is separated longitudinally by a flexible shaft section that allows the distal portion to flex more than if the transducer arrays were connected directly together.

25. A method of imaging an interior body tissue with ultrasound, where a sheath comprising a distal imaging window is steered into a target position within the body, and an ultrasound imaging catheter is advanced within the sheath such that the imaging catheter transducer remains within the sheath and aligns with the imaging window of the sheath to image the target body tissue.

26. A method of imaging an interior body tissue with ultrasound, comprising:

- inserting a steerable device into a central lumen of a flexible imaging catheter that comprises a transducer; and
- steering the imaging catheter with the steerable device when the steerable device is inserted within the central lumen of the imaging catheter.

27. The method of example 26, wherein the flexible imaging catheter is not adapted to be independently deflectable without the steerable device inserted into the central lumen.

28. The method of example 26, wherein a plurality of electrical conductors are routed through the imaging catheter and are not routed within a lumen of the steerable device.

29. A method of imaging an interior body tissue with ultrasound, comprising:

- steering an imaging transducer from a hinged shaft coupled to both a distal end and a proximal end of the transducer such that the transducer can be reoriented at least 180 degrees from a position it was when introduced into the body.

30. An imaging catheter, comprising:

- an ultrasound imaging catheter comprising a distal section including an imaging transducer, a catheter shaft, and a distal extension distal to the imaging transducer.

31. An intracardiac echocardiography (ICE) system, the system comprising:

- an ICE catheter, the ICE catheter including—
  - a proximal end region having a handle,
  - a distal end region having a transducer, and
  - a shaft extending between the proximal end region and the distal end region, wherein the shaft has a diameter of between about 6 French and about 14 French; and
- an ultrasound assembly, the ultrasound assembly including—
  - a first housing,
  - an analog-front-end positioned within the first housing,
  - a connection assembly extending from and/or configured to be coupled to the first housing to operably couple the analog-front-end to the handle, wherein the connection assembly has a length of less than about 2 meters,
  - a second housing different than the first housing,
  - an image processing unit positioned within the second housing, and
  - a cable configured to couple the first housing to the second housing to operably couple the analog-front-end and the image processing unit,
  - wherein the analog-front-end is configured to (a) transmit first electrical signals to the transducer via the connection assembly and the shaft for conversion into acoustic waves, (b) receive second electrical signals from the transducer via the shaft and the connection assembly, (c) digitize the received second electrical signals, and (d) transmit the digitized second electrical signals to the image processing unit via the cable, and
- wherein the image processing unit is configured to process the digitized second electrical signals.

32. The ICE system of example 31 wherein the cable is a first cable, and wherein the connection assembly includes a second cable having a length of less than about 2 meters.

33. The ICE system of example 32 wherein the length of the second cable is between about 0.5 meters and about 1 meter.

34. The ICE system of example 31 wherein the connection assembly is configured to directly connect the analog-front-end to the handle such that, when connected, the analog-front-end and the handle are in apposition.

35. The ICE system of example 34 wherein the connection assembly does not include a connector cable for connecting the analog-front-end to the handle.

36. The ICE system of any of examples 31-35 wherein the connection assembly includes a connector that is integral with the first housing.

37. The ICE system of any of examples 31-36 wherein the first housing includes one or more user interface controls for controlling the configuration of the analog-front-end.

38. The ICE system of any of examples 31-37 wherein the first housing has a volume of less than about 5000 cubic centimeters.

39. The ICE system of any of examples 31-38 wherein the first housing has a volume of less than about 300 cubic centimeters.

40. The ICE system of any of examples 31-39 wherein the cable is flexible such that a relative position between the first housing and the second housing can be changed.

41. The ICE system of example 40 wherein the first housing is configured to be positioned in apposition with the second housing.

42. The ICE system of any of examples 31-41 wherein the cable has a cable length of between about 4 meters and about 8 meters.

43. The ICE system of any of examples 31-42 wherein the system is configured to operate with a 0.5 to 3.0 decibel improvement in signal loss compared to conventional ultrasound systems.

44. The ICE system of any of examples 31-43 wherein the ultrasound assembly further comprises a controller with a user interface for controlling operation of the ultrasound assembly.

45. The ICE system of example 44 wherein the controller is wirelessly coupled to the image processing unit.

46. The ICE system of example 45 wherein the controller is configured to be usable within a sterile environment and accessible under a sterile drape.

47. The ICE system of any of examples 31-46 wherein the image processing unit is integrated into an electrophysiological mapping system.

48. The ICE system of example 47 further comprising a controller with a user interface for controlling operation of the ultrasound assembly, wherein the controller and the user interface are integrated into the electrophysiological mapping system.

49. An intracardiac echocardiography (ICE) ultrasound assembly for use with an ICE catheter, the ultrasound assembly comprising:

- a first housing,
- an analog-front-end positioned within the first housing,
- a connection assembly extending from and/or configured to be coupled to the first housing to operably couple the analog-front-end to a handle of the ICE catheter, wherein the connection assembly has a length of less than about 2 meters, a second housing different than the first housing, an image processing unit positioned within the second housing, and a cable configured to couple the first housing to the second housing to operably couple the analog-front-end and the image processing unit, wherein the analog-front-end is configured to (a) transmit first electrical signals to a transducer of the ICE catheter via the connection assembly for conversion into acoustic waves, (b) receive second electrical signals from the transducer via the connection assembly, (c) digitize the received second electrical signals, and (d) transmit the digitized second electrical signals to the image processing unit via the cable, and wherein the image processing unit is configured to process the digitized second electrical signals.

50. The ICE ultrasound assembly of example 49 wherein the first housing is configured to be removably coupled to an operating table.

51. The ICE ultrasound assembly of example 49 wherein the first housing is configured to be removably connected to a pole in an operating room.

52. The ICE ultrasound assembly of example 49 wherein the first housing is configured to be removably coupled to the second housing.

53. The ICE ultrasound assembly of any of examples 49-52 wherein the length of the connection assembly is less than about 1 meter.

54. The ICE ultrasound assembly of any of examples 49-53 wherein the length of the connection assembly is less than about 0.5 meters.

55. The ICE ultrasound assembly of any of examples 49-54 wherein the connection assembly includes a flexible cable.

56. The ICE ultrasound assembly of any of examples 49-55 wherein the first housing has a volume of less than about 1000 cubic centimeters.

57. The ICE ultrasound assembly of any of examples 49-56 wherein the first housing has a volume of less than about 200 cubic centimeters.

58. A system for providing intracardiac echocardiography (ICE) and electrophysiology mapping (EPM), the system comprising:

an EPM catheter comprising one or more electrodes;

an ICE catheter comprising a handle and a shaft, wherein the shaft includes a transducer;

an ultrasound module, the ultrasound module including— a first housing, a connection assembly extending from and/or configured to be coupled to the first housing, wherein the connection assembly has a length of less than about 2 meters, and an analog-front-end positioned within the first housing, wherein the analog-front-end is configured to (a) transmit first electrical signals to the transducer via the connection assembly and the shaft for conversion into acoustic waves, (b) receive second electrical signals from the transducer via the shaft and the connection assembly, and (c) digitize the received second electrical signals; and an EPM assembly, the EPM assembly including— a second housing different than the first housing, an image processing unit positioned within the second housing, wherein the image processing unit is configured to (d) receive the digitized second electrical signals from the analog-front-end of the ultrasound module, and (e) process the digitized second electrical signals to produce a two- or three-dimensional image based on the digitized second electrical signals, and an EPM processing unit positioned within the second housing, wherein the EPM processing unit is configured to (f) receive third electrical signals from the EPM catheter, and (g) process the third electrical signals to produce a map of an electrical activity of a patient's heart, wherein the ICE catheter is electrically connected to the image processing unit within the second housing of the EPM assembly via the ultrasound module, and wherein the EPM catheter is electrically connected to the EPM processing unit within the second housing of the EPM assembly without being electrically connected to the ultrasound module.

59. The system of example 58 wherein the image processing unit and the EPM processing unit are each integrated into a common computing structure.

60. The system of example 58 or example 59, further comprising a shared controller configured to control both the image processing unit and the EPM processing unit.

61. A method of performing intracardiac echocardiography (ICE) on a patient using an ICE system having an ICE catheter and an ICE ultrasound assembly including a first housing and a second housing, the method comprising:

transmitting a digitized control signal from the second housing of the ICE catheter to the first housing of the ICE catheter via a cable;

based on the digitized control signal, generating a first analog signal via an analog front end positioned within the first housing;

transmitting the first analog signal from the first housing to the ICE catheter via a connection assembly having a length of less than about 2 meters;

in response to transmitting the first analog signal, receiving a second analog signal at the analog front end of the first housing, wherein the second analog signal is received from the ICE catheter via the connection assembly, and wherein the second analog signal is transmitted a total distance of less than about 5 meters;

digitizing the second analog signal within the first housing to produce a digitized return signal;

transmitting the digitized return signal to the second housing; and processing the digitized return signal via an image processing unit within the second housing to produce a two- or three-dimensional image based on the digitized return signal.

62. The method of example 61, further comprising:

converting the first analog signal into ultrasound waves via a transducer on a distal tip region of the ICE catheter;

emitting the ultrasound waves from the transducer;

receiving return ultrasound waves at the transducer in response to emitting the ultrasound waves; and converting, via the transducer, the returned ultrasound waves into the second analog signal.

63. The method of example 61 or 62 wherein the first housing is positioned within a sterile operating room, and wherein the second housing is positioned within a nonsterile control room.

64. The method of any of examples 61-63 wherein the second housing is a component of an electrophysiology mapping system (EPMS).

65. The method of example 64 further comprising receiving a user input specifying one or more qualities of the digitized control signal, wherein receiving the user input includes receiving the user input via a controller shared with the EPMS.

66. The method of any of examples 61-65 wherein the second analog signal is transmitted a total distance of less than about 3 meters.

67. The method of any of examples 61-66 wherein the second analog signal is transmitted a total distance of less than about 2 meters.

CONCLUSION

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An intracardiac echocardiography (ICE) system, the system comprising:
- an ICE catheter, the ICE catheter including—
  - a proximal end region having a handle,
  - a distal end region having a transducer, and
  - a shaft extending between the proximal end region and the distal end region, wherein the shaft has a diameter of between about 6 French and about 14 French; and
- an ultrasound assembly, the ultrasound assembly including—
  - a first housing,
  - an analog-front-end positioned within the first housing,
  - a connection assembly extending from and/or configured to be coupled to the first housing to operably couple the analog-front-end to the handle, wherein the connection assembly has a length of less than about 2 meters,
  - a second housing different than the first housing,
  - an image processing unit positioned within the second housing, and
  - a cable configured to couple the first housing to the second housing to operably couple the analog-front-end and the image processing unit,
  - wherein the analog-front-end is configured to (a) transmit first electrical signals to the transducer via the connection assembly and the shaft for conversion into acoustic waves, (b) receive second electrical signals from the transducer via the shaft and the connection assembly, (c) digitize the received second electrical signals, and (d) transmit the digitized second electrical signals to the image processing unit via the cable, and
  - wherein the image processing unit is configured to process the digitized second electrical signals.

2. The ICE system of claim 1 wherein the cable is a first cable, and wherein the connection assembly includes a second cable having a length of less than about 2 meters.

3. The ICE system of claim 2 wherein the length of the second cable is between about 0.5 meters and about 1 meter.

4. The ICE system of claim 1 wherein the connection assembly is configured to directly connect the analog-front-end to the handle such that, when connected, the analog-front-end and the handle are in apposition.

5. The ICE system of claim 4 wherein the connection assembly does not include a connector cable for connecting the analog-front-end to the handle.

6. The ICE system of claim 1 wherein the first housing includes one or more user interface controls for controlling the configuration of the analog-front-end.

7. The ICE system of claim 1 wherein the first housing has a volume of less than about 5000 cubic centimeters.

8. The ICE system of claim 1 wherein the first housing has a volume of less than about 300 cubic centimeters.

9. The ICE system of claim 1 wherein the cable is flexible such that a relative position between the first housing and the second housing can be changed, and wherein the first housing is configured to be positioned in apposition with the second housing.

10. The ICE system of claim 1 wherein the cable has a cable length of between about 4 meters and about 8 meters.

11. The ICE system of claim 1 wherein the system is configured to operate with a 0.5 to 3.0 decibel improvement in signal loss compared to conventional ultrasound systems.

12. The ICE system of claim 1 wherein the ultrasound assembly further comprises a controller wirelessly coupled to the image processing unit and with a user interface for controlling operation of the ultrasound assembly, and wherein the controller is configured to be usable within a sterile environment and accessible under a sterile drape.

13. The ICE system of claim 1 wherein the image processing unit is integrated into an electrophysiological mapping system, and wherein the system further comprises:

a controller with a user interface for controlling operation of the ultrasound assembly, wherein the controller and the user interface are integrated into the electrophysiological mapping system.

14. A method of performing intracardiac echocardiography (ICE) on a patient using an ICE system having an ICE catheter and an ICE ultrasound assembly including a first housing and a second housing, the method comprising:

transmitting a digitized control signal from the second housing of the ICE catheter to the first housing of the ICE catheter via a cable;

based on the digitized control signal, generating a first analog signal via an analog front end positioned within the first housing;

transmitting the first analog signal from the first housing to the ICE catheter via a connection assembly having a length of less than about 2 meters;

in response to transmitting the first analog signal, receiving a second analog signal at the analog front end of the first housing, wherein the second analog signal is received from the ICE catheter via the connection assembly, and wherein the second analog signal is transmitted a total distance of less than about 5 meters;

digitizing the second analog signal within the first housing to produce a digitized return signal;

transmitting the digitized return signal to the second housing; and processing the digitized return signal via an image processing unit within the second housing to produce a two- or three-dimensional image based on the digitized return signal.

15. The method of claim 14, further comprising:

converting the first analog signal into ultrasound waves via a transducer on a distal tip region of the ICE catheter;

emitting the ultrasound waves from the transducer;

receiving return ultrasound waves at the transducer in response to emitting the ultrasound waves; and converting, via the transducer, the returned ultrasound waves into the second analog signal.

16. The method of claim 14 wherein the first housing is positioned within a sterile operating room, and wherein the second housing is positioned within a nonsterile control room.

17. The method of claim 14 wherein the second housing is a component of an electrophysiology mapping system (EPMS).

18. The method of claim 17 further comprising receiving a user input specifying one or more qualities of the digitized control signal, wherein receiving the user input includes receiving the user input via a controller shared with the EPMS.

19. The method of claim 14 wherein the second analog signal is transmitted a total distance of less than about 3 meters.

20. The method of claim 14 wherein the second analog signal is transmitted a total distance of less than about 2 meters.

* * * * *